(12) United States Patent
Bazan et al.

(10) Patent No.: US 12,075,697 B2
(45) Date of Patent: Aug. 27, 2024

(54) INERT SOLUTION-PROCESSABLE MOLECULAR CHROMOPHORES FOR ORGANIC ELECTRONIC DEVICES

(71) Applicant: The Regents of the University of California, Oakland, CA (US)

(72) Inventors: Guillermo C. Bazan, Goleta, CA (US); Thomas S. Van Der Poll, Goleta, CA (US); Thuc-Quyen Nguyen, Santa Barbara, CA (US); John Love, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/412,135

(22) Filed: Aug. 25, 2021

(65) Prior Publication Data

US 2022/0223797 A1 Jul. 14, 2022

Related U.S. Application Data

(63) Continuation of application No. 16/823,210, filed on Mar. 18, 2020, now abandoned, which is a continuation of application No. 16/203,189, filed on Nov. 28, 2018, now abandoned, which is a continuation of application No. 13/800,396, filed on Mar. 13, 2013, now abandoned.

(60) Provisional application No. 61/615,176, filed on Mar. 23, 2012.

(51) Int. Cl.
*H10K 85/60* (2023.01)
*B82Y 10/00* (2011.01)
*C07D 495/04* (2006.01)
*C07D 519/00* (2006.01)
*C07F 7/08* (2006.01)
*H10K 30/00* (2023.01)
*H10K 30/30* (2023.01)
*H10K 85/20* (2023.01)
*H10K 85/40* (2023.01)

(52) U.S. Cl.
CPC ............ *H10K 85/657* (2023.02); *B82Y 10/00* (2013.01); *C07D 495/04* (2013.01); *C07D 519/00* (2013.01); *C07F 7/0816* (2013.01); *H10K 30/00* (2023.02); *H10K 85/40* (2023.02); *H10K 85/655* (2023.02); *H10K 30/30* (2023.02); *H10K 85/215* (2023.02); *Y02E 10/549* (2013.01); *Y02P 70/50* (2015.11)

(58) Field of Classification Search
CPC ...... H10K 85/657; H10K 30/00; H10K 85/40; H10K 85/655; H10K 30/30; H10K 85/215; H10K 30/50; Y02E 10/549; Y02P 70/521; B82Y 10/00
See application file for complete search history.

(56) References Cited

U.S. PATENT DOCUMENTS

| | | | |
|---|---|---|---|
| 8,227,691 B2 | 7/2012 | Bazan et al. | |
| 8,273,599 B2 | 9/2012 | Bazan et al. | |
| 8,318,532 B2 | 11/2012 | Bazan et al. | |
| 8,723,169 B2 | 5/2014 | Bazan et al. | |
| 10,770,665 B2 | 9/2020 | Wood et al. | |
| 11,127,907 B2 | 9/2021 | Tamayo et al. | |
| 11,309,499 B2 | 4/2022 | Tamayo et al. | |
| 2006/0052612 A1 | 3/2006 | Stossel et al. | |
| 2006/0292736 A1 | 12/2006 | Lee et al. | |
| 2007/0169816 A1 | 7/2007 | Lee et al. | |
| 2007/0221926 A1 | 9/2007 | Lee et al. | |
| 2008/0315187 A1 | 12/2008 | Bazan et al. | |
| 2009/0032808 A1 | 2/2009 | Bazan et al. | |
| 2009/0108255 A1 | 4/2009 | Bazan et al. | |
| 2009/0126779 A1 | 5/2009 | Heeger et al. | |
| 2009/0188558 A1 | 7/2009 | Jen et al. | |
| 2010/0326525 A1 | 12/2010 | Nguyen et al. | |
| 2013/0032791 A1 | 2/2013 | Bazan et al. | |
| 2013/0240845 A1 | 9/2013 | Bazan et al. | |

(Continued)

FOREIGN PATENT DOCUMENTS

EP 2597127 A1 5/2013
JP 06-017307 1/1994

(Continued)

OTHER PUBLICATIONS

"Electronic." Merriam-Webster.com. Merriam-Webster, n.d. Web. Mar. 28, 2016.
Blouin, N. et al. (Sep. 19, 2007, e-pub. Dec. 21, 2007). "Toward a Rational Design of Poly (2,7-Carbazole) Derivatives for Solar Cells," *Journal of the American Chemical Society*, 130:732-742.
Chen, J.J.A. et al. (2010, e-pub. Aug. 30, 2010). "Auinacridone-Based Molecular Donors for Solution Processed Bulk-Heterojunction Organic Solar Cells," 2(9)2679-2686.

(Continued)

*Primary Examiner* — Alicia L Otton
(74) *Attorney, Agent, or Firm* — Morrison & Foerster LLP

(57) ABSTRACT

Small organic molecule chromophores containing a benzo [c][1,2,5]thiadiazole with an electron-withdrawing substituent W in the 5-position (5BTH), benzo[c][1,2,5]oxadiazole with an electron-withdrawing substituent W in the 5-position (5BO), 2H-benzo[d][1,2,3]triazole (5BTR) with an electron-withdrawing substituent W in the 5-position (5BTR), 5-fluorobenzo[c][1,2,5]thiadiazole (FBTH), 5-fluorobenzo[c][1,2,5]oxadiazole (FBO), or 5-fluoro-2H-benzo [d][1,2,3]triazole (FBTR) core structure are disclosed. Such compounds can be used in organic heterojunction devices, such as organic small molecule solar cells and transistors.

10 Claims, 5 Drawing Sheets

(56) References Cited

U.S. PATENT DOCUMENTS

| | | |
|---|---|---|
| 2013/0247990 A1 | 9/2013 | Facchetti et al. |
| 2014/0167002 A1 | 6/2014 | Welch et al. |
| 2016/0020413 A1* | 1/2016 | Tamayo .............. H01L 51/4253 |
| | | 136/263 |
| 2021/0043845 A1 | 2/2021 | Bazan et al. |

FOREIGN PATENT DOCUMENTS

| | | |
|---|---|---|
| WO | WO-2011/049531 A1 | 4/2011 |
| WO | WO-2012/074853 A1 | 6/2012 |
| WO | WO-2012/178116 A1 | 12/2012 |

OTHER PUBLICATIONS

Coffin, R.C., et al. (Nov. 2009, e-pub. Oct. 18, 2009). "Streamlined Microwave-Assisted Preparation of Narrow-Bandgap Conjugated Polymers for High-Performance Bulk Heterojunction Solar Cells," *Nat. Chem.* 1:657-661.

Gupta, V. et al. (Apr. 2, 2013, pub. Jun. 11, 2013). "Barium: An Efficient Cathode Layer for Bulk-Heterojunction Solar Cells," *Scientific Reports*, 1-6.

Hau, S.K. et al. (2010, pub. Nov. 6, 2010). "A Review on the Development of the Inverted Polymer Solar Cell Architecture," *Polymer Reviews*, 50(4):474-510.

Henson, Z. B. et al., (Oct. 4, 2011, e-pub. Jan. 27, 2012). "Pyridalthiadiazole-Based Narrow Band Gap Chromophores," *J. Am. Chem. Soc.* 134(8):3766-3779.

International Search Report mailed on Jul. 17, 2013, for PCT Patent Application No. PCT/US2013/033615, filed Mar. 22, 2013, 4 pages.

Kyaw, A.K.K. et al. (May 13, 2013, pub. Jun. 27, 2013). "Improved Light Harvesting and Improved Efficiency by Insertion of an Optical Spacer (ZnO) in Solution-Processed Small-Molecule Solar Cells," *Nano Lett.*, 13:3796-3801.

Leroy, J. et al. (Sep. 28, 2006, e-pub. Jan. 17, 2007). "Symmetrical and Nonsymmetrical Liquid Crystalline Oligothiophenes: Convenient Synthesis and Transition-Temperature Engineering," *Eur. J. Org. Chem.*, 1256-1261.

Love, J.A. et al. (2013). "Film Morphology of High Efficiency Solution-Processed Small-Molecule Solar Cells," *Adv. Funct. Matter.*, 23:5019-5026.

Machine translation of JP 06-017307, obtained from <http://worldwide.espacenet.com/>, Accessed Mar. 28, 2016.

Non-Final Office Action mailed on Apr. 1, 2016, for U.S. Appl. No. 13/800,396, filed Mar. 13, 2013, 15 pages. (57.00).

Peng, Q. et al., (2011). "Novel Benzo[1,2-b:4,5-b̄]dithiophene-Benzothiadiazole Derivatives with Variable Side Chains for High-Performance Solar Cells," *Adv. Mater.* 23:4554-4558.

Perez, L.A. et al. (May 25, 2013, e-pub. Sept. 4, 2013). "Solvent Additive Effects on Small Molecule Crytallization in Bulk Heterojunction Solar Cells Probed During Spin Casting," Adv. Mater., 25:6380-6384.

Restriction Requirement mailed on Sep. 28, 2015, for U.S. Appl. No. 13/800,396, filed Mar. 13, 2013, 8 pages. (57.00).

Sharif, M. et al., (Feb. 2, 2010, e-pub. Mar. 20, 2010). "One-Pot Synthesis of Fluorinated Terphenyls by Site-Selective Suzuki-Miyaura Reactions of 1,4-Dibromo-2-Fluorobenzene," *Teterahedron Letters* 51:2810-2812.

Sun, Y. et al., (Jan. 2012, e-pub. Nov. 6, 2011). "Solution-Processed Small-Molecule Solar Cells with 6.7% Efficiency," *Nat. Mater.* 11:44-48.

Takacs, C.J. et al. (May 31, 2012, pub. Sept. 6, 2012). "Solar Cell Efficiency, Self-Assembly, and Dipole-Dipole Interactions of Isomorphic Narrow-Band-Gap Molecules," *J. Am. Chem. Soc.*, 134:16597-16606.

Van Der Poll, T.S. et al. (Mar. 19, 2012, e-pub. Jun. 6, 2012). "Non-Basic High-Performance Molecules for Solution-Processed Organic Solar Cells," *Adv. Mater.*, 24:3646-3649.

Welch, G. C. et al., (2011). "Lewis Acid Adducts of Narrow Band Gap Conjugated Polymers," *J. Am. Chem. Soc.*, 133:4632-4644.

Welch, G.C. et al., (2011). "A Modular Molecular Framework for Utility in Small-Molecule Solution-Processed Organic Photovoltaic Devices," *J. of Matter. Chem.*, 21:12700-12709.

Written Opinion mailed on Jul. 16, 2013, for PCT Application No. PCT/US2013/033615, Internationally filed on Mar. 22, 2013, 6 pages.

Zhang, J. et al., (Aug. 26, 2009, e-pub. Sep. 30, 2009). "Solution-Processable Star-Shaped Photovoltaic Organic Molecule with Triphenylamine Core and Benzothiadiazole-Thiophene Arms," *Macromolecules* 42(20):7619-7622.

Zhang, Y. et al., (2011). "Increased Open Circuit Voltage in Fluorinated Benzothiadiazole-Based Alternating Conjugated Polymers," *Chemical Communications* 47(39):11026-11028.

* cited by examiner

INERT SOLUTION-PROCESSABLE MOLECULAR CHROMOPHORES FOR ORGANIC ELECTRONIC DEVICES

CROSS-REFERENCE TO RELATED APPLICATIONS

This application is a continuation application of U.S. patent application Ser. No. 16/823,210, filed Mar. 18, 2020 which is a continuation application of U.S. patent application Ser. No. 16/203,189, filed Nov. 28, 2018, now abandoned which is a continuation application of U.S. patent application Ser. No. 13/800,396 filed Mar. 13, 2013, now abandoned, which claims priority benefit of U.S. Provisional Patent Application No. 61/615,176, filed Mar. 23, 2012. The entire contents of those applications are hereby incorporated by reference herein.

STATEMENT REGARDING FEDERALLY SPONSORED RESEARCH OR DEVELOPMENT

This invention was made with United States government support under grant no. DE-SC0001009 awarded by the Center for Energy Efficient Materials of the Department of Energy. The government has certain rights in the invention.

BACKGROUND OF THE INVENTION

Small-molecule bulk-heterojunction (SM BHJ) solar cells have become a competitive alternative to the exhaustively studied polymer organic photovoltaics (OPV). Intense investigation into the design and utility of conjugated polymers for light harvesting has provided great insight into the design and implementation of organic semiconductors for OPV technology, to the point where power conversion efficiencies (PCEs) up to 8.4% have been achieved. However, polymer systems inherently suffer from batch-to-batch variations and limited options for purification of the polymeric materials. Small-molecule semiconductors avoid the drawbacks inherent to polymeric semiconductors, as they are monodisperse in nature and, due to having a higher solubility than polymeric analogs, can be purified and characterized using standard organic chemistry protocols. Additionally, modifications to fine-tune properties can be made to small molecules more readily and with fewer complications. Recently, it has been demonstrated that small molecule-based solar cells can achieve efficiencies comparable to that of polymer-based solar cells. See Sun, Y. et al., *Nat. Mater.* 2011, 11, 44-48; Welch, G. C.; Bazan, G. C. *J. Am. Chem. Soc.* 2011, 133, 4632-4644; Welch, G. C. et al., *J. of Mater. Chem.* 2011, 21, 12700-12709; Henson, Z. B. et al., *J. Am. Chem. Soc.* 2012, 134 (8), 3766-3779; Zhang, Y. et al., *Chem. Commun.,* 2011, 47, 11026-11028; Peng, Q. et al., *Adv. Mater.* 2011, 23, 4554-4558; and Sharif, M. et al., *Teterahedron Lett.* 2010, 51, 2810-2812.

A small molecule system with a central electron-rich core, flanked by relatively electron-poor units, and terminated with a π-conjugated end-cap has been previously described (Welch et al., J. Materials Chemistry 21(34):12700-12709 (2011); U.S. Provisional Patent Appl. No. 61/416,251; International Patent Appl. No. PCT/US2011/061963; the contents of these publications are hereby incorporated by reference herein in their entireties). The success of this system is in large part due to the inclusion of pyridal[2,1,3]thiadiazole (PT) as an acceptor unit. The PT-based compounds have led to fabrication of a SM BHJ solar cell with a PCE of 6.7% (see Sun et al., Nature Materials, 11:44-48 (2011).

One drawback to using PT-based materials in fabrication of small molecule solar cells is that the cells must employ molybdenum oxide as a hole-transport layer (HTL) for maximum efficiency. Molybdenum oxide is thermally evaporated onto devices, which prevents the use of inexpensive solution deposition during roll-to-roll manufacture. It would be preferable to use a solution-processable HTL material, such as poly(3,4-ethylenedioxythiophene) poly (styrenesulfonate) (PEDOT:PSS), or other doped conjugated polymers. However, PEDOT:PSS bears acidic protons, which, when deposited at an interface with the active layer, will protonate the pyridyl nitrogen of the pyridal[2,1,3] thiadiazole. This protonation results in a drastic reduction in the PCE of devices fabricated using PEDOT:PSS as the anode interlayer that use PT containing small molecule donors. Other systems with labile protons and protonatable semiconductors will also lead to deterioration of power conversion efficiency.

Thus, there is a need for high-efficiency small molecule materials which do not limit manufacturing options, and which do not have sites that react with materials such as PEDOT:PSS, other acidic materials, or materials deposited from an acidic solution. The present invention seeks to address the need for improved light harvesting molecules for molecular heterojunction devices by providing novel and advantageous materials for use in such devices.

SUMMARY OF THE INVENTION

In one embodiment, the present invention is directed to organic non-polymeric chromophores containing the benzo [c][1,2,5]thiadiazole with an electron-withdrawing substituent W in the 5-position (5BTH), of the following structure:

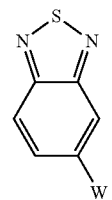

the benzo[c][1,2,5]oxadiazole with an electron-withdrawing substituent W in the 5-position (5BO), of the following structure:

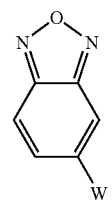

or the 2H-benzo[d][1,2,3]triazole with an electron-withdrawing substituent W in the 5-position (5BTR) (and N2-substituted derivatives thereof) of the following structure:

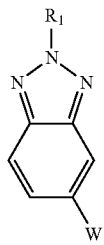

where $R_1$ is H, $C_1$-$C_{30}$ alkyl or $C_6$-$C_{30}$ aryl;

and where W is selected from F, Cl, Br, I, —CN, —CF$_3$, —CHF$_2$, or —CH$_2$F;

for use in heterojunction devices, such as organic small molecule solar cells and transistors. The organic non-polymeric chromophores can be used in an electronic or optoelectronic device, for example, in the active layer of such a device.

In one embodiment, W is F. In one embodiment, W is Cl. In one embodiment, W is Br. In one embodiment, W is I. In one embodiment, W is —CN. In one embodiment, W is —CF$_3$. In one embodiment, W is —CHF$_2$. In one embodiment, W is —CH$_2$F.

In one embodiment, the present invention is directed to organic non-polymeric chromophores containing the 5-fluorobenzo[c][1,2,5]thiadiazole (FBTH) structure:

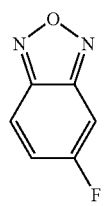

the 5-fluorobenzo[c][1,2,5]oxadiazole (FBO) structure:

or the 5-fluoro-2H-benzo[d][1,2,3]triazole (FBTR) structure (and N2-substituted derivatives thereof):

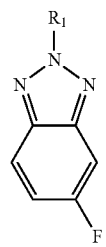

where $R_1$ is H, $C_1$-$C_{30}$ alkyl or $C_6$-$C_{30}$ aryl;

for use in heterojunction devices, such as organic small molecule solar cells and transistors.

In one embodiment, the present invention is directed to non-polymeric electron-donating and electron-accepting chromophores having a core structure of benzo[c][1,2,5]thiadiazole with an electron-withdrawing substituent W in the 5-position (5BTH), benzo[c][1,2,5]oxadiazole with an electron-withdrawing substituent W in the 5-position (5BO), or 2H-benzo[d][1,2,3]triazole (5BTR) with an electron-withdrawing substituent W in the 5-position (5BTR). In another embodiment, the present invention is directed to non-polymeric electron-donating and electron-accepting chromophores having a core structure of 5-fluorobenzo[c][1,2,5]thiadiazole (FBTH), 5-fluorobenzo[c][1,2,5]oxadiazole (FBO), or 5-fluoro-2H-benzo[d][1,2,3]triazole (FBTR) core structure. In another embodiment, the present invention is directed to optoelectronic devices comprising an active layer composition of a mixture of a non-polymeric light-harvesting electron-donating chromophore based on a 5BTH, 5BO, 5BTR, FBTH, FBO, or FBTR core structure with an electron-accepting material, such as a fullerene, methanofullerene, arylene diimides or related π-conjugated organic electron acceptors. Organic or inorganic electron acceptors can be used. In another embodiment, the present invention is directed to optoelectronic devices comprising an active layer composition of a mixture of a non-polymeric light-harvesting electron-accepting chromophore based on a 5BTH, 5BO, 5BTR, FBTH, FBO, or FBTR core structure with an electron-donating material. Organic or inorganic electron donors can be used. The present invention is also directed to methods of fabricating the devices by solution processing. In one embodiment, all active layers of the described optoelectronic devices are formed from solutions comprising of non-polymeric discrete organic materials.

In one embodiment, the invention embraces compounds of Formula I:

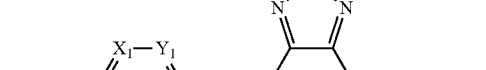

Formula I where $X_1$ and $Y_1$ are selected from —C(W)— and CH, where when $X_1$ is —C(W)—, $Y_1$ is CH, and when $X_1$ is CH, $Y_1$ is —C(W)—; and where, independently of $X_1$ and $Y_1$, $X_2$ and $Y_2$ are selected from —C(W)— and CH, where when $X_2$ is —C(W)—, $Y_2$ is CH, and when $X_2$ is CH, $Y_2$ is —C(W)—;

where W is selected from F, Cl, Br, I, —CN, —CF$_3$, —CHF$_2$, or —CH$_2$F;

M is selected from sulfur (S), oxygen (O), or N—R$_1$, where R$_1$ is H, $C_1$-$C_{30}$ alkyl or $C_6$-$C_{30}$ aryl;

and, in additional embodiments, compounds of Formula Ia, Formula Ib, and Formula Ic, Formula Ia-F, Formula Ib-F, and Formula Ic-F:

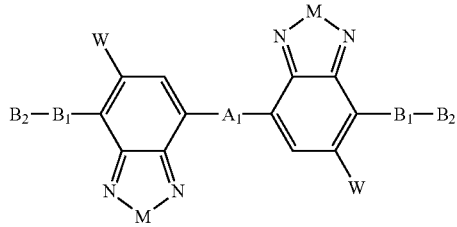

Ia

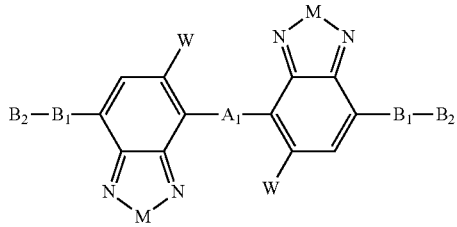

Ib

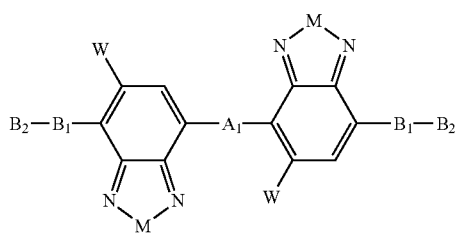

Ic

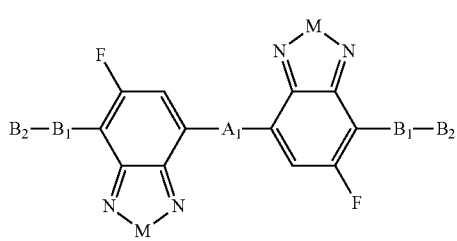

Ia-F

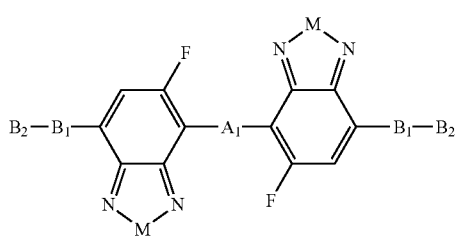

Ib-F

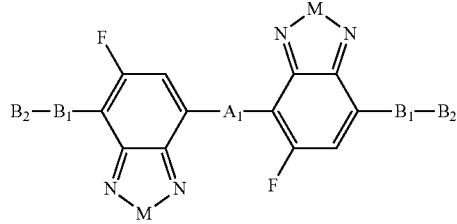

Ic-F where $A_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, dithienopyrrole, dithienophosphole and carbazole 9,9-RR'-9H-fluorene, 9-R-9H-carbazole, 3,3'-RR'silylene-2,2'-bithiophene, 3,3'RR'-cyclopenta[2,1-b:3,4-b']-dithiophene, where R and R'=$C_1$-$C_{30}$ alkyl or $C_6$-$C_{30}$ aryl;

where each $B_1$ is independently selected from substituted or unsubstituted aryl or heteroaryl groups such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, and carbazole; and where each $B_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups.

In another embodiment, the invention embraces compounds of Formula II:

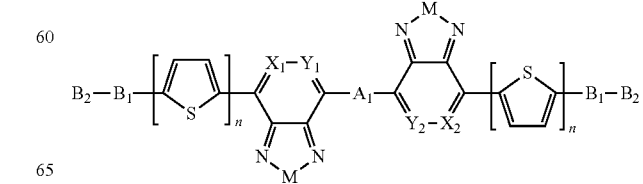

II where $X_1$ and $Y_1$ are selected from —C(W)— and CH, where when $X_1$ is —C(W)—, $Y_1$ is CH, and when $X_1$ is CH, $Y_1$ is —C(W)—; and where, independently of $X_1$ and $Y_1$, $X_2$ and $Y_2$ are selected from —C(W)— and CH, where when $X_2$ is —C(W)—, $Y_2$ is CH, and when $X_2$ is CH, $Y_2$ is —C(W)—;

M is selected from sulfur (S), oxygen (O), or N—$R_1$, where $R_1$ is H, $C_1$-$C_{30}$ alkyl or $C_6$-$C_{30}$ aryl;

where W is selected from F, Cl, Br, I, —CN, —CF$_3$, —CHF$_2$, or —CH$_2$F;

n is an integer between 0 and 5, inclusive;

$A_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, dithienopyrrole, dithienophosphole and carbazole 9,9-RR'-9H-fluorene, 9-R-9H-carbazole, 3,3'-RR'silylene-2,2'-bithiophene, 3,3'RR'-cyclopenta[2,1-b:3,4-b']-dithiophene, where R and R'=$C_1$-$C_{30}$ alkyl or $C_6$-$C_{30}$ aryl;

each $B_1$ is independently selected from substituted or unsubstituted aryl or heteroaryl groups such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, and carbazole; and each $B_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups.

In one embodiment, n is an integer between 0 and 5, inclusive. In another embodiment, n is 0. In another embodiment, n is 1. In another embodiment, n is 2. In another embodiment, n is 3. In another embodiment, n is 4. In another embodiment, n is 5.

In some embodiments of Formula II, $X_1$ and $X_2$ are each —C(W)— and $Y_1$ and $Y_2$ are each CH. In some embodiments of Formula II, $X_1$ and $X_2$ are each CH and $Y_1$ and $Y_2$ are each —C(W)—. In any of the foregoing embodiments, W can be F.

In some embodiments of Formula II, $X_1$ and $X_2$ are each —C(W)—, $Y_1$ and $Y_2$ are each CH and each M is S. In some embodiments of Formula II, $X_1$ and $X_2$ are each CH, $Y_1$ and $Y_2$ are each —C(W)—, and each M is S. In any of the foregoing embodiments, W can be F.

In some embodiments of Formula II, $X_1$ and $X_2$ are each —C(W)—, $Y_1$ and $Y_2$ are each CH and each M is O. In some embodiments of Formula II, $X_1$ and $X_2$ are each CH, $Y_1$ and $Y_2$ are each —C(W)—, and each M is O. In any of the foregoing embodiments, W can be F.

In preferred embodiments, $B_2$ is selected from the group consisting of a nonentity, H, F, a $C_1$-$C_{16}$ alkyl group, thiophene, benzothiophene, benzofuran, and benzothiazole.

In further embodiments, $B_2$ is phenyl, substituted at the p-position with diphenylamine (i.e., the $B_2$ moiety is triphenylamine)

In another embodiment, the invention embraces compounds of Formula II of Formula IIa, Formula IIb, Formula IIc, Formula IIa-F, Formula IIb-F, or Formula IIc-F:

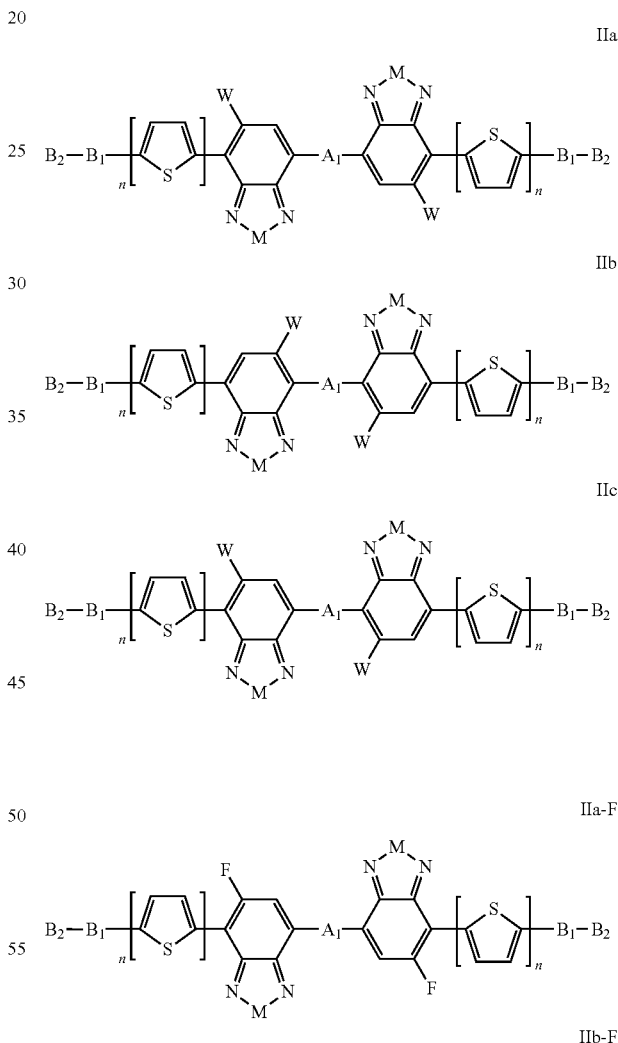

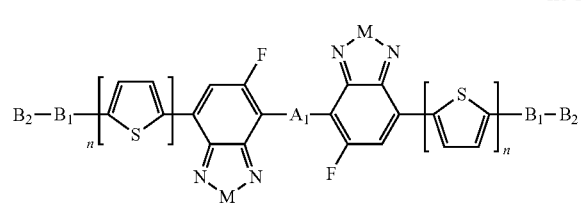

-continued (IIc-F)

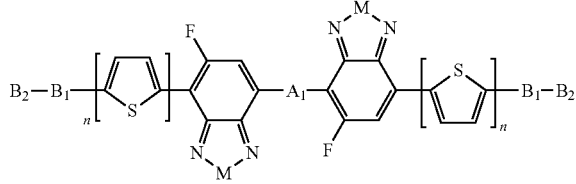

M is selected from sulfur (S), oxygen (O), or N—$R_1$, where $R_1$ is H, $C_1$-$C_{30}$ alkyl or $C_6$-$C_{30}$ aryl;

W is selected from F, Cl, Br, I, —CN, —$CF_3$, —$CHF_2$, or —$CH_2F$; in further embodiments, W is F;

n is an integer between 0 and 5, inclusive;

$A_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, dithienopyrrole, dithienophosphole and carbazole 9,9-RR'-9H-fluorene, 9-R-9H-carbazole, 3,3'-RR'silylene-2,2'-bithiophene, 3,3'RR'-cyclopenta[2,1-b:3,4-b']-dithiophene, where R and R'=$C_1$-$C_{30}$ alkyl or $C_6$-$C_{30}$ aryl;

each $B_1$ is independently selected from substituted or unsubstituted aryl or heteroaryl groups such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, and carbazole; and each $B_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups.

In one embodiment, n is an integer between 0 and 5, inclusive. In another embodiment, n is 0. In another embodiment, n is 1. In another embodiment, n is 2. In another embodiment, n is 3. In another embodiment, n is 4. In another embodiment, n is 5.

In some embodiments of Formula IIa, each M is S.
In some embodiments of Formula IIa, each M is O.
In some embodiments of Formula IIb, each M is S.
In some embodiments of Formula IIb, each M is O.
In some embodiments of Formula IIc, each M is S.
In some embodiments of Formula IIc, each M is O.
In some embodiments of Formula IIa-F, each M is S.
In some embodiments of Formula IIa-F, each M is O.
In some embodiments of Formula IIb-F, each M is S.
In some embodiments of Formula IIb-F, each M is O.
In some embodiments of Formula IIc-F, each M is S.
In some embodiments of Formula IIc-F, each M is O.

In some embodiments, the compounds of Formula II are selected from compounds of Formula IId:

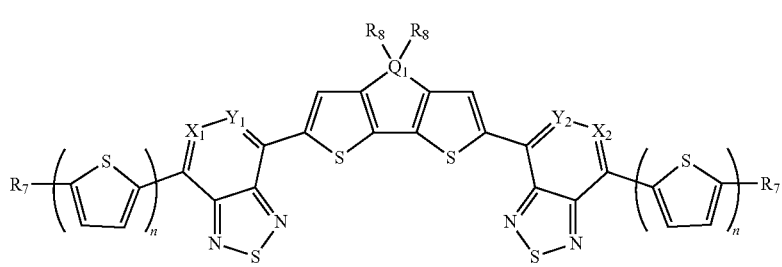

(IId)

where $Q_1$ is C or Si;

where $X_1$ and $Y_1$ are selected from —C(W)— and CH, where when $X_1$ is —C(W)—, $Y_1$ is CH, and when $X_1$ is CH, $Y_1$ is —C(W)—; and where, independently of $X_1$ and $Y_1$, $X_2$ and $Y_2$ are selected from —C(W)— and CH, where when $X_2$ is —C(W)—, $Y_2$ is CH, and when $X_2$ is CH, $Y_2$ is —C(W)—;

W is selected from F, Cl, Br, I, —CN, —$CF_3$, —$CHF_2$, or —$CH_2F$; in further embodiments, W is F;

n is 0, 1, 2, or 3;

$R_7$ is selected from H, $C_1$-$C_{16}$ alkyl, —O—$C_1$-$C_{16}$ alkyl, benzofuran-2-yl, benzothiophene-2-yl, and benzothiazole-2-yl; and $R_8$ is selected from H, $C_1$-$C_{16}$ alkyl or —O—$C_1$-$C_{16}$ alkyl.

In one embodiment of Formula IId, $Q_1$ is C.
In one embodiment of Formula IId, $Q_1$ is Si.
In one embodiment of Formula IId, $X_1$ and $X_2$ are —C(W)— and $Y_1$ and $Y_2$ are CH; in a further embodiment, W is F.

In one embodiment of Formula IId, $X_1$ and $X_2$ are CH and $Y_1$ and $Y_2$ are —C(W)—; in a further embodiment, W is F.

In one embodiment of Formula IId, n is 2.
In one embodiment of Formula IId, $R_7$ is selected from H or $C_1$-$C_{16}$ alkyl.
In one embodiment of Formula IId, $R_7$ is selected from benzofuran-2-yl.
In one embodiment of Formula IId, $R_7$ is selected from benzothiophene-2-yl.

In one embodiment of Formula IId, $R_7$ is selected from benzothiazole-2-yl.

In one embodiment of Formula IId, $R_8$ is selected from H or $C_1$-$C_{16}$ alkyl.

In one embodiment of Formula IId, $R_8$ is selected from $C_1$-$C_{16}$ alkyl.

In one embodiment of Formula IId, $Q_1$ is C, $X_1$ and $X_2$ are —C(W)—, and $Y_1$ and $Y_2$ are CH; in a further embodiment of this type, W is F.

In one embodiment of Formula IId, $Q_1$ is C, $X_1$ and $X_2$ are CH, and $Y_1$ and $Y_2$ are —C(W)—; in a further embodiment of this type, W is F.

In one embodiment of Formula IId, $Q_1$ is Si, $X_1$ and $X_2$ are —C(W)—, and $Y_1$ and $Y_2$ are CH; in a further embodiment of this type, W is F.

In one embodiment of Formula IId, $Q_1$ is Si, $X_1$ and $X_2$ are CH, and $Y_1$ and $Y_2$ are —C(W)—; in a further embodiment of this type, W is F.

In one embodiment of Formula IId, $Q_1$ is C, $X_1$ and $X_2$ are —C(W)—, $Y_1$ and $Y_2$ are CH, and n is 1; in a further embodiment of this type, W is F.

In one embodiment of Formula IId, $Q_1$ is C, $X_1$ and $X_2$ are CH, $Y_1$ and $Y_2$ are —C(W)—, and n is 1; in a further embodiment of this type, W is F.

In one embodiment of Formula IId, $Q_1$ is Si, $X_1$ and $X_2$ are —C(W)—, $Y_1$ and $Y_2$ are CH, and n is 1; in a further embodiment of this type, W is F.

In one embodiment of Formula IId, $Q_1$ is Si, $X_1$ and $X_2$ are CH, $Y_1$ and $Y_2$ are —C(W)—, and n is 1; in a further embodiment of this type, W is F.

In one embodiment of Formula IId, $Q_1$ is C, $X_1$ and $X_2$ are —C(W)—, $Y_1$ and $Y_2$ are CH, n is 1, and $R_7$ is n-hexyl; in a further embodiment of this type, W is F.

In one embodiment of Formula IId, $Q_1$ is C, $X_1$ and $X_2$ are CH, $Y_1$ and $Y_2$ are —C(W)—, n is 1, and $R_7$ is n-hexyl; in a further embodiment of this type, W is F.

In one embodiment of Formula IId, $Q_1$ is Si, $X_1$ and $X_2$ are —C(W)—, $Y_1$ and $Y_2$ are CH, n is 1, and $R_7$ is n-hexyl; in a further embodiment of this type, W is F.

In one embodiment of Formula IId, $Q_1$ is Si, $X_1$ and $X_2$ are CH, $Y_1$ and $Y_2$ are —C(W)—, n is 1, and $R_7$ is n-hexyl; in a further embodiment of this type, W is F.

In one embodiment of Formula IId, $Q_1$ is C, $X_1$ and $X_2$ are —C(W)—, $Y_1$ and $Y_2$ are CH, n is 1, and $R_8$ is 2-ethyl-hexyl; in a further embodiment of this type, W is F.

In one embodiment of Formula IId, $Q_1$ is C, $X_1$ and $X_2$ are CH, $Y_1$ and $Y_2$ are —C(W)—, n is 1, and $R_8$ is 2-ethyl-hexyl; in a further embodiment of this type, W is F.

In one embodiment of Formula IId, $Q_1$ is Si, $X_1$ and $X_2$ are —C(W)—, $Y_1$ and $Y_2$ are CH, n is 1, and $R_8$ is 2-ethyl-hexyl; in a further embodiment of this type, W is F.

In one embodiment of Formula IId, $Q_1$ is Si, $X_1$ and $X_2$ are CH, $Y_1$ and $Y_2$ are —C(W)—, n is 1, and $R_8$ is 2-ethyl-hexyl; in a further embodiment of this type, W is F.

In one embodiment of Formula IId, $Q_1$ is C, $X_1$ and $X_2$ are —C(W)—, $Y_1$ and $Y_2$ are CH, and n is 2; in a further embodiment of this type, W is F.

In one embodiment of Formula IId, $Q_1$ is C, $X_1$ and $X_2$ are CH, $Y_1$ and $Y_2$ are —C(W)—, and n is 2; in a further embodiment of this type, W is F.

In one embodiment of Formula IId, $Q_1$ is Si, $X_1$ and $X_2$ are —C(W)—, $Y_1$ and $Y_2$ are CH, and n is 2; in a further embodiment of this type, W is F.

In one embodiment of Formula IId, $Q_1$ is Si, $X_1$ and $X_2$ are CH, $Y_1$ and $Y_2$ are —C(W)—, and n is 2; in a further embodiment of this type, W is F.

In one embodiment of Formula IId, $Q_1$ is C, $X_1$ and $X_2$ are —C(W)—, $Y_1$ and $Y_2$ are CH, n is 2, and $R_7$ is n-hexyl; in a further embodiment of this type, W is F.

In one embodiment of Formula IId, $Q_1$ is C, $X_1$ and $X_2$ are CH, $Y_1$ and $Y_2$ are —C(W)—, n is 2, and $R_7$ is n-hexyl; in a further embodiment of this type, W is F.

In one embodiment of Formula IId, $Q_1$ is Si, $X_1$ and $X_2$ are —C(W)—, $Y_1$ and $Y_2$ are CH, n is 2, and $R_7$ is n-hexyl; in a further embodiment of this type, W is F.

In one embodiment of Formula IId, $Q_1$ is Si, $X_1$ and $X_2$ are CH, $Y_1$ and $Y_2$ are —C(W)—, n is 2, and $R_7$ is n-hexyl; in a further embodiment of this type, W is F.

In one embodiment of Formula IId, $Q_1$ is C, $X_1$ and $X_2$ are —C(W)—, $Y_1$ and $Y_2$ are CH, n is 2, and $R_8$ is 2-ethyl-hexyl; in a further embodiment of this type, W is F.

In one embodiment of Formula IId, $Q_1$ is C, $X_1$ and $X_2$ are CH, $Y_1$ and $Y_2$ are —C(W)—, n is 2, and $R_8$ is 2-ethyl-hexyl; in a further embodiment of this type, W is F.

In one embodiment of Formula IId, $Q_1$ is Si, $X_1$ and $X_2$ are —C(W)—, $Y_1$ and $Y_2$ are CH, n is 2, and $R_8$ is 2-ethyl-hexyl; in a further embodiment of this type, W is F.

In one embodiment of Formula IId, $Q_1$ is Si, $X_1$ and $X_2$ are CH, $Y_1$ and $Y_2$ are —C(W)—, n is 2, and $R_8$ is 2-ethyl-hexyl; in a further embodiment of this type, W is F.

In one embodiment of Formula IId, $Q_1$ is C, $X_1$ and $X_2$ are —C(W)—, $Y_1$ and $Y_2$ are CH, and n is 3; in a further embodiment of this type, W is F.

In one embodiment of Formula IId, $Q_1$ is C, $X_1$ and $X_2$ are CH, $Y_1$ and $Y_2$ are —C(W)—, and n is 3; in a further embodiment of this type, W is F.

In one embodiment of Formula IId, $Q_1$ is Si, $X_1$ and $X_2$ are —C(W)—, $Y_1$ and $Y_2$ are CH, and n is 3; in a further embodiment of this type, W is F.

In one embodiment of Formula IId, $Q_1$ is Si, $X_1$ and $X_2$ are CH, $Y_1$ and $Y_2$ are —C(W)—, and n is 3; in a further embodiment of this type, W is F.

In one embodiment of Formula IId, $Q_1$ is C, $X_1$ and $X_2$ are —C(W)—, $Y_1$ and $Y_2$ are CH, n is 3, and $R_7$ is n-hexyl; in a further embodiment of this type, W is F.

In one embodiment of Formula IId, $Q_1$ is C, $X_1$ and $X_2$ are CH, $Y_1$ and $Y_2$ are —C(W)—, n is 3, and $R_7$ is n-hexyl; in a further embodiment of this type, W is F.

In one embodiment of Formula IId, $Q_1$ is Si, $X_1$ and $X_2$ are —C(W)—, $Y_1$ and $Y_2$ are CH, n is 3, and $R_7$ is n-hexyl; in a further embodiment of this type, W is F.

In one embodiment of Formula IId, $Q_1$ is Si, $X_1$ and $X_2$ are CH, $Y_1$ and $Y_2$ are —C(W)—, n is 3, and $R_7$ is n-hexyl; in a further embodiment of this type, W is F.

In one embodiment of Formula IId, $Q_1$ is C, $X_1$ and $X_2$ are —C(W)—, $Y_1$ and $Y_2$ are CH, n is 3, and $R_8$ is 2-ethyl-hexyl; in a further embodiment of this type, W is F.

In one embodiment of Formula IId, $Q_1$ is C, $X_1$ and $X_2$ are CH, $Y_1$ and $Y_2$ are —C(W)—, n is 3, and $R_8$ is 2-ethyl-hexyl; in a further embodiment of this type, W is F.

In one embodiment of Formula IId, $Q_1$ is Si, $X_1$ and $X_2$ are —C(W)—, $Y_1$ and $Y_2$ are CH, n is 3, and $R_8$ is 2-ethyl-hexyl; in a further embodiment of this type, W is F.

In one embodiment of Formula IId, $Q_1$ is Si, $X_1$ and $X_2$ are CH, $Y_1$ and $Y_2$ are —C(W)—, n is 3, and $R_8$ is 2-ethyl-hexyl; in a further embodiment of this type, W is F.

In one embodiment of Formula IId, $Q_1$ is C, $X_1$ and $X_2$ are —C(W)—, $Y_1$ and $Y_2$ are CH, n is 3, and $R_8$ is n-hexyl; in a further embodiment of this type, W is F.

In one embodiment of Formula IId, $Q_1$ is C, $X_1$ and $X_2$ are CH, $Y_1$ and $Y_2$ are —C(W)—, n is 3, and $R_8$ is n-hexyl; in a further embodiment of this type, W is F.

In one embodiment of Formula IId, $Q_1$ is Si, $X_1$ and $X_2$ are —C(W)—, $Y_1$ and $Y_2$ are CH, n is 3, and $R_8$ is n-hexyl; in a further embodiment of this type, W is F.

In one embodiment of Formula IId, $Q_1$ is Si, $X_1$ and $X_2$ are CH, $Y_1$ and $Y_2$ are —C(W)—, n is 3, and $R_8$ is n-hexyl; in a further embodiment of this type, W is F.

In one embodiment of Formula IId, the compound is of the formula:

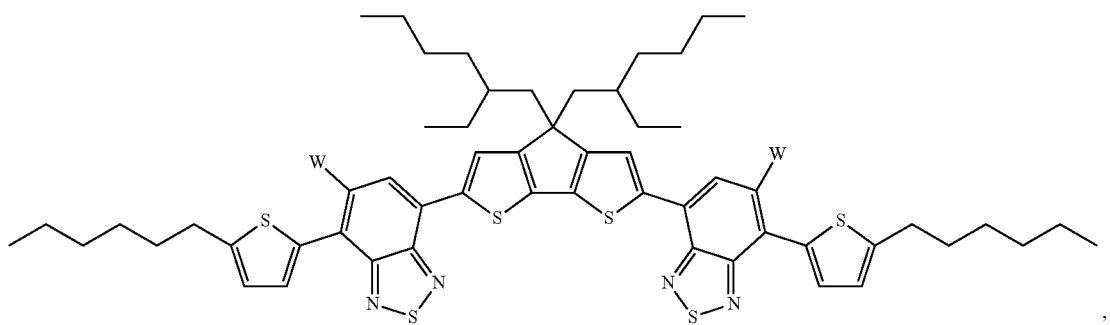

,

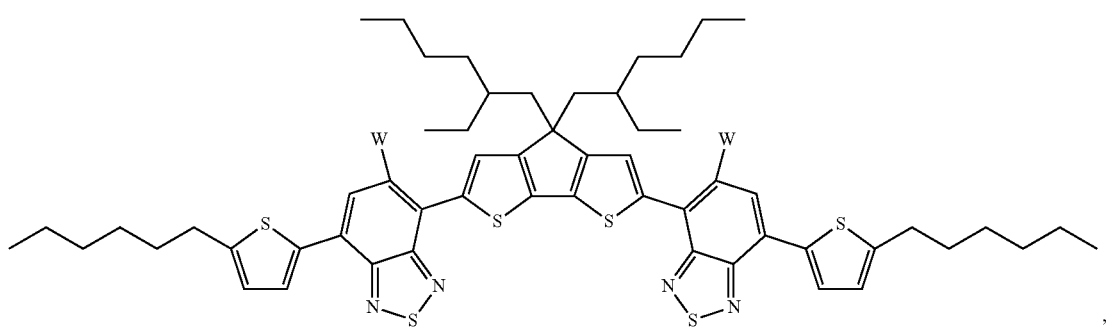

,

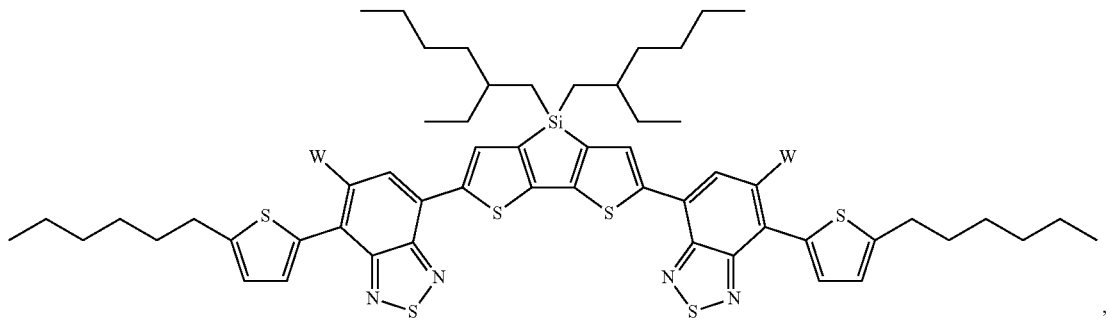

,

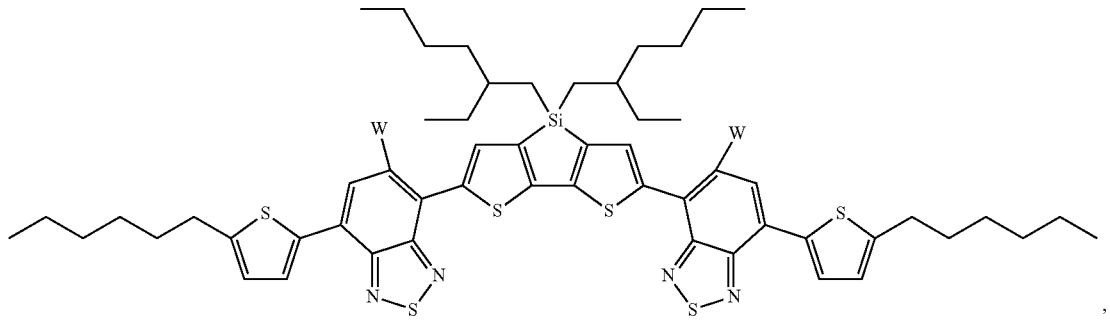

,

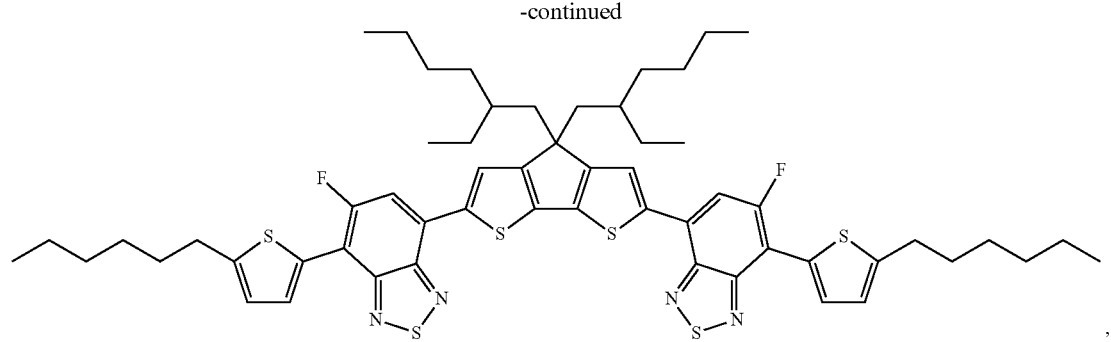
,
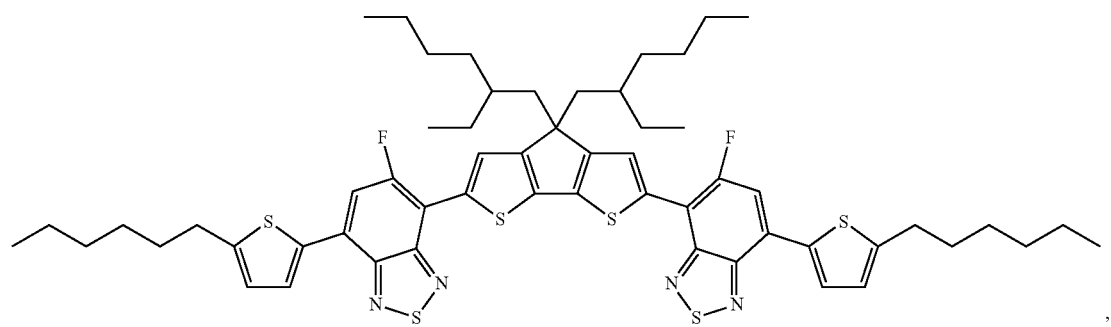
,
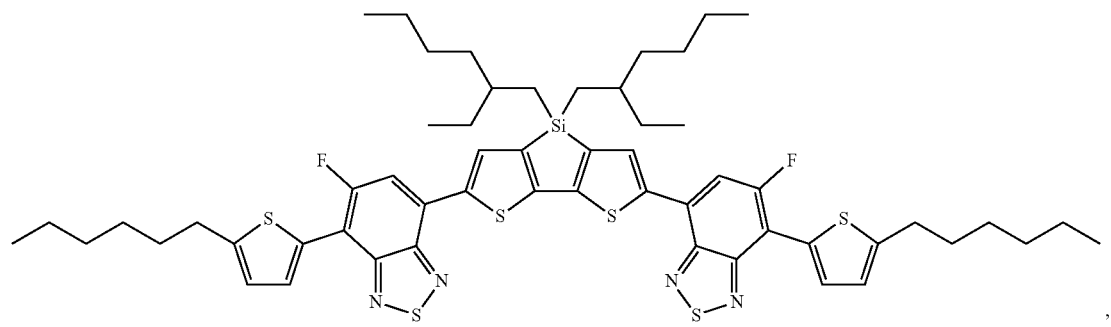
,
or
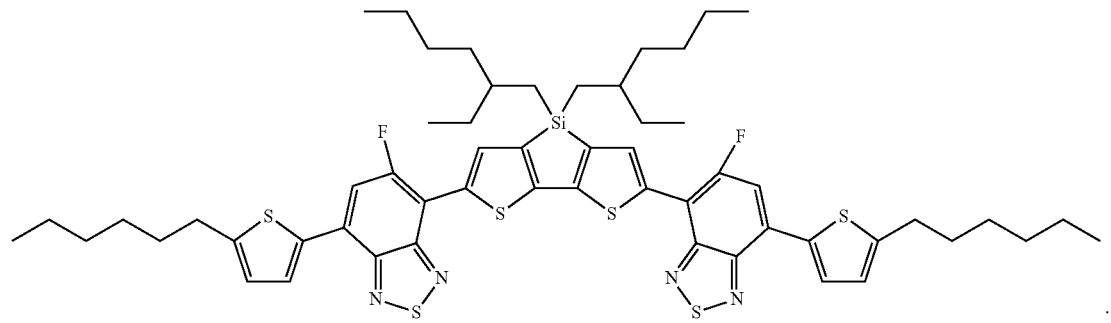
.

In one embodiment of Formula IId, the compound is of the formula:
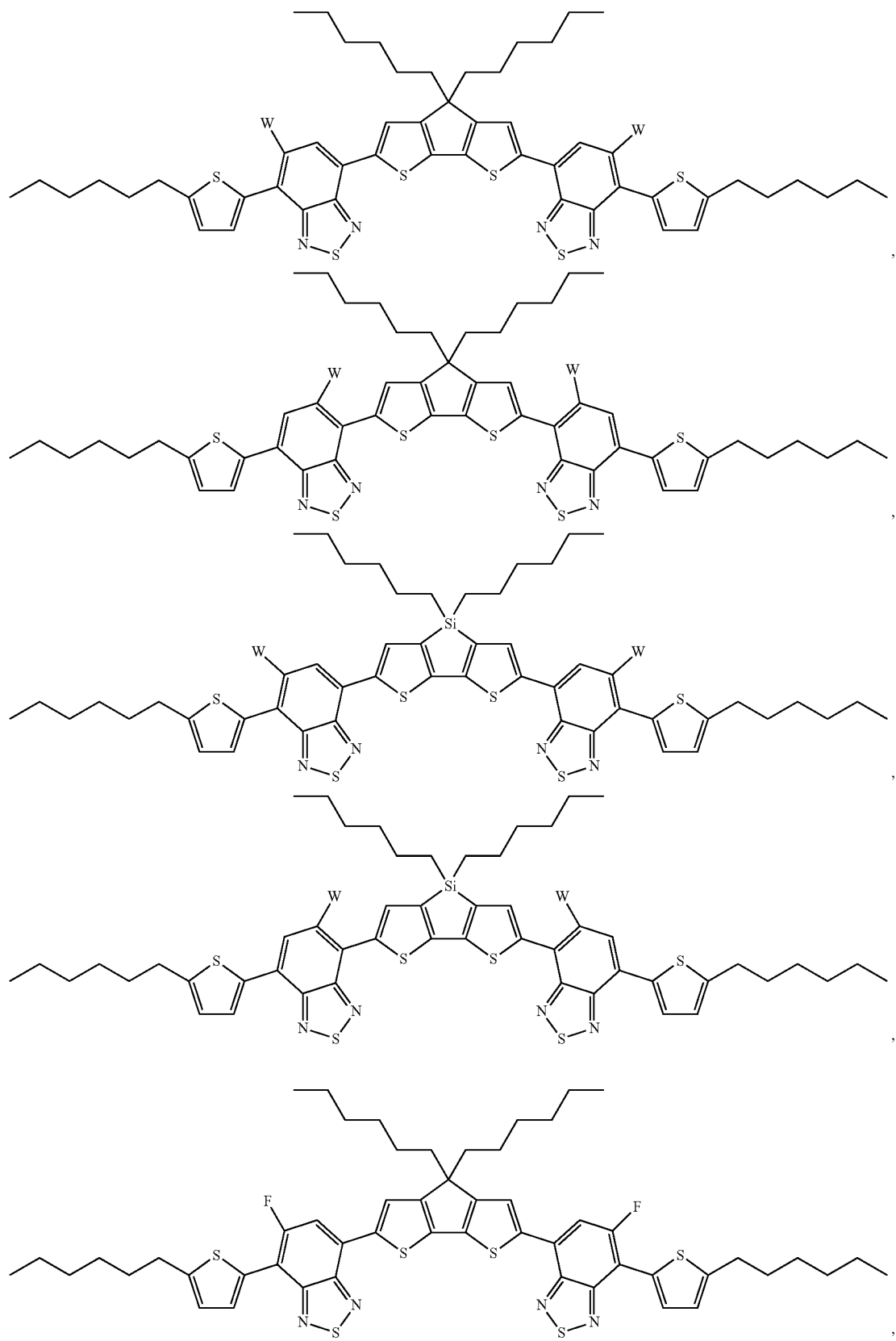

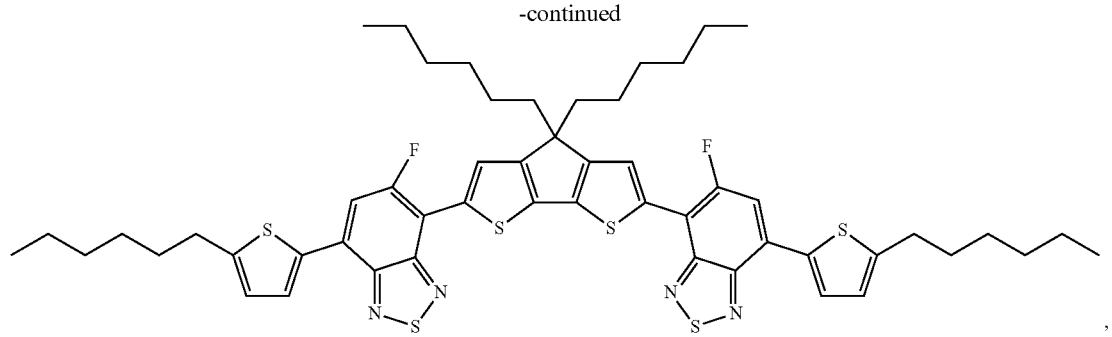
,
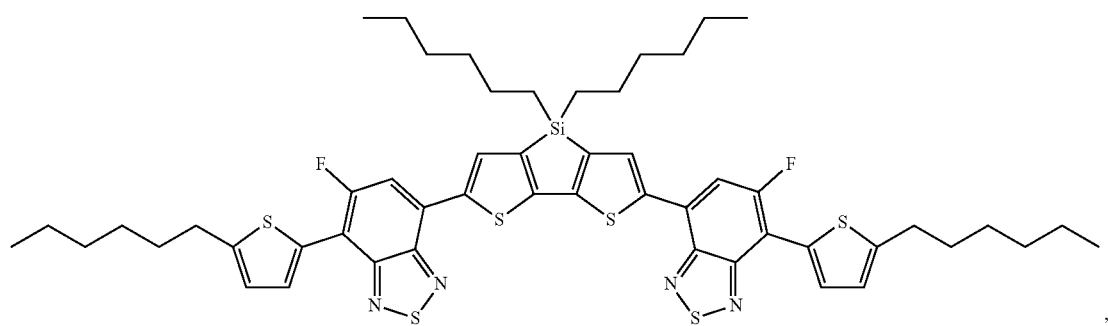
,
or
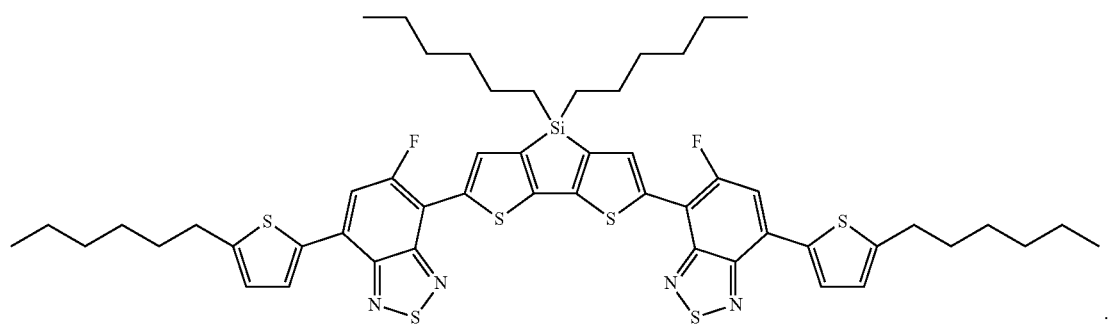
.
In one embodiment of Formula IId, the compound is of the formula:
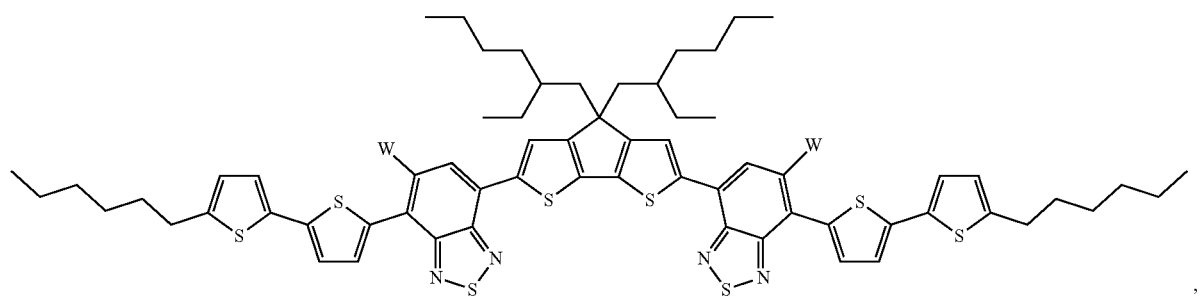
, -continued
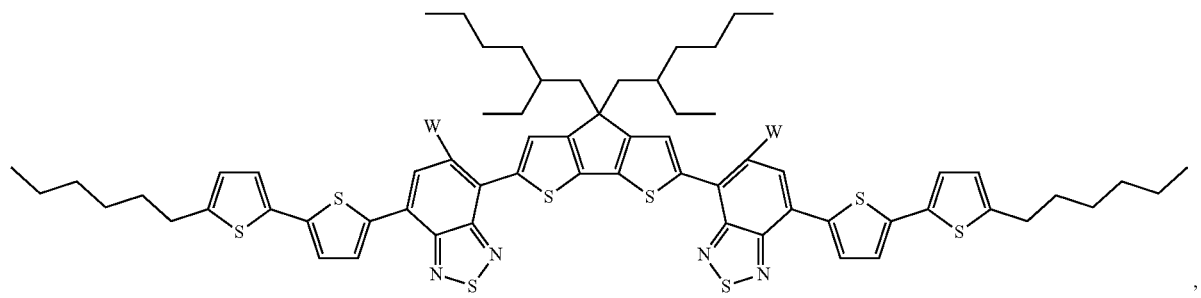
,
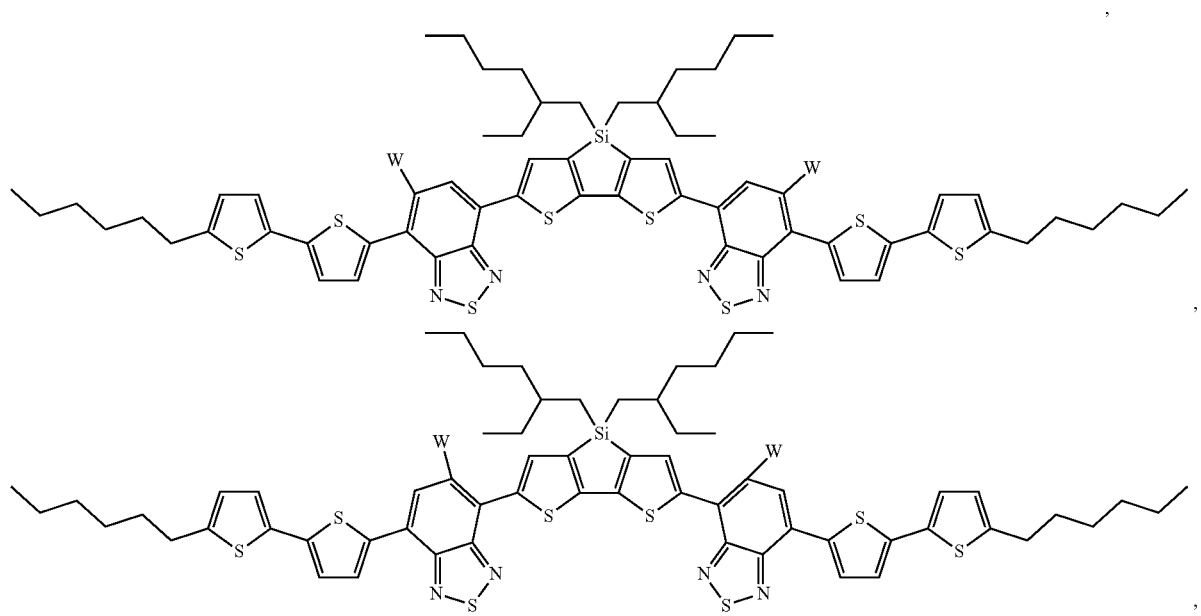
,
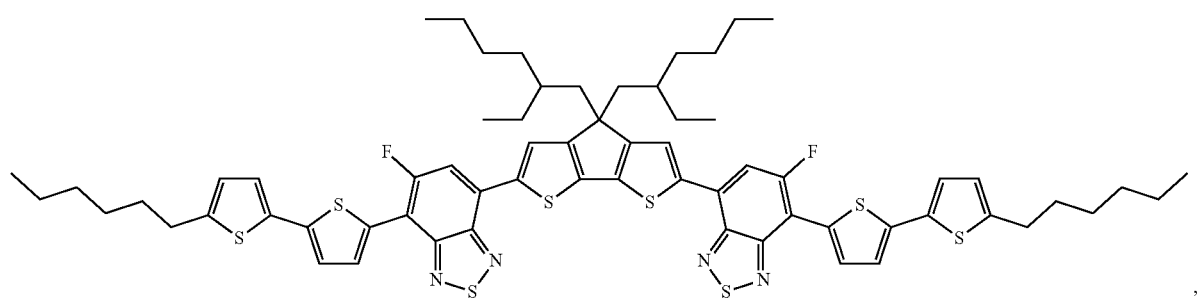
,
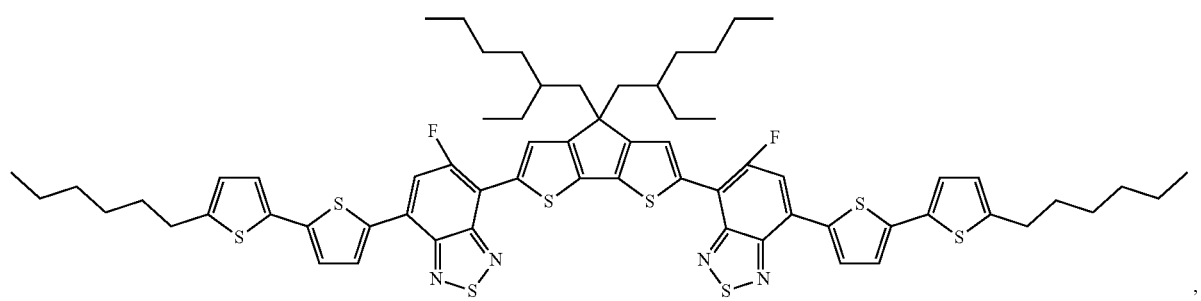
, -continued
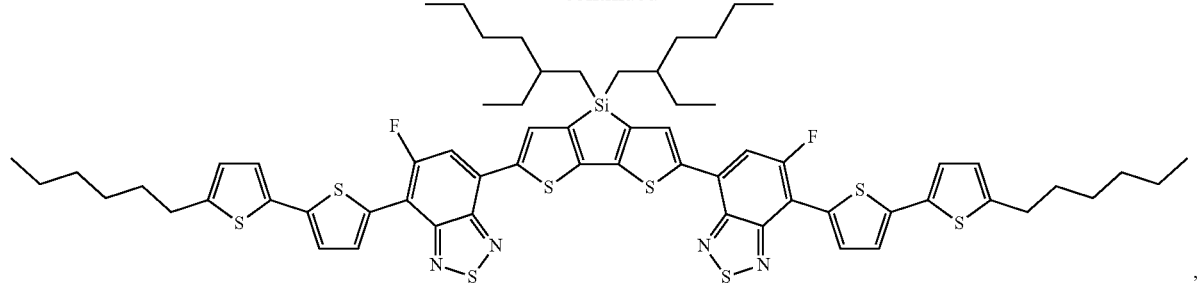
or
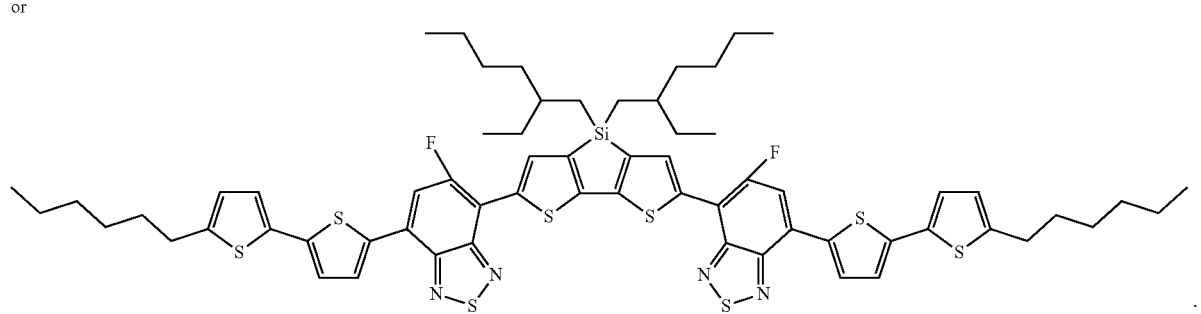
In one embodiment of Formula IId, the compound is of the formula:
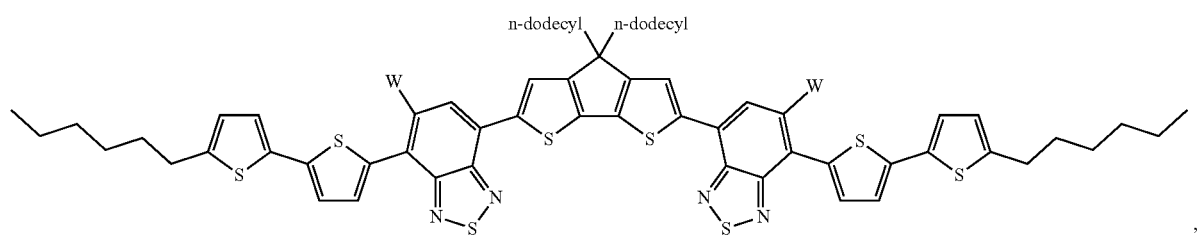
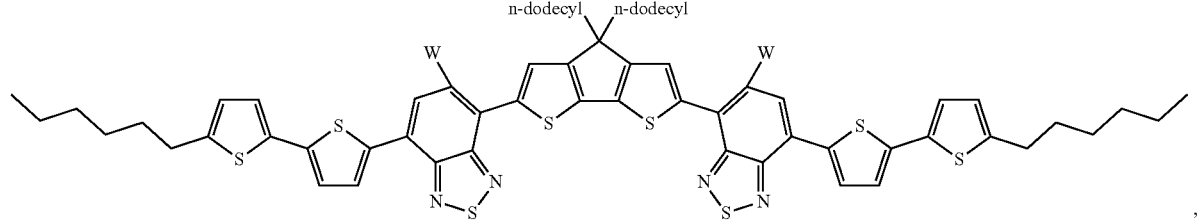
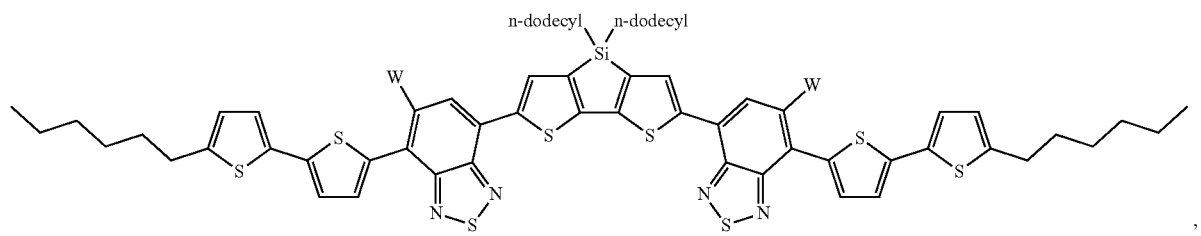
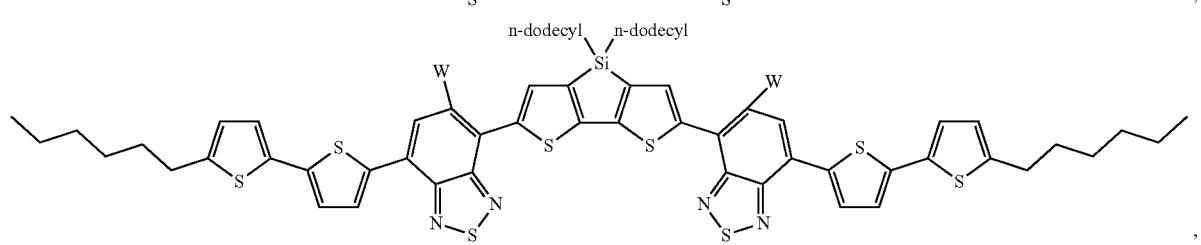

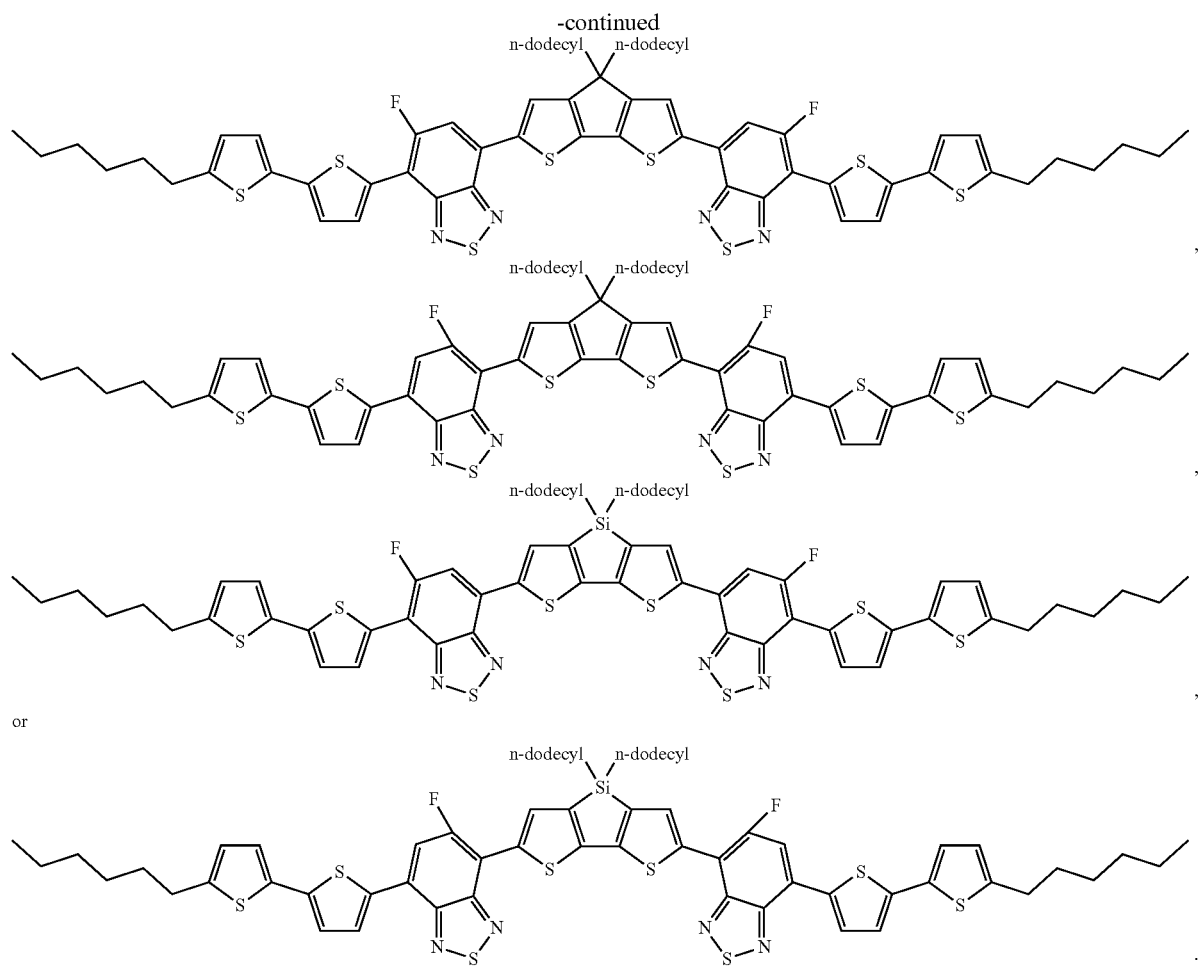
In one embodiment of Formula IId, the compound is of the formula:
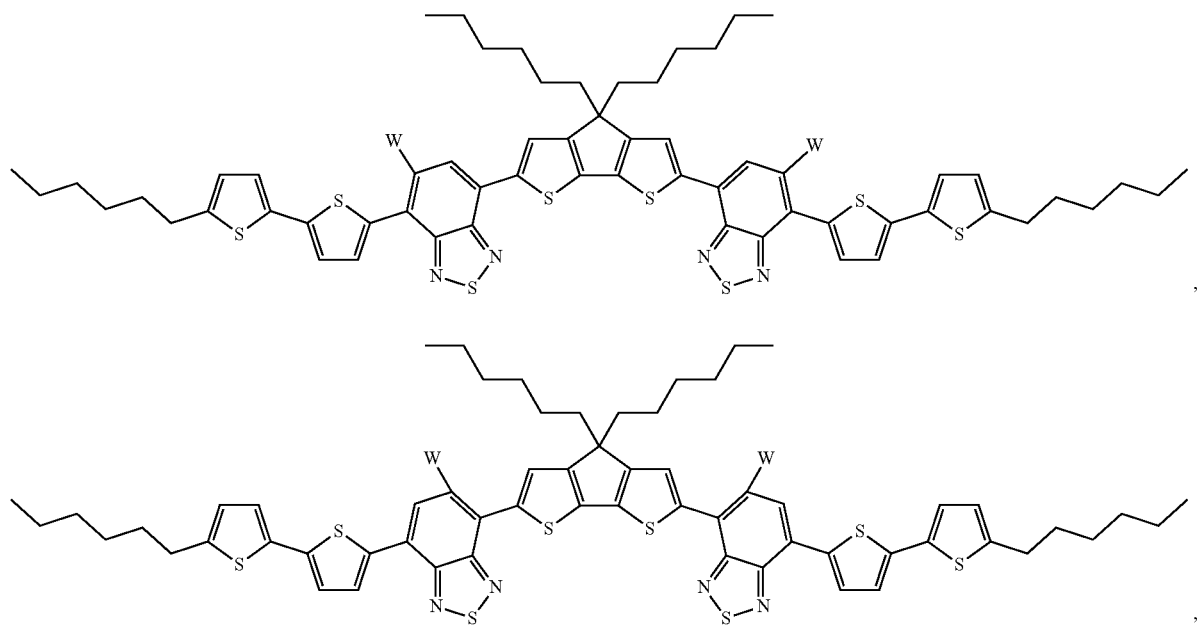

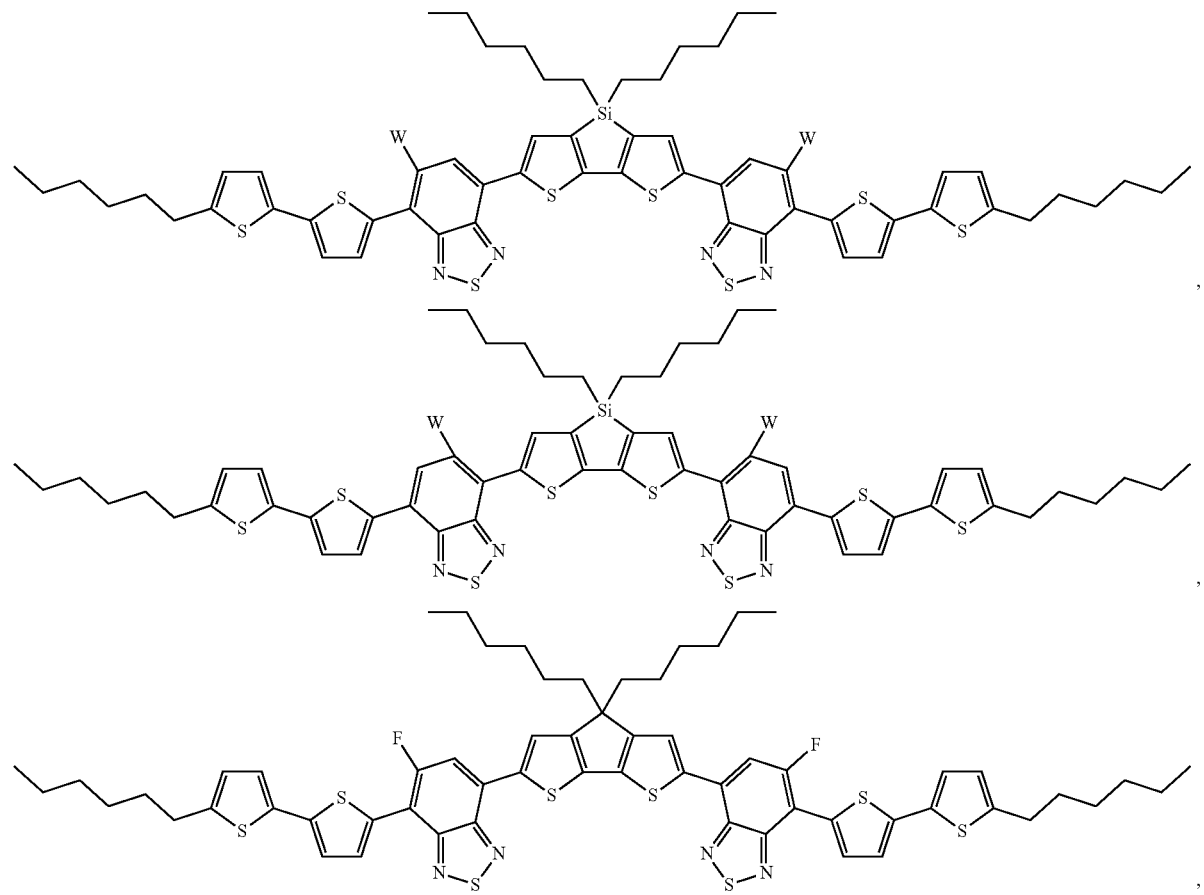
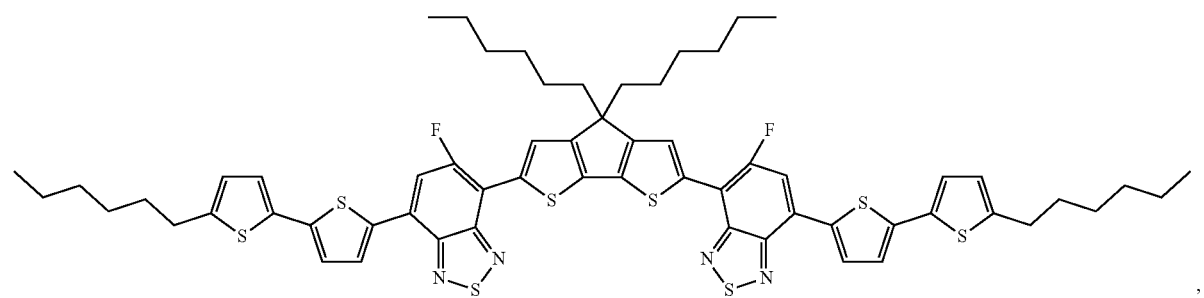
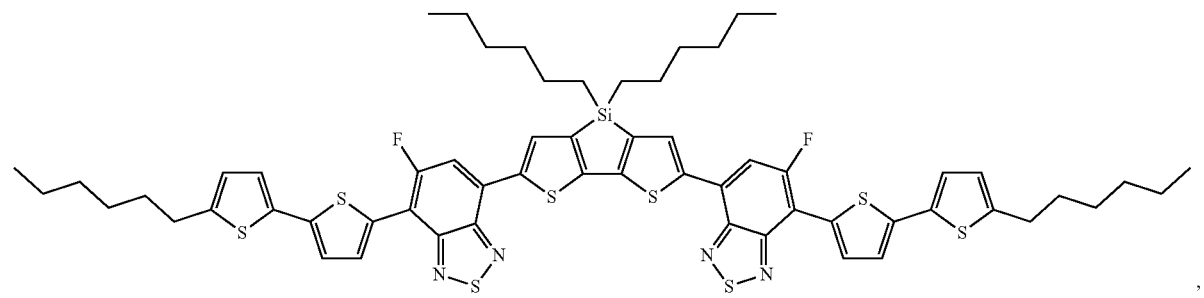

or
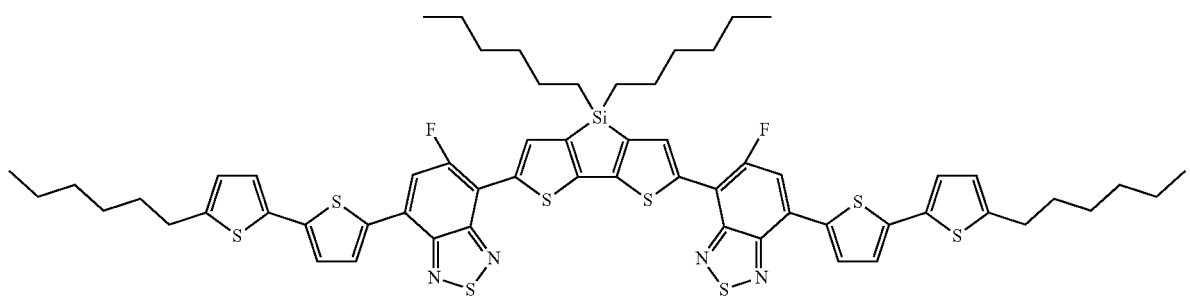
In one embodiment of Formula IId, the compound is of the formula:
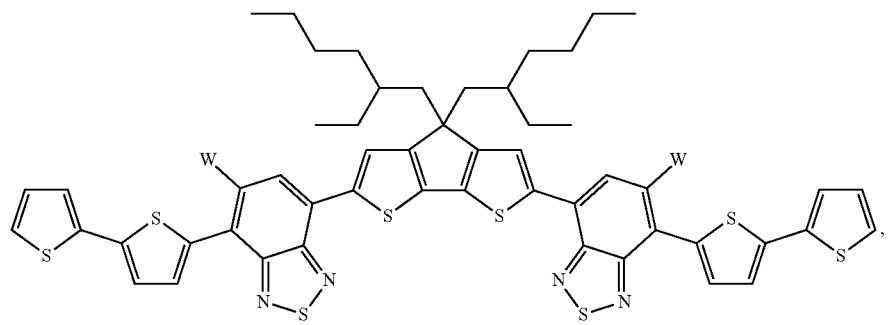
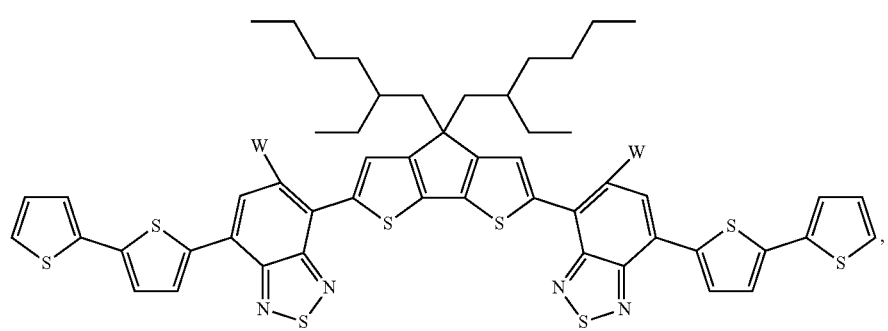
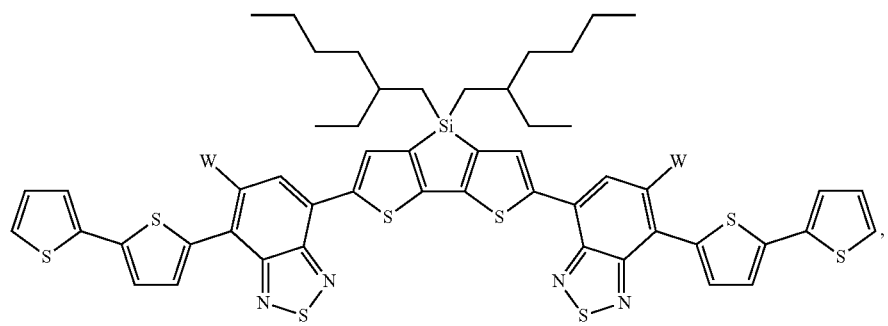

-continued
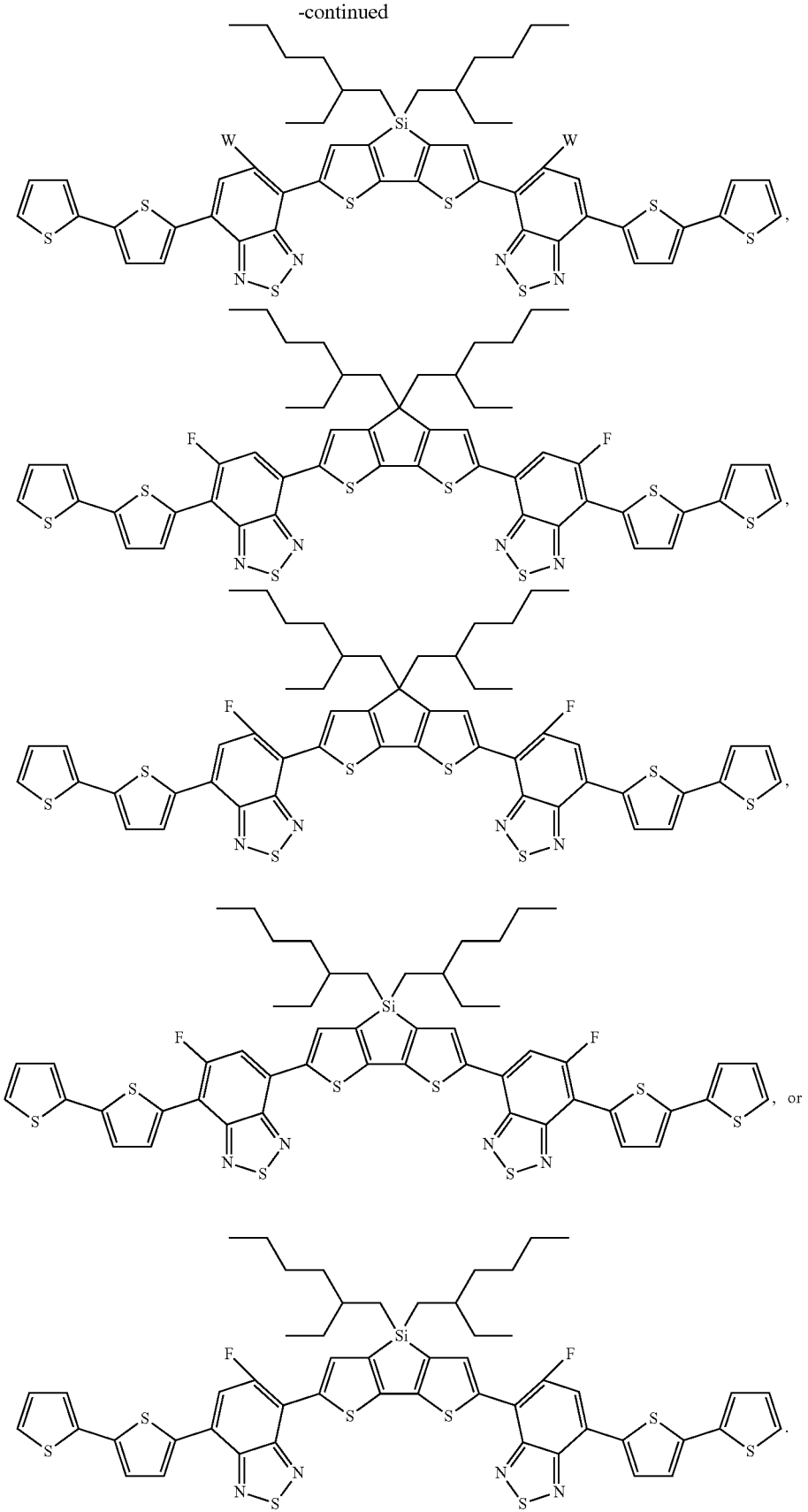

In one embodiment of Formula IId, the compound is of the formula:
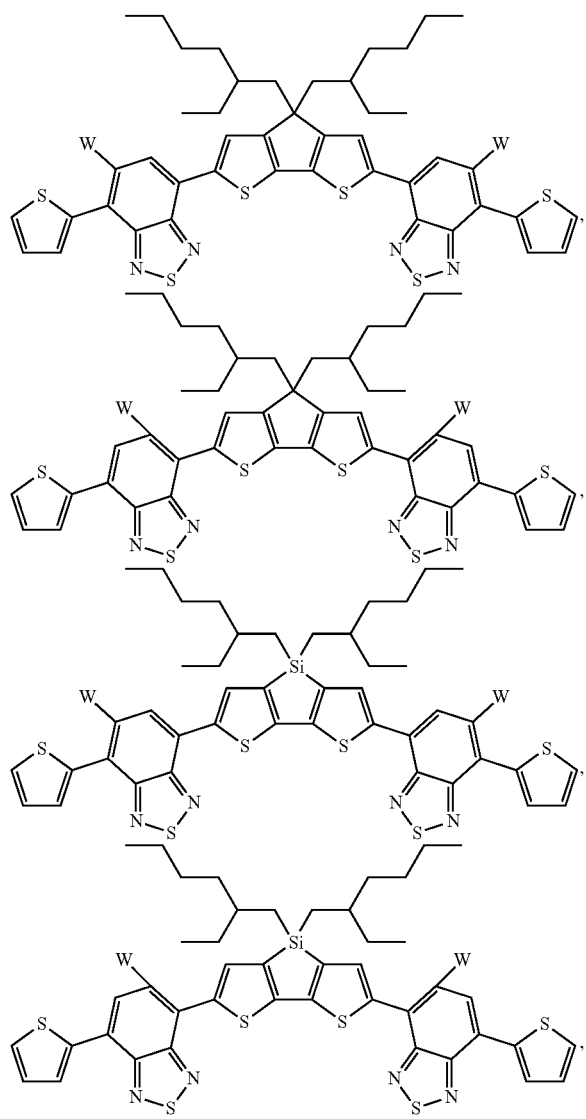
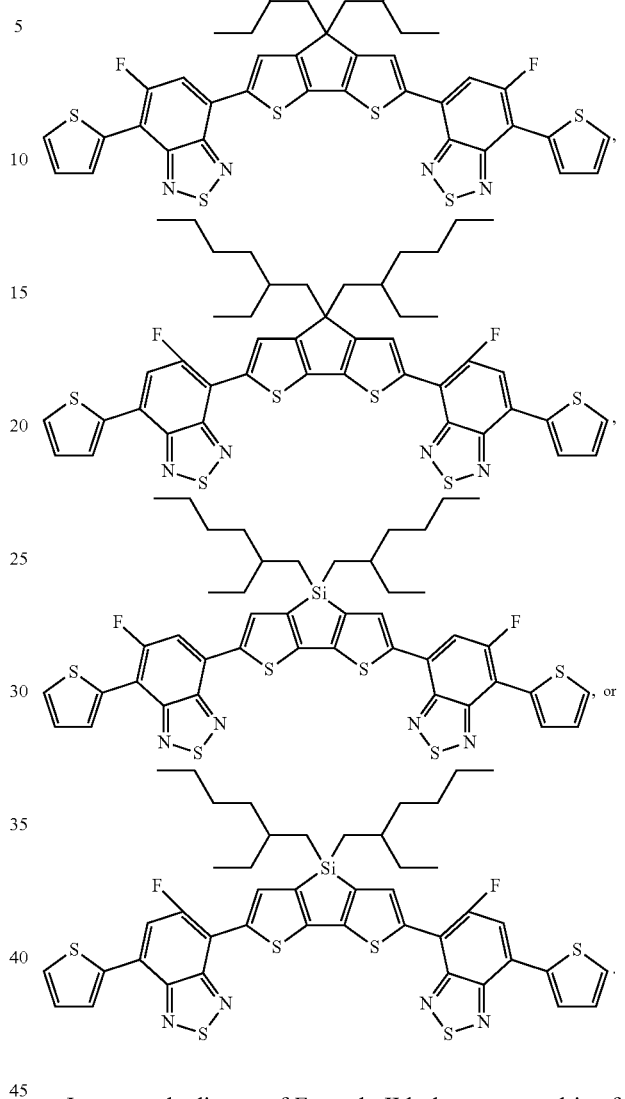
In one embodiment of Formula IId, the compound is of the formula:
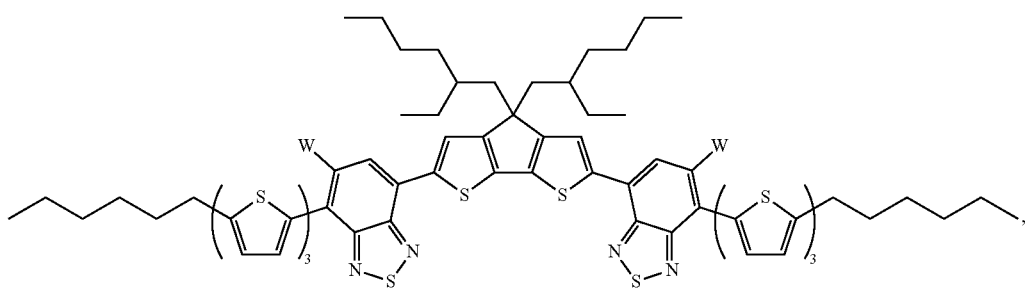

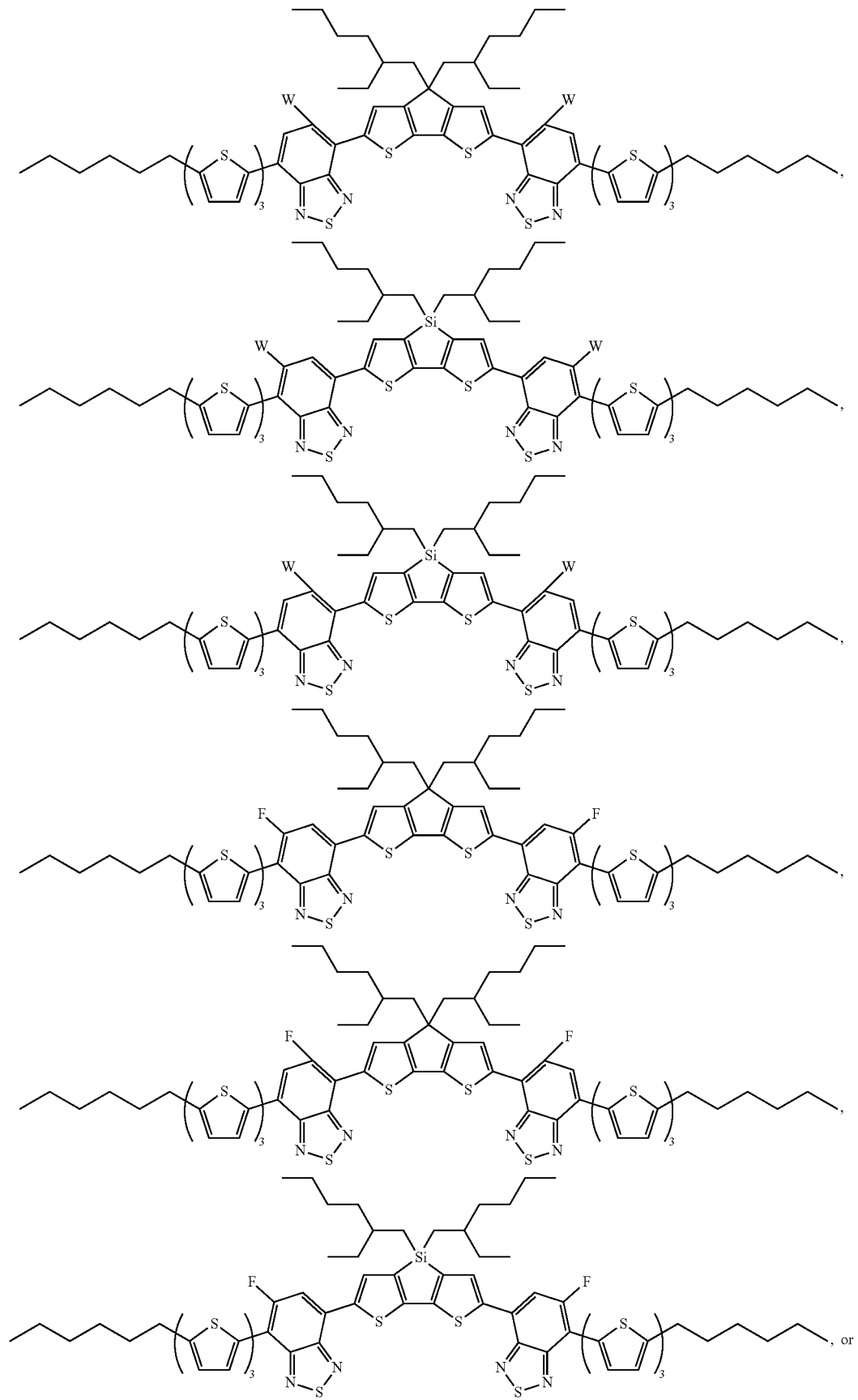

-continued
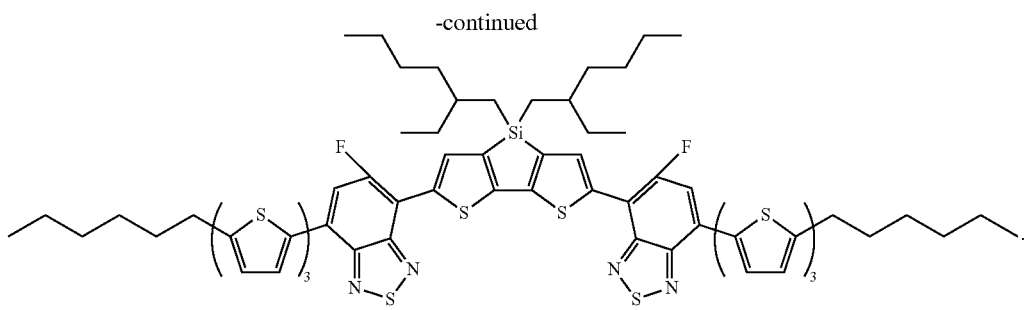
In one embodiment of Formula IId, the compound is of the formula:
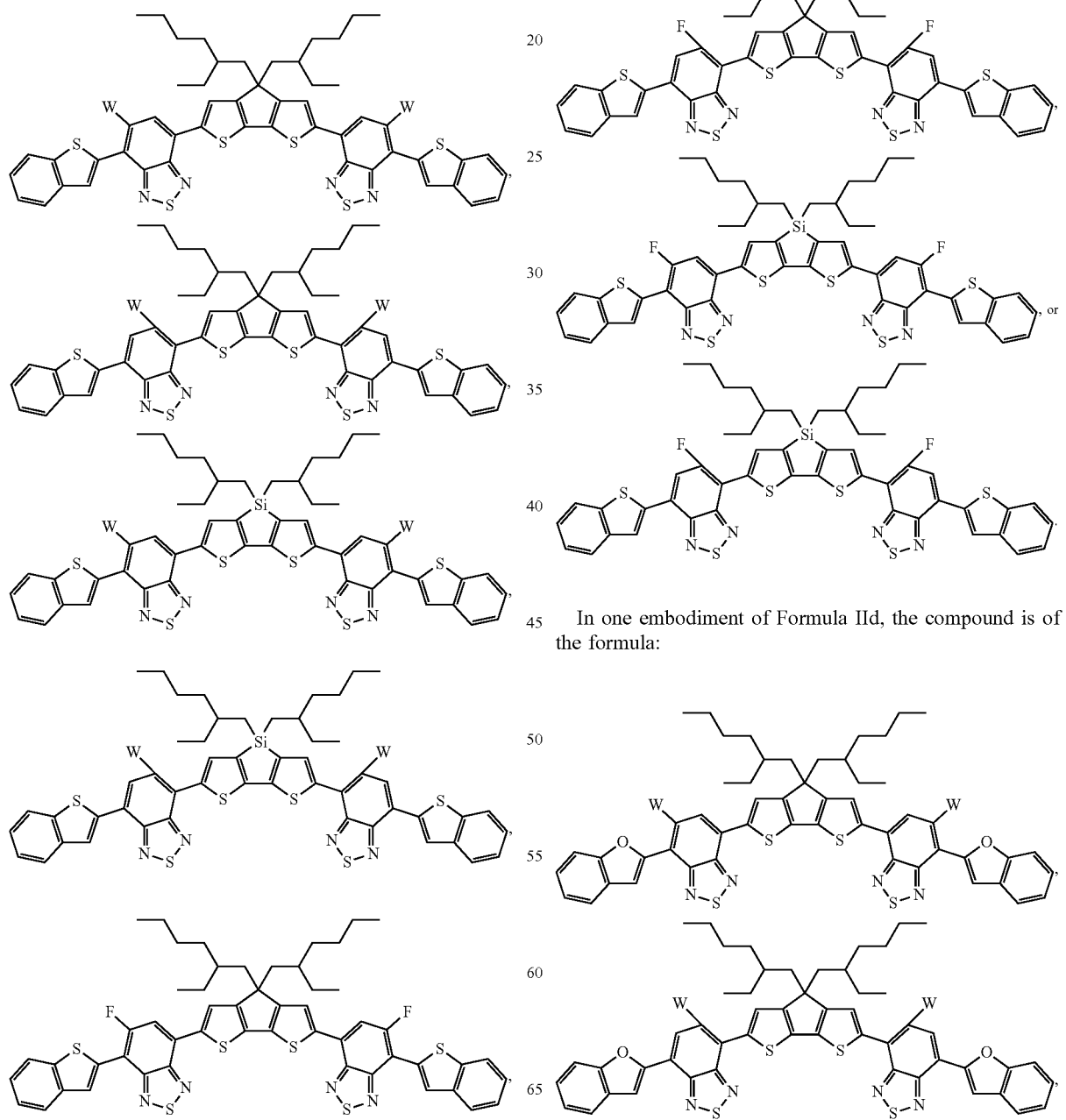
In one embodiment of Formula IId, the compound is of the formula:

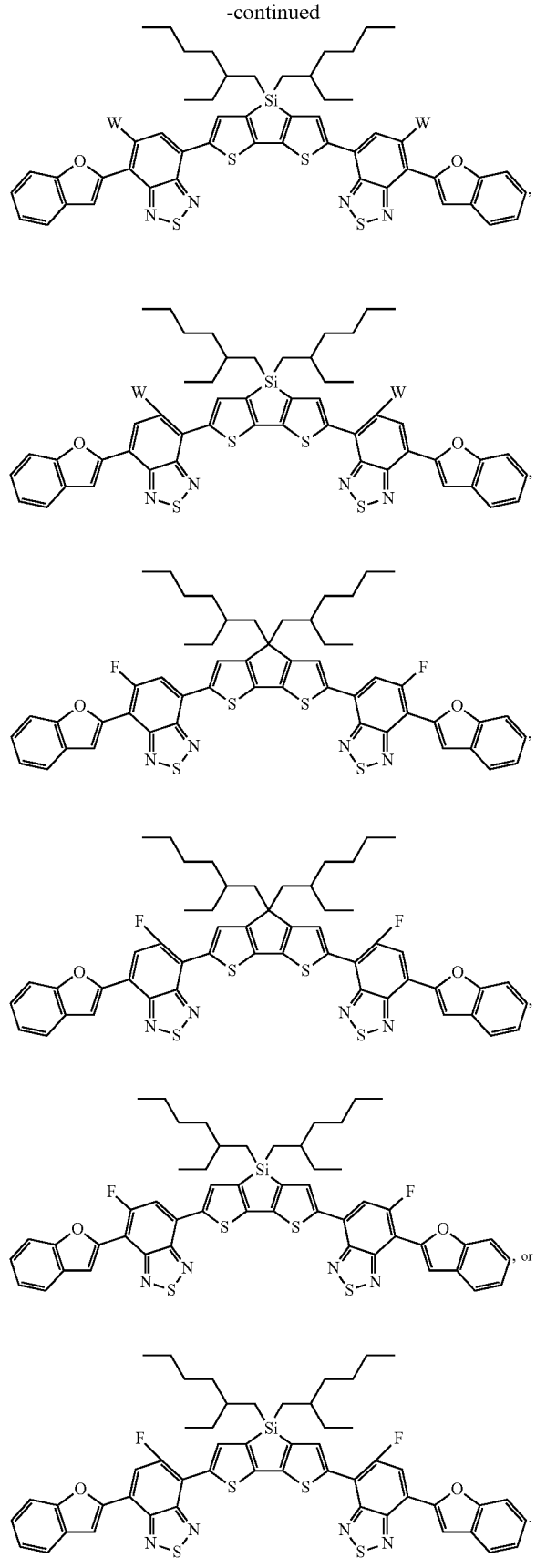
In one embodiment of Formula IId, the compound is of the formula:
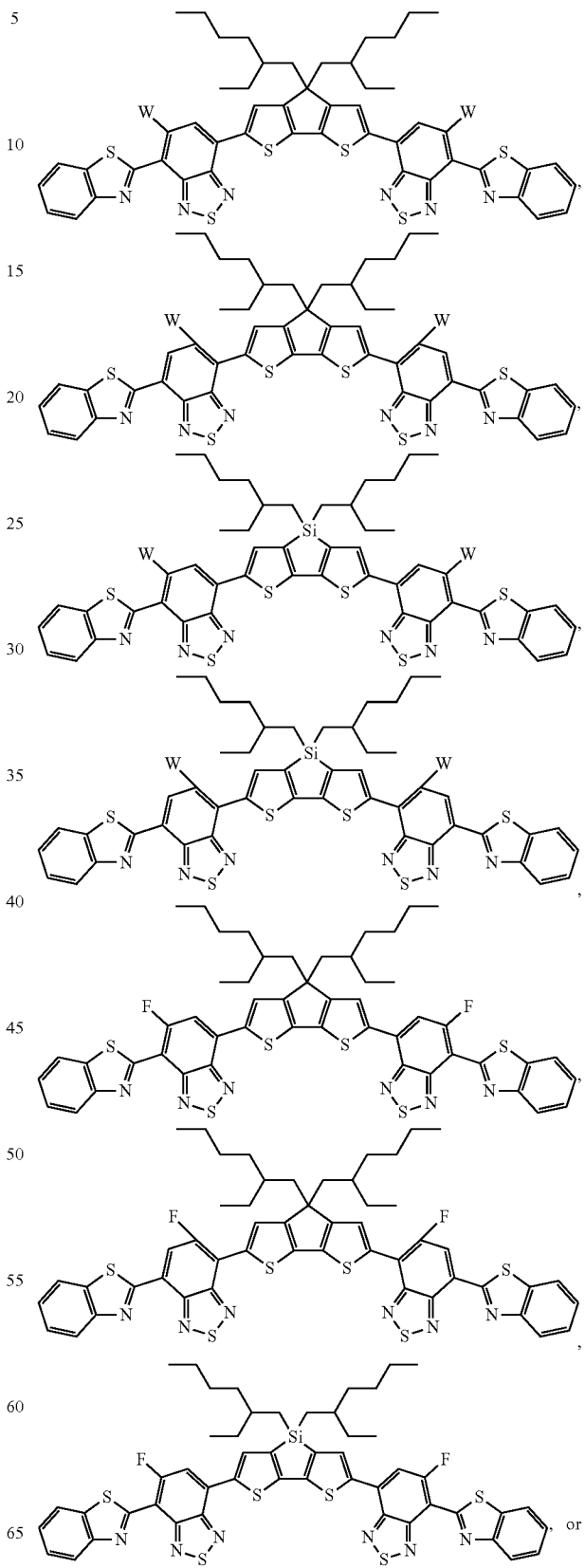

-continued

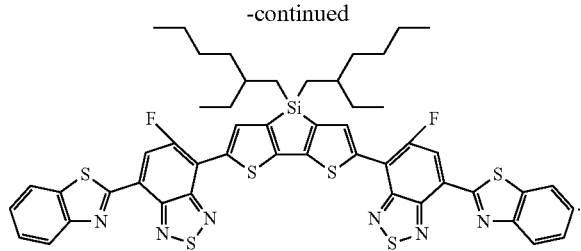

In some embodiments of Formula II, the compounds are of Formula IIe:

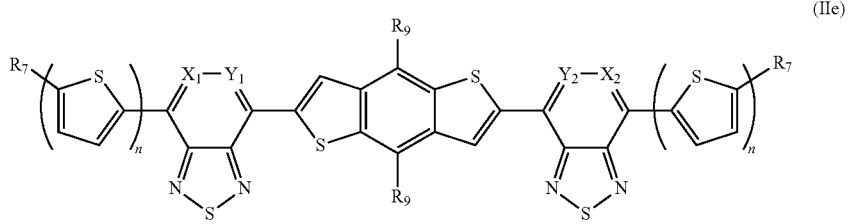

where $X_1$ and $Y_1$ are selected from —C(W)— and CH, where when $X_1$ is —C(W)—, $Y_1$ is CH, and when $X_1$ is CH, $Y_1$ is —C(W)—; and where, independently of $X_1$ and $Y_1$, $X_2$ and $Y_2$ are selected from —C(W)— and CH, where when $X_2$ is —C(W)—, $Y_2$ is CH, and when $X_2$ is CH, $Y_2$ is —C(W)—;

where W is selected from F, Cl, Br, I, —CN, —CF$_3$, —CHF$_2$, or —CH$_2$F;

n is 0, 1, 2, or 3;

$R_7$ is selected from H, $C_1$-$C_{16}$ alkyl, —O—$C_1$-$C_{16}$ alkyl, benzofuran-2-yl, benzothiophene-2-yl, benzothiazole-2-yl, 4H-cyclopenta[2,1-b;3,4-b']dithiophene-2-yl, 4,4-bis($C_1$-$C_{16}$ alkyl)-4H-cyclopenta[2,1-b;3,4-b']dithiophene-2-yl, and 4,4-bis(2-ethylhexyl)-4H-cyclopenta[2,1-b;3,4-b']dithiophene-2-yl; and $R_9$ is selected from H, $C_1$-$C_{16}$ alkyl or —O—$C_1$-$C_{16}$ alkyl. In a further embodiment of this type, W is F.

In one embodiment of Formula IIe, n is 0.
In one embodiment of Formula IIe, n is 1.
In one embodiment of Formula IIe, n is 2.
In one embodiment of Formula IIe, n is 3.
In one embodiment of Formula IIe, $X_1$ and $X_2$ are —C(W)— and $Y_1$ and $Y_2$ are CH; in a further embodiment of this type, W is F.
In one embodiment of Formula IIe, $X_1$ and $X_2$ are CH and $Y_1$ and $Y_2$ are —C(W)—; in a further embodiment of this type, W is F.
In one embodiment of Formula IIe, $R_9$ is —O—$C_1$-$C_{16}$ alkyl.
In one embodiment of Formula IIe, $R_9$ is —O—CH$_2$CH($C_2H_5$)($C_4H_9$).
In one embodiment of Formula IIe, $R_7$ is 4,4-bis(2-ethylhexyl)-4H-cyclopenta[2,1-b;3,4-b']dithiophene-2-yl.
In one embodiment of Formula IIe, $R_9$ is —O—CH$_2$CH($C_2H_5$)($C_4H_9$) and $R_7$ is 4,4-bis(2-ethylhexyl)-4H-cyclopenta[2,1-b;3,4-b']dithiophene-2-yl.
In one embodiment of Formula IIe, $R_9$ is —O—$C_1$-$C_{16}$ alkyl and n is 0.
In one embodiment of Formula IIe, $R_9$ is —O—CH$_2$CH($C_2H_5$)($C_4H_9$) and n is 0.

In one embodiment of Formula IIe, $R_7$ is 4,4-bis(2-ethylhexyl)-4H-cyclopenta[2,1-b;3,4-b']dithiophene-2-yl and n is 0.
In one embodiment of Formula IIe, $R_9$ is —O—CH$_2$CH($C_2H_5$)($C_4H_9$), $R_7$ is 4,4-bis(2-ethylhexyl)-4H-cyclopenta[2,1-b;3,4-b']dithiophene-2-yl and n is 0.
In one embodiment of Formula IIe, $R_9$ is —O—CH$_2$CH($C_2H_5$)($C_4H_9$), $R_7$ is 4,4-bis(2-ethylhexyl)-4H-cyclopenta[2,1-b;3,4-b']dithiophene-2-yl, $X_1$ and $X_2$ are —C(W)—, and $Y_1$ and $Y_2$ are CH; in a further embodiment of this type, W is F.
In one embodiment of Formula IIe, $R_9$ is —O—CH$_2$CH($C_2H_5$)($C_4H_9$), $R_7$ is 4,4-bis(2-ethylhexyl)-4H-cyclopenta[2,1-b;3,4-b']dithiophene-2-yl, $X_1$ and $X_2$ are CH, and $Y_1$ and $Y_2$ are —C(W)—; in a further embodiment of this type, W is F.
In one embodiment of Formula IIe, $R_9$ is —O—CH$_2$CH($C_2H_5$)($C_4H_9$), $R_7$ is 4,4-bis(2-ethylhexyl)-4H-cyclopenta[2,1-b;3,4-b']dithiophene-2-yl, $X_1$ and $X_2$ are —C(W)—, $Y_1$ and $Y_2$ are CH, and n is 0; in a further embodiment of this type, W is F.
In one embodiment of Formula IIe, $R_9$ is —O—CH$_2$CH($C_2H_5$)($C_4H_9$), $R_7$ is 4,4-bis(2-ethylhexyl)-4H-cyclopenta[2,1-b;3,4-b']dithiophene-2-yl, $X_1$ and $X_2$ are CH, $Y_1$ and $Y_2$ are —C(W)—, and n is 0; in a further embodiment of this type, W is F.
In one embodiment of Formula IIe, $R_7$ is n-hexyl.
In one embodiment of Formula IIe, $R_9$ is —O—$C_1$-$C_{16}$ alkyl and n is 1.
In one embodiment of Formula IIe, $R_9$ is —O—CH$_2$CH($C_2H_5$)($C_4H_9$) and n is 1.
In one embodiment of Formula IIe, $R_9$ is —O—CH$_2$CH($C_2H_5$)($C_4H_9$) and $R_7$ is n-hexyl.
In one embodiment of Formula IIe, $R_7$ is n-hexyl and n is 1.
In one embodiment of Formula IIe, $R_9$ is —O—CH$_2$CH($C_2H_5$)($C_4H_9$), $R_7$ is n-hexyl and n is 1.
In one embodiment of Formula IIe, $R_9$ is —O—CH$_2$CH($C_2H_5$)($C_4H_9$), $R_7$ is n-hexyl, $X_1$ and $X_2$ are —C(W)—, and $Y_1$ and $Y_2$ are CH; in a further embodiment of this type, W is F.
In one embodiment of Formula IIe, $R_9$ is —O—CH$_2$CH($C_2H_5$)($C_4H_9$), $R_7$ is n-hexyl, $X_1$ and $X_2$ are CH, and $Y_1$ and $Y_2$ are —C(W)—; in a further embodiment of this type, W is F.
In one embodiment of Formula IIe, $R_9$ is —O—CH$_2$CH($C_2H_5$)($C_4H_9$), $R_7$ is n-hexyl, $X_1$ and $X_2$ are —C(W)—, $Y_1$ and $Y_2$ are CH, and n is 1; in a further embodiment of this type, W is F.
In one embodiment of Formula IIe, $R_9$ is —O—CH$_2$CH($C_2H_5$)($C_4H_9$), $R_7$ is n-hexyl, $X_1$ and $X_2$ are CH, $Y_1$ and $Y_2$ are —C(W)—, and n is 1; in a further embodiment of this type, W is F.

In some embodiments, the compounds of Formula II embrace compounds of Formula IIf:

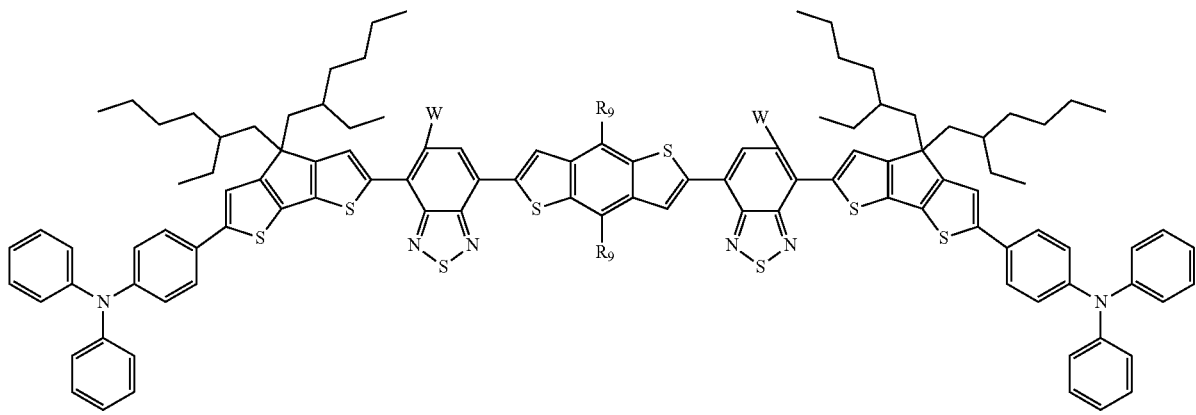

(IIf)

where $R_9$ is H, $C_1$-$C_{16}$ alkyl or —O—$C_1$-$C_{16}$ alkyl, and where W is selected from F, Cl, Br, I, —CN, —$CF_3$, —$CHF_2$, or —$CH_2F$. In a further embodiment, W is F.

In one embodiment of Formula IIf, $R_9$ is —O—$CH_2$CH($C_2H_5$)($C_4H_9$).

In one embodiment of Formula IIf, $R_9$ is —O—$(CH_2)_5CH_3$.

In another embodiment, the invention embraces compounds of Formula III:

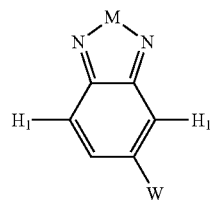

III where M is selected from sulfur (S), oxygen (O), or N—$R_1$, where $R_1$ is H, $C_1$-$C_{30}$ alkyl or $C_6$-$C_{30}$ aryl;

where W is selected from F, Cl, Br, I, —CN, —$CF_3$, —$CHF_2$, or —$CH_2F$; in a further embodiment, W is F (Formula III-F);

where $H_1$ is selected from $A_1$, —$B_1$-$B_2$, -$A_1$-$B_1$-$B_2$, or

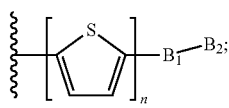

n is an integer between 0 and 5, inclusive;

$A_1$ (when present) is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, dithienopyrrole, dithienophosphole and carbazole 9,9-RR'-9H-fluorene, 9-R-9H-carbazole, 3,3'-RR'silylene-2,2'-bithiophene, 3,3'RR'-cyclopenta[2,1-b:3,4-b']-dithiophene, where R and R'=$C_1$-$C_{30}$ alkyl or $C_6$-$C_{30}$ aryl;

each $B_1$ (when present) is independently selected from substituted or unsubstituted aryl or heteroaryl groups such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, and carbazole; and each $B_2$ (when present) is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups.

In one embodiment, n is an integer between 0 and 5, inclusive. In another embodiment, n is 0. In another embodiment, n is 1. In another embodiment, n is 2. In another embodiment, n is 3. In another embodiment, n is 4. In another embodiment, n is 5.

In another embodiment, the invention embraces compounds of Formula III of Formula IIIa, Formula IIIb, Formula IIIc, and Formula IIId:

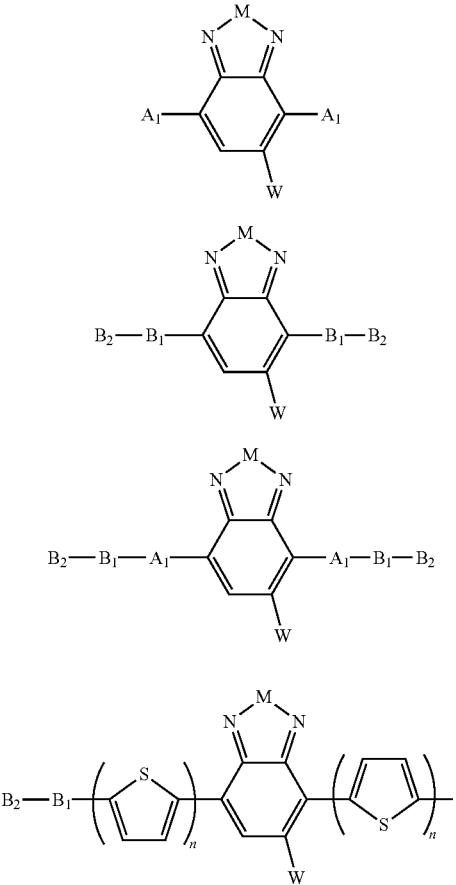

(IIIa)
(IIIb)
(IIIc)
(IIId)

where M is selected from sulfur (S), oxygen (O), or N—$R_1$, where $R_1$ is H, $C_1$-$C_{30}$ alkyl or $C_6$-$C_{30}$ aryl;

where W is selected from F, Cl, Br, I, —CN, —$CF_3$, —$CHF_2$, or —$CH_2F$; in a further embodiment, W is F (Formula IIIa-F, Formula IIIb-F, Formula IIIc-F, or Formula IIId-F);

n is an integer between 0 and 5, inclusive;

$A_1$ (when present) is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, dithienopyrrole, dithienophosphole and carbazole 9,9-RR'-9H-fluorene, 9-R-9H-carbazole, 3,3'-RR'silylene-2,2'-bithiophene, 3,3'RR'-cyclopenta[2,1-b:3,4-b']-dithiophene, where R and R'=$C_1$-$C_{30}$ alkyl or $C_6$-$C_{30}$ aryl;

each $B_1$ (when present) is independently selected from substituted or unsubstituted aryl or heteroaryl groups such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, and carbazole; and each $B_2$ (when present) is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups.

In one embodiment, n is an integer between 0 and 5, inclusive. In another embodiment, n is 0. In another embodiment, n is 1. In another embodiment, n is 2. In another embodiment, n is 3. In another embodiment, n is 4. In another embodiment, n is 5.

In another embodiment, the invention embraces compounds of Formula IV-V:

IV-V

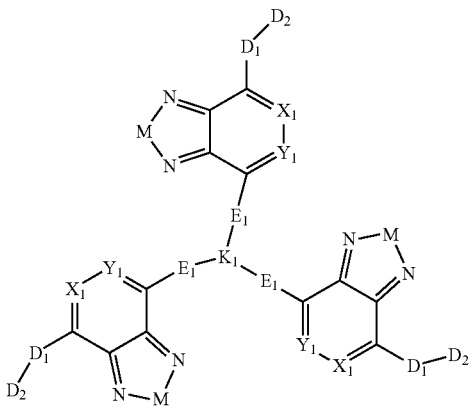

where $X_1$ and $Y_1$ are selected from —C(W)— and CH, where when $X_1$ is —C(W)—, $Y_1$ is CH, and when $X_1$ is CH, $Y_1$ is —C(W)—; and where, independently of $X_1$ and $Y_1$, $X_2$ and $Y_2$ are selected from —C(W)— and CH, where when $X_2$ is —C(W)—, $Y_2$ is CH, and when $X_2$ is CH, $Y_2$ is —C(W)—; and where, independently of $X_1$, $Y_1$, $X_2$, and $Y_2$, $X_3$ and $Y_3$ are selected from —C(W)— and CH, where when $X_3$ is —C(W)—, $Y_3$ is CH, and when $X_3$ is CH, $Y_3$ is —C(W)—;

where W is selected from F, Cl, Br, I, —CN, —$CF_3$, —$CHF_2$, or —$CH_2F$; in a further embodiment, W is F;

M is selected from sulfur (S), oxygen (O), or N—$R_1$, where $R_1$ is H, $C_1$-$C_{30}$ alkyl or $C_6$-$C_{30}$ aryl;

$K_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups.

Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole;

each $E_1$ is independently either absent, or selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole;

each $D_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole; and each $D_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole.

In one embodiment of Formula IV-V, each M is S. In one embodiment of Formula IV-V, each $D_1$ is the same moiety. In one embodiment of Formula IV-V, each $D_2$ is the same moiety. In one embodiment of Formula IV-V, each $D_1$ is the same moiety, and each $D_2$ is the same moiety (independently of $D_1$). In one embodiment of Formula IV-V, each M is S, each $D_1$ is the same moiety, and each $D_2$ is the same moiety (independently of $D_1$).

In some embodiments of Formula IV-V, $X_1$, $X_2$, and $X_3$ are each —C(W)— and $Y_1$, $Y_2$, and $Y_3$, are each CH. In some embodiments of Formula IV-V, $X_1$, $X_2$, and $X_3$ are each CH and $Y_1$, $Y_2$, and $Y_3$ are each —C(W)—.

In some embodiments of Formula IV-V, $X_1$, $X_2$, and $X_3$ are each —C(W)— and $Y_1$, $Y_2$, and $Y_3$, are each CH, and each M is S. In some embodiments of Formula IV-V, $X_1$, $X_2$, and $X_3$ are each CH and $Y_1$, $Y_2$, and $Y_3$ are each —C(W)—, and each M is S.

In some embodiments of Formula IV-V, $X_1$, $X_2$, and $X_3$ are each —C(W)— and $Y_1$, $Y_2$, and $Y_3$, are each CH, and each M is O. In some embodiments of Formula IV-V, $X_1$, $X_2$, and $X_3$ are each CH and $Y_1$, $Y_2$, and $Y_3$ are each —C(W)—, and each M is O.

In another embodiment, the invention embraces compounds of Formula IV-V of Formula IV:

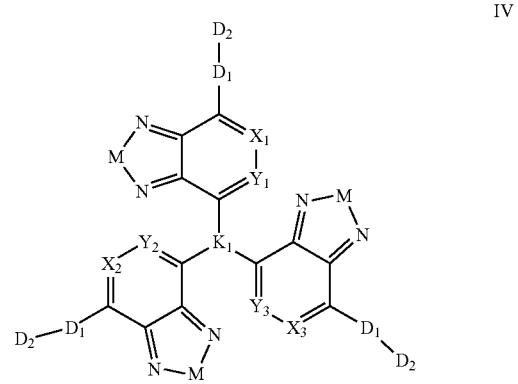

IV where $X_1$ and $Y_1$ are selected from —C(W)— and CH, where when $X_1$ is —C(W)—, $Y_1$ is CH, and when $X_1$ is CH, $Y_1$ is —C(W)—; and where, independently of $X_1$ and $Y_1$, $X_2$ and $Y_2$ are selected from —C(W)— and CH, where when $X_2$ is —C(W)—, $Y_2$ is CH, and when $X_2$ is CH, $Y_2$ is —C(W)—; and where, independently of $X_1$, $Y_1$, $X_2$, and $Y_2$, $X_3$ and $Y_3$ are selected from —C(W)— and CH, where when $X_3$ is —C(W)—, $Y_3$ is CH, and when $X_3$ is CH, $Y_3$ is —C(W)—;

where W is selected from F, Cl, Br, I, —CN, —CF$_3$, —CHF$_2$, or —CH$_2$F; in a further embodiment, W is F;

M is selected from sulfur (S), oxygen (O), or N—R$_1$, where R$_1$ is H, $C_1$-$C_{30}$ alkyl or $C_6$-$C_{30}$ aryl;

$K_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole;

each $D_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole; and each $D_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole.

In one embodiment of Formula IV, each M is S. In one embodiment of Formula IV, each $D_1$ is the same moiety. In one embodiment of Formula IV, each $D_2$ is the same moiety. In one embodiment of Formula IV, each $D_1$ is the same moiety, and each $D_2$ is the same moiety (independently of $D_1$). In one embodiment of Formula IV, each M is S, each $D_1$ is the same moiety, and each $D_2$ is the same moiety (independently of $D_1$).

In some embodiments of Formula IV, $X_1$, $X_2$, and $X_3$ are each —C(W)— and $Y_1$, $Y_2$, and $Y_3$ are each CH; in further embodiments of this type, W is F. In some embodiments of Formula IV, $X_1$, $X_2$, and $X_3$ are each CH and $Y_1$, $Y_2$, and $Y_3$ are each —C(W)—; in further embodiments of this type, W is F.

In some embodiments of Formula IV, $X_1$, $X_2$, and $X_3$ are each —C(W)— and $Y_1$, $Y_2$, and $Y_3$ are each CH, and each M is S; in further embodiments of this type, W is F. In some embodiments of Formula IV, $X_1$, $X_2$, and $X_3$ are each CH and $Y_1$, $Y_2$, and $Y_3$ are each —C(W)—, and each M is S; in further embodiments of this type, W is F.

In some embodiments of Formula IV, $X_1$, $X_2$, and $X_3$ are each —C(W)— and $Y_1$, $Y_2$, and $Y_3$ are each CH, and each M is O; in further embodiments of this type, W is F. In some embodiments of Formula IV, $X_1$, $X_2$, and $X_3$ are each CH and $Y_1$, $Y_2$, and $Y_3$ are each —C(W)—, and each M is O; in further embodiments of this type, W is F.

In another embodiment, the invention embraces compounds of Formula IV of Formula IVa or Formula IVb:

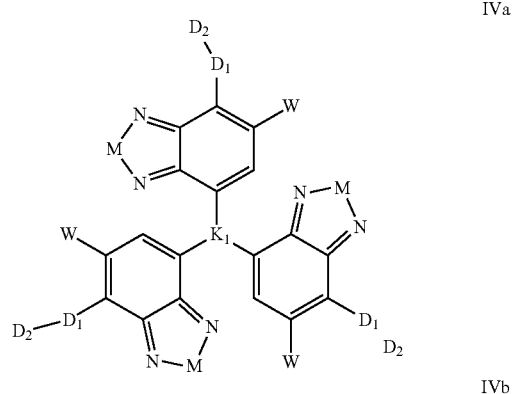

IVa

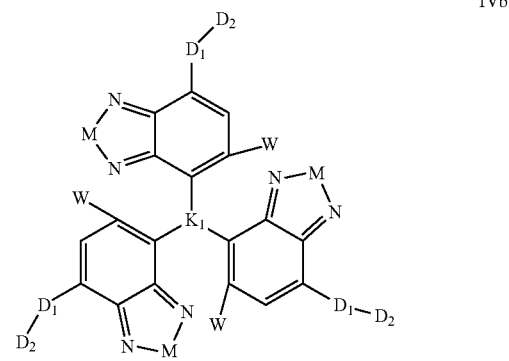

IVb where M is selected from sulfur (S), oxygen (O), or N—$R_1$, where $R_1$ is H, $C_1$-$C_{30}$ alkyl or $C_6$-$C_{30}$ aryl;

where W is selected from F, Cl, Br, I, —CN, —$CF_3$, —$CHF_2$, or —$CH_2F$; in a further embodiment, W is F (Formula IVa-F or Formula IVb-F);

$K_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole;

each $D_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole; and each $D_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole.

In one embodiment of Formula IVa, each M is S. In one embodiment of Formula IVa, each $D_1$ is the same moiety. In one embodiment of Formula IVa, each $D_2$ is the same moiety. In one embodiment of Formula IVa, each $D_1$ is the same moiety, and each $D_2$ is the same moiety (independently of $D_1$). In one embodiment of Formula IVa, each M is S, each $D_1$ is the same moiety, and each $D_2$ is the same moiety (independently of $D_1$). In any of the foregoing embodiments, W can be F.

In one embodiment of Formula IVa, each M is O. In one embodiment of Formula IVa, each $D_1$ is the same moiety. In one embodiment of Formula IVa, each $D_2$ is the same moiety. In one embodiment of Formula IVa, each $D_1$ is the same moiety, and each $D_2$ is the same moiety (independently of $D_1$). In one embodiment of Formula IVa, each M is O, each $D_1$ is the same moiety, and each $D_2$ is the same moiety (independently of $D_1$). In any of the foregoing embodiments, W can be F.

In one embodiment of Formula IVb, each M is S. In one embodiment of Formula IVb, each $D_1$ is the same moiety. In one embodiment of Formula IVb, each $D_2$ is the same moiety. In one embodiment of Formula IVb, each $D_1$ is the same moiety, and each $D_2$ is the same moiety (independently of $D_1$). In one embodiment of Formula IVb, each M is S, each $D_1$ is the same moiety, and each $D_2$ is the same moiety (independently of $D_1$). In any of the foregoing embodiments, W can be F.

In one embodiment of Formula IVb, each M is O. In one embodiment of Formula IVb, each $D_1$ is the same moiety. In one embodiment of Formula IVb, each $D_2$ is the same moiety. In one embodiment of Formula IVb, each $D_1$ is the same moiety, and each $D_2$ is the same moiety (independently of $D_1$). In one embodiment of Formula IVb, each M is O, each $D_1$ is the same moiety, and each $D_2$ is the same moiety (independently of $D_1$). In any of the foregoing embodiments, W can be F.

In another embodiment, the invention embraces compounds of Formula IV-V of Formula V:

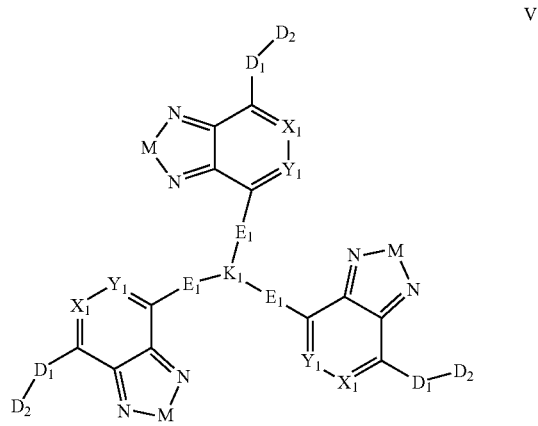

where $X_1$ and $Y_1$ are selected from —C(W)— and CH, where when $X_1$ is —C(W)—, $Y_1$ is CH, and when $X_1$ is CH, $Y_1$ is —C(W)—; and where, independently of $X_1$ and $Y_1$, $X_2$ and $Y_2$ are selected from —C(W)— and CH, where when $X_2$ is —C(W)—, $Y_2$ is CH, and when $X_2$ is CH, $Y_2$ is —C(W)—; and where, independently of $X_1$, $Y_i$, $X_2$, and $Y_2$, $X_3$ and $Y_3$ are selected from —C(W)— and CH, where when $X_3$ is —C(W)—, $Y_3$ is CH, and when $X_3$ is CH, $Y_3$ is —C(W)—;

where M is selected from sulfur (S), oxygen (O), or N—$R_1$, where $R_1$ is H, $C_1$-$C_{30}$ alkyl or $C_6$-$C_{30}$ aryl;

where W is selected from F, Cl, Br, I, —CN, —CF$_3$, —CHF$_2$, or —CH$_2$F; in a further embodiment, W is F;

$K_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole;

each $D_1$ and $E_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole;

each $D_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole.

In one embodiment of Formula V, each M is S. In one embodiment of Formula V, each $D_1$ is the same moiety. In one embodiment of Formula V, each $D_2$ is the same moiety. In one embodiment of Formula V, each $D_1$ is the same moiety, and each $D_2$ is the same moiety (independently of $D_1$). In one embodiment of Formula V, each M is S, each $D_1$ is the same moiety, and each $D_2$ is the same moiety (independently of $D_1$). In any of the foregoing embodiments, W can be F.

In some embodiments of Formula V, $X_1$, $X_2$, and $X_3$ are each —C(W)— and $Y_1$, $Y_2$, and $Y_3$, are each CH. In some embodiments of Formula V, $X_1$, $X_2$, and $X_3$ are each CH and $Y_1$, $Y_2$, and $Y_3$ are each —C(W)—. In any of the foregoing embodiments, W can be F.

In some embodiments of Formula V, $X_1$, $X_2$, and $X_3$ are each —C(W)— and $Y_1$, $Y_2$, and $Y_3$, are each CH, and each M is S. In some embodiments of Formula V, $X_1$, $X_2$, and $X_3$ are each CH and $Y_1$, $Y_2$, and $Y_3$ are each —C(W)—, and each M is S. In any of the foregoing embodiments, W can be F.

In some embodiments of Formula V, $X_1$, $X_2$, and $X_3$ are each —C(W)— and $Y_1$, $Y_2$, and $Y_3$, are each CH, and each M is O. In some embodiments of Formula V, $X_1$, $X_2$, and $X_3$ are each CH and $Y_1$, $Y_2$, and $Y_3$ are each —C(W)—, and each M is O. In any of the foregoing embodiments, W can be F.

In another embodiment, the invention embraces compounds of Formula Va or Formula Vb:

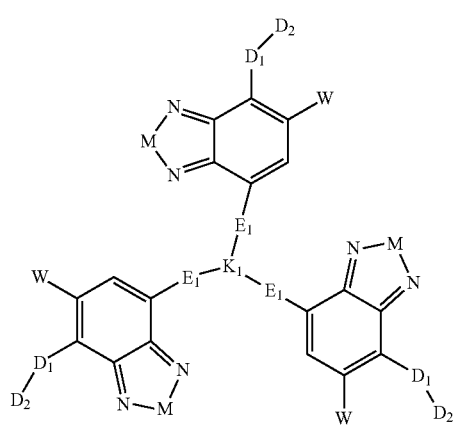

Va

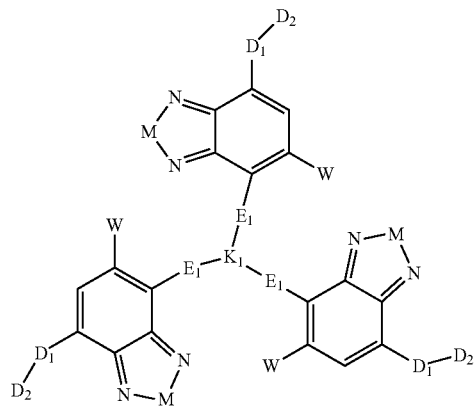

Vb where M is selected from sulfur (S), oxygen (O), or N—$R_1$, where $R_1$ is H, $C_1$-$C_{30}$ alkyl or $C_6$-$C_{30}$ aryl;

where W is selected from F, Cl, Br, I, —CN, —$CF_3$, —$CHF_2$, or —$CH_2F$; in a further embodiment, W is F (Formula Va-F or Formula Vb-F);

$K_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole;

each $D_1$ and $E_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole;

each $D_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole.

In one embodiment of Formula Va, each M is S. In one embodiment of Formula Va, each $E_1$ is the same moiety. In one embodiment of Formula Va, each $D_1$ is the same moiety. In one embodiment of Formula Va, each $D_2$ is the same moiety. In one embodiment of Formula Va, each $E_1$ is the same moiety, each $D_1$ is the same moiety, and each $D_2$ is the same moiety (where $E_1$, $D_1$, and $D_2$ are chosen independently of each other). In one embodiment of Formula Va, each M is S, and each $E_1$ is the same moiety, each $D_1$ is the same moiety, and each $D_2$ is the same moiety (where $E_1$, $D_1$, and $D_2$ are chosen independently of each other). In any of the foregoing embodiments, W can be F.

In one embodiment of Formula Va, each M is O. In one embodiment of Formula Va, each $E_1$ is the same moiety. In one embodiment of Formula Va, each $D_1$ is the same moiety. In one embodiment of Formula Va, each $D_2$ is the same moiety. In one embodiment of Formula Va, each $E_1$ is the same moiety, each $D_1$ is the same moiety, and each $D_2$ is the same moiety (where $E_1$, $D_1$, and $D_2$ are chosen independently of each other). In one embodiment of Formula Va, each M is O, and each $E_1$ is the same moiety, each $D_1$ is the same moiety, and each $D_2$ is the same moiety (where $E_1$, $D_1$, and $D_2$ are chosen independently of each other). In any of the foregoing embodiments, W can be F.

In one embodiment of Formula Vb, each M is S. In one embodiment of Formula Vb, each $E_1$ is the same moiety. In one embodiment of Formula Vb, each $D_1$ is the same moiety. In one embodiment of Formula Vb, each $D_2$ is the same moiety. In one embodiment of Formula Vb, each $E_1$ is the same moiety, each $D_1$ is the same moiety, and each $D_2$ is the same moiety (where $E_1$, $D_1$, and $D_2$ are chosen independently of each other). In one embodiment of Formula Vb, each M is S, and each $E_1$ is the same moiety, each $D_1$ is the same moiety, and each $D_2$ is the same moiety (where $E_1$, $D_1$, and $D_2$ are chosen independently of each other). In any of the foregoing embodiments, W can be F.

In one embodiment of Formula Vb, each M is O. In one embodiment of Formula Vb, each $E_1$ is the same moiety. In one embodiment of Formula Vb, each $D_1$ is the same moiety. In one embodiment of Formula Vb, each $D_2$ is the same moiety. In one embodiment of Formula Vb, each $E_1$ is the same moiety, each $D_1$ is the same moiety, and each $D_2$ is the same moiety (where $E_1$, $D_1$, and $D_2$ are chosen independently of each other). In one embodiment of Formula Vb, each M is O, and each $E_1$ is the same moiety, each $D_1$ is the same moiety, and each $D_2$ is the same moiety (where $E_1$, $D_1$, and $D_2$ are chosen independently of each other). In any of the foregoing embodiments, W can be F.

In another embodiment, the invention embraces compounds of Formula VI-VII:

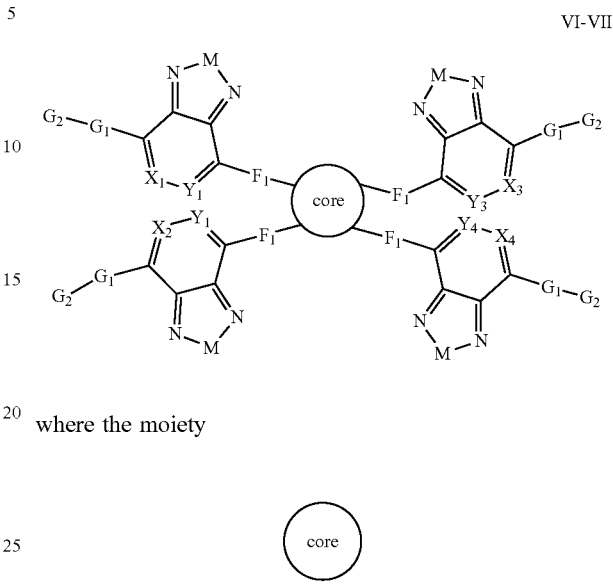

VI-VII where the moiety

is selected from

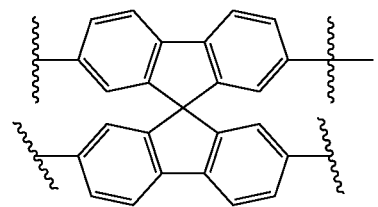 [SMILES: *c1ccc2c(c1)C1(c3cc(*)ccc3-2)c2cc(*)ccc2-c2ccc(*)cc21]

(2,2',7,7'-yl-9,9'-spirobi[fluorene]),

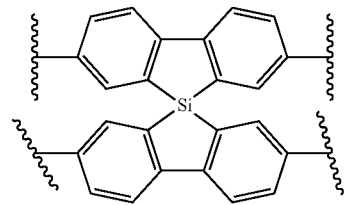 [SMILES: *c1ccc2c(c1)[Si]1(c3cc(*)ccc3-2)c2cc(*)ccc2-c2ccc(*)cc21]

(3,3',7,7'-yl-5,5'-spirobi[dibenzo[b,d]silole]),

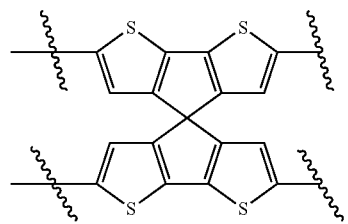 [SMILES: *c1cc2c(s1)-c1sc(*)cc1C21c2cc(*)sc2-c2sc(*)cc21]

(2,2',6,6'-yl-4,4"-spirobi[cyclopenta[1,2-b:5,4-b']dithiophene]), and

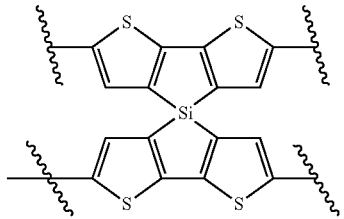 [SMILES: *c1cc2c(s1)-c1sc(*)cc1[Si]21c2cc(*)sc2-c2sc(*)cc21]

(2,2',6,6'-yl-4,4'-spirobi[silolo[3,2-b:4,5-b']dithiophene]);

where $X_1$ and $Y_1$ are selected from —C(W)— and CH, where when $X_1$ is —C(W)—, $Y_1$ is CH, and when $X_1$ is CH, $Y_1$ is —C(W)—; and where, independently of $X_1$ and $Y_1$, $X_2$ and $Y_2$ are selected from —C(W)— and CH, where when $X_2$ is —C(W)—, $Y_2$ is CH, and when $X_2$ is CH, $Y_2$ is —C(W)—; and where, independently of $X_1$, $Y_1$, $X_2$, and $Y_2$, $X_3$ and $Y_3$ are selected from —C(W)— and CH, where when $X_3$ is —C(W)—, $Y_3$ is CH, and when $X_3$ is CH, $Y_3$ is —C(W)—; and where, independently of $X_1$, $Y_1$, $X_2$, $Y_2$, $X_3$, and $Y_3$, $X_4$ and $Y_4$ are selected from —C(W)— and CH, where when $X_4$ is —C(W)—, $Y_4$ is CH, and when $X_4$ is CH, $Y_4$ is —C(W)—;

where M is selected from sulfur (S), oxygen (O), or N—$R_1$, where $R_1$ is H, $C_1$-$C_{30}$ alkyl or $C_6$-$C_{30}$ aryl;

where W is selected from F, Cl, Br, I, —CN, —$CF_3$, —$CHF_2$, or —$CH_2F$; in a further embodiment, W is F;

each $F_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, dithienopyrrole, dithienophosphole, and carbazole 9,9-RR'-9H-fluorene, 9-R-9H-carbazole, 3,3'-RR'silylene-2,2'-bithiophene, 3,3'RR'-cyclopenta[2,1-b:3,4-b']-dithiophene, where R and R'=$C_1$-$C_{30}$ alkyl or $C_6$-$C_{30}$ aryl;

each $G_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole; and each $G_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole.

In some embodiments of Formula VI-VII, each M is S. In other embodiments of Formula VI-VII, each M is O.

In some embodiments of Formula VI-VII, $X_1$, $X_2$, $X_3$, and $X_4$ are each —C(W)— and $Y_1$, $Y_2$, $Y_3$, and $Y_4$ are each CH. In some embodiments of Formula VI-VII, $X_1$, $X_2$, $X_3$, and $X_4$ are each CH and $Y_1$, $Y_2$, $Y_3$, and $Y_4$ are each —C(W)—. In any of the foregoing embodiments, W can be F.

In some embodiments of Formula VI-VII, $X_1$, $X_2$, $X_3$, and $X_4$ are each —C(W)— and $Y_1$, $Y_2$, $Y_3$, and $Y_4$ are each CH, and each M is S. In some embodiments of Formula VI-VII, $X_1$, $X_2$, $X_3$, and $X_4$ are each CH and $Y_1$, $Y_2$, $Y_3$, and $Y_4$ are each —C(W)—, and each M is S. In any of the foregoing embodiments, W can be F.

In some embodiments of Formula VI-VII, $X_1$, $X_2$, $X_3$, and $X_4$ are each —C(W)— and $Y_1$, $Y_2$, $Y_3$, and $Y_4$ are each CH, and each M is O. In some embodiments of Formula VI-VII, $X_1$, $X_2$, $X_3$, and $X_4$ are each CH and $Y_1$, $Y_2$, $Y_3$, and $Y_4$ are each —C(W)—, and each M is O. In any of the foregoing embodiments, W can be F.

In some embodiments of Formula VI-VII, each $F_1$ is the same moiety. In some embodiments of Formula VI-VII, each $G_1$ is the same moiety. In some embodiments of Formula VI-VII, each $G_2$ is the same moiety. In some embodiments of Formula VI-VII, each $F_1$ is the same moiety, each $G_1$ is the same moiety, and each $G_2$ is the same moiety (where $F_1$, $G_1$, and $G_2$ are chosen independently of each other). In some embodiments of Formula VI-VII, each $F_1$ is the same moiety, each $G_1$ is the same moiety, and each $G_2$ is the same moiety (where $F_1$, $G_1$, and $G_2$ are chosen independently of each other); and M is S. In some embodiments of Formula VI-VII, each $F_1$ is the same moiety, each $G_1$ is the same moiety, and each $G_2$ is the same moiety (where $F_1$, $G_1$, and $G_2$ are chosen independently of each other); and M is O.

In another embodiment, the invention embraces compounds of Formula VI:

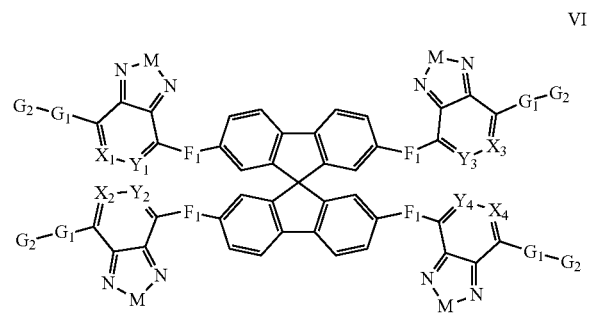

where $X_1$ and $Y_1$ are selected from —C(W)— and CH, where when $X_1$ is —C(W)—, $Y_1$ is CH, and when $X_1$ is CH, $Y_1$ is —C(W)—; and where, independently of $X_1$ and $Y_1$, $X_2$ and $Y_2$ are selected from —C(W)— and CH, where when $X_2$ is —C(W)—, $Y_2$ is CH, and when $X_2$ is CH, $Y_2$ is —C(W)—; and where, independently of $X_1$, $Y_1$, $X_2$, and $Y_2$, $X_3$ and $Y_3$ are selected from —C(W)— and CH, where when $X_3$ is —C(W)—, $Y_3$ is CH, and when $X_3$ is CH, $Y_3$ is —C(W)—; and where, independently of $X_1$, $Y_1$, $X_2$, $Y_2$, $X_3$, and $Y_3$, $X_4$ and $Y_4$ are selected from —C(W)— and CH, where when $X_4$ is —C(W)—, $Y_4$ is CH, and when $X_4$ is CH, $Y_4$ is —C(W)—;

where M is selected from sulfur (S), oxygen (O), or N—$R_1$, where $R_1$ is H, $C_1$-$C_{30}$ alkyl or $C_6$-$C_{30}$ aryl;

where W is selected from F, Cl, Br, I, —CN, —CF$_3$, —CHF$_2$, or —CH$_2$F; in a further embodiment, W is F;

each $F_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, dithienopyrrole, dithienophosphole, and carbazole 9,9-RR'-9H-fluorene, 9-R-9H-carbazole, 3,3'-RR'silylene-2,2'-bithiophene, 3,3'RR'-cyclopenta[2,1-b:3,4-b']-dithiophene, where R and R'=$C_1$-$C_{30}$ alkyl or $C_6$-$C_{30}$ aryl;

each $G_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole; and each $G_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole.

In some embodiments of Formula VI, each M is S. In other embodiments of Formula VI, each M is O.

In some embodiments of Formula VI, $X_1$, $X_2$, $X_3$, and $X_4$ are each —C(W)— and $Y_1$, $Y_2$, $Y_3$, and $Y_4$ are each CH. In some embodiments of Formula VI, $X_1$, $X_2$, $X_3$, and $X_4$ are each CH and $Y_1$, $Y_2$, $Y_3$, and $Y_4$ are each —C(W)—. In any of the foregoing embodiments, W can be F.

In some embodiments of Formula VI, $X_1$, $X_2$, $X_3$, and $X_4$ are each —C(W)— and $Y_1$, $Y_2$, $Y_3$, and $Y_4$ are each CH, and each M is S. In some embodiments of Formula VI, $X_1$, $X_2$, $X_3$, and $X_4$ are each CH and $Y_1$, $Y_2$, $Y_3$, and $Y_4$ are each —C(W)—, and each M is S. In any of the foregoing embodiments, W can be F.

In some embodiments of Formula VI, $X_1$, $X_2$, $X_3$, and $X_4$ are each —C(W)— and $Y_1$, $Y_2$, $Y_3$, and $Y_4$ are each CH, and each M is O. In some embodiments of Formula VI, $X_1$, $X_2$, $X_3$, and $X_4$ are each CH and $Y_1$, $Y_2$, $Y_3$, and $Y_4$ are each —C(W)—, and each M is O. In any of the foregoing embodiments, W can be F.

In some embodiments of Formula VI, each $F_1$ is the same. In some embodiments of Formula VI, each $G_1$ is the same. In some embodiments of Formula VI, each $G_2$ is the same. In some embodiments of Formula VI, each $F_1$ is the same, each $G_1$ is the same, and each $G_2$ is the same (where $F_1$, $G_1$, and $G_2$ are chosen independently of each other). In some embodiments of Formula VI, each $F_1$ is the same, each $G_1$ is the same, and each $G_2$ is the same (where $F_1$, $G_1$, and $G_2$ are chosen independently of each other); and M is S. In some embodiments of Formula VI, each $F_1$ is the same, each $G_1$ is the same, and each $G_2$ is the same (where $F_1$, $G_1$, and $G_2$ are chosen independently of each other); and M is O.

In another embodiment, the invention embraces compounds of Formula VI, such as compounds of Formula VIa or Formula VIb:

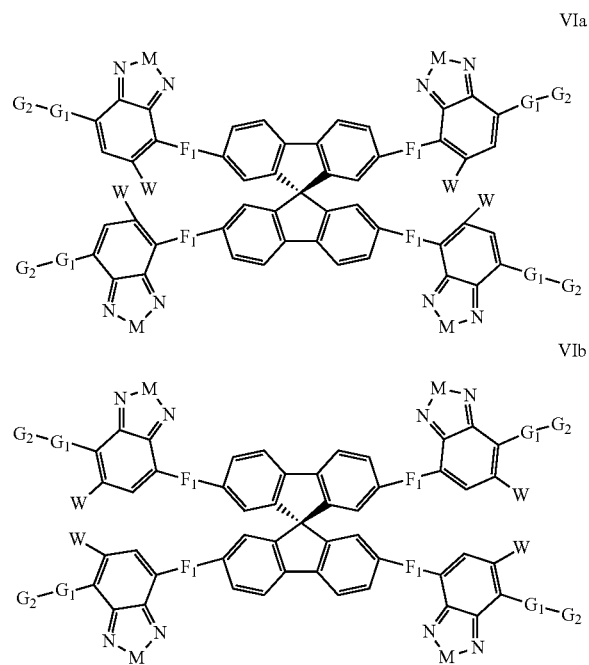

where M is selected from sulfur (S), oxygen (O), or N—R$_1$, where R$_1$ is H, C$_1$-C$_{30}$ alkyl or C$_6$-C$_{30}$ aryl;

where W is selected from F, Cl, Br, I, —CN, —CF$_3$, —CHF$_2$, or —CH$_2$F; in a further embodiment, W is F (fluorine) (Formula VIa-F or Formula VIb-F);

each F$_1$ is independently selected from substituted or unsubstituted aryl or heteroaryl groups, such as C$_6$-C$_{30}$ substituted or unsubstituted aryl or heteroaryl groups, C$_6$-C$_{20}$ substituted or unsubstituted aryl or heteroaryl groups, and C$_6$-C$_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, dithienopyrrole, dithienophosphole, and carbazole 9,9-RR'-9H-fluorene, 9-R-9H-carbazole, 3,3'-RR'silylene-2,2'-bithiophene, 3,3'RR'-cyclopenta[2,1-b:3,4-b']-dithiophene, where R and R'=C$_1$-C$_{30}$ alkyl or C$_6$-C$_{30}$ aryl;

each G$_1$ is independently selected from substituted or unsubstituted aryl or heteroaryl groups, such as C$_6$-C$_{30}$ substituted or unsubstituted aryl or heteroaryl groups, C$_6$-C$_{20}$ substituted or unsubstituted aryl or heteroaryl groups, and C$_6$-C$_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole; and each G$_2$ is independently selected from a nonentity, H, F, a C$_1$-C$_{16}$ alkyl group, or a substituted or unsubstituted aryl or heteroaryl group, such as C$_6$-C$_{30}$ substituted or unsubstituted aryl or heteroaryl groups, C$_6$-C$_{20}$ substituted or unsubstituted aryl or heteroaryl groups, and C$_6$-C$_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole.

In some embodiments of Formula VIa, each M is S. In other embodiments of Formula VIa, each M is O. In some embodiments of Formula VIa, each F$_1$ is the same. In some embodiments of Formula VIa, each G$_1$ is the same. In some embodiments of Formula VIa, each G$_2$ is the same. In some embodiments of Formula VIa, each F$_1$ is the same, each G$_1$ is the same, and each G$_2$ is the same (where F$_1$, G$_1$, and G$_2$ are chosen independently of each other). In some embodiments of Formula VIa, each F$_1$ is the same, each G$_1$ is the same, and each G$_2$ is the same (where F$_1$, G$_1$, and G$_2$ are chosen independently of each other); and M is S. In some embodiments of Formula VIa, each F$_1$ is the same, each G$_1$ is the same (where F$_1$, G$_1$, and G$_2$ are chosen independently of each other), and each G$_2$ is the same; and M is O. In any of the foregoing embodiments, W can be F (fluorine).

In some embodiments of Formula VIb, each M is S. In other embodiments of Formula VIb, each M is O. In some embodiments of Formula VIb, each F$_1$ is the same. In some embodiments of Formula VIb, each G$_1$ is the same. In some embodiments of Formula VIb, each G$_2$ is the same. In some embodiments of Formula VIb, each F$_1$ is the same, each G$_1$ is the same, and each G$_2$ is the same (where F$_1$, G$_1$, and G$_2$ are chosen independently of each other). In some embodiments of Formula VIb, each F$_1$ is the same, each G$_1$ is the same, and each G$_2$ is the same (where F$_1$, G$_1$, and G$_2$ are chosen independently of each other); and M is S. In some embodiments of Formula VIb, each F$_1$ is the same, each G$_1$ is the same (where F$_1$, G$_1$, and G$_2$ are chosen independently of each other), and each G$_2$ is the same; and M is O. In any of the foregoing embodiments, W can be F (fluorine).

In another embodiment, the invention embraces compounds of Formula VII:

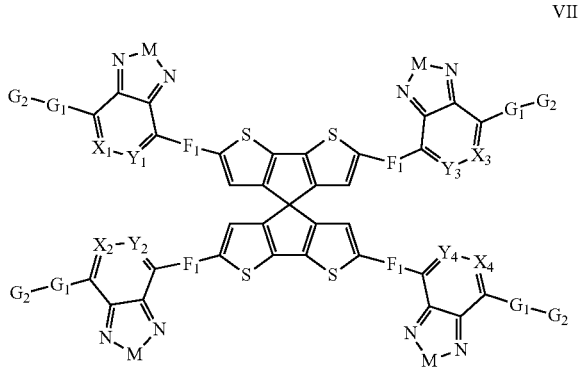

where $X_1$ and $Y_1$ are selected from —C(W)— and CH, where when $X_1$ is —C(W)—, $Y_1$ is CH, and when $X_1$ is CH, $Y_1$ is —C(W)—; and where, independently of $X_1$ and $Y_1$, $X_2$ and $Y_2$ are selected from —C(W)— and CH, where when $X_2$ is —C(W)—, $Y_2$ is CH, and when $X_2$ is CH, $Y_2$ is —C(W)—; and where, independently of $X_1$, $Y_1$, $X_2$, and $Y_2$, $X_3$ and $Y_3$ are selected from —C(W)— and CH, where when $X_3$ is —C(W)—, $Y_3$ is CH, and when $X_3$ is CH, $Y_3$ is —C(W)—; and where, independently of $X_1$, $Y_1$, $X_2$, $Y_2$, $X_3$, and $Y_3$, $X_4$ and $Y_4$ are selected from —C(W)— and CH, where when $X_4$ is —C(W)—, $Y_4$ is CH, and when $X_4$ is CH, $Y_4$ is —C(W)—;

where W is selected from F, Cl, Br, I, —CN, —CF$_3$, —CHF$_2$, or —CH$_2$F; in a further embodiment, W is F (fluorine);

where M is selected from sulfur (S), oxygen (O), or N—$R_1$, where $R_1$ is H, $C_1$-$C_{30}$ alkyl or $C_6$-$C_{30}$ aryl;

each $F_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, dithienopyrrole, dithienophosphole, and carbazole 9,9-RR'-9H-fluorene, 9-R-9H-carbazole, 3,3'-RR'silylene-2,2'-bithiophene, 3,3'RR'-cyclopenta[2,1-b:3,4-b']-dithiophene, where R and R'=$C_1$-$C_{30}$ alkyl or $C_6$-$C_{30}$ aryl;

each $G_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole; and each $G_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole.

In some embodiments of Formula VII, each M is S. In other embodiments of Formula VII, each M is O.

In some embodiments of Formula VII, $X_1$, $X_2$, $X_3$, and $X_4$ are each —C(W)— and $Y_1$, $Y_2$, $Y_3$, and $Y_4$ are each CH. In some embodiments of Formula VII, $X_1$, $X_2$, $X_3$, and $X_4$ are each CH and $Y_1$, $Y_2$, $Y_3$, and $Y_4$ are each —C(W)—. In any of the foregoing embodiments, W can be F (fluorine).

In some embodiments of Formula VII, $X_1$, $X_2$, $X_3$, and $X_4$ are each —C(W)— and $Y_1$, $Y_2$, $Y_3$, and $Y_4$ are each CH, and each M is S. In some embodiments of Formula VII, $X_1$, $X_2$, $X_3$, and $X_4$ are each CH and $Y_1$, $Y_2$, $Y_3$, and $Y_4$ are each —C(W)—, and each M is S. In any of the foregoing embodiments, W can be F (fluorine).

In some embodiments of Formula VII, $X_1$, $X_2$, $X_3$, and $X_4$ are each —C(W)— and $Y_1$, $Y_2$, $Y_3$, and $Y_4$ are each CH, and each M is O. In some embodiments of Formula VII, $X_1$, $X_2$, $X_3$, and $X_4$ are each CH and $Y_1$, $Y_2$, $Y_3$, and $Y_4$ are each —C(W)—, and each M is O. In any of the foregoing embodiments, W can be F (fluorine).

In some embodiments of Formula VII, each $F_1$ is the same. In some embodiments of Formula VII, each $G_1$ is the same. In some embodiments of Formula VII, each $G_2$ is the same. In some embodiments of Formula VII, each $F_1$ is the same, each $G_1$ is the same, and each $G_2$ is the same (where $F_1$, $G_1$, and $G_2$ are chosen independently of each other). In some embodiments of Formula VII, each $F_1$ is the same, each $G_1$ is the same, and each $G_2$ is the same (where $F_1$, $G_1$, and $G_2$ are chosen independently of each other); and M is S. In some embodiments of Formula VII, each $F_1$ is the same, each $G_1$ is the same, and each $G_2$ is the same (where $F_1$, $G_1$, and $G_2$ are chosen independently of each other); and M is O.

In another embodiment, the invention embraces compounds of Formula VII, such as compounds of Formula VIIa or Formula VIIb:

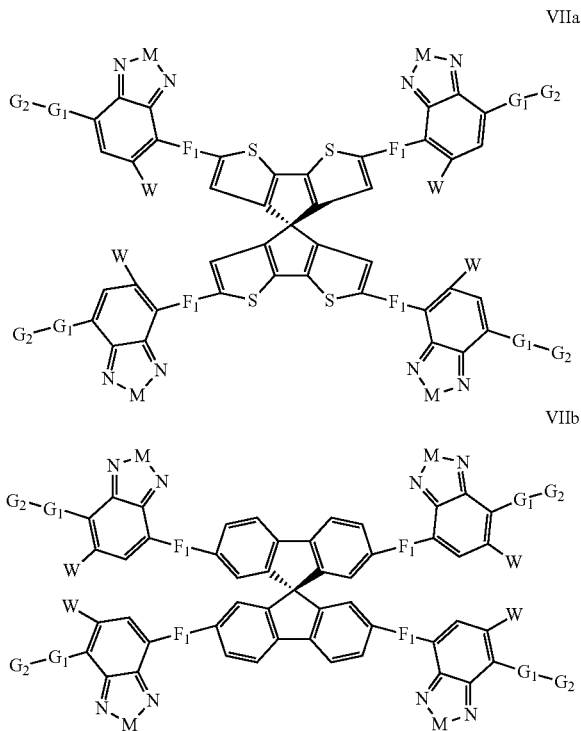

where M is selected from sulfur (S), oxygen (O), or N—$R_1$, where $R_1$ is H, $C_1$-$C_{30}$ alkyl or $C_6$-$C_{30}$ aryl;

where W is selected from F, Cl, Br, I, —CN, —$CF_3$, —$CHF_2$, or —$CH_2F$; in a further embodiment, W is F (fluorine) (Formula VIIa-F or Formula VIIb-F);

each $F_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, dithienopyrrole, dithienophosphole, and carbazole 9,9-RR'-9H-fluorene, 9-R-9H-carbazole, 3,3'-RR'silylene-2,2'-bithiophene, 3,3'RR'-cyclopenta[2,1-b:3,4-b']-dithiophene, where R and R'=$C_1$-$C_{30}$ alkyl or $C_6$-$C_{30}$ aryl.

each $G_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole.

each $G_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole.

In some embodiments of Formula VIIa, each M is S. In other embodiments of Formula VIIa, each M is O. In some embodiments of Formula VIIa, each $F_1$ is the same. In some embodiments of Formula VIIa, each $G_1$ is the same. In some embodiments of Formula VIIa, each $G_2$ is the same. In some embodiments of Formula VIIa, each $F_1$ is the same, each $G_1$ is the same, and each $G_2$ is the same (where Gi and $G_2$ are chosen independently of each other). In some embodiments of Formula VIIa, each $F_1$ is the same, each $G_1$ is the same, and each $G_2$ is the same (where $F_1$, $G_1$, and $G_2$ are chosen independently of each other); and M is S. In some embodiments of Formula VIIa, each $F_1$ is the same, each $G_1$ is the same (where $F_1$, $G_1$, and $G_2$ are chosen independently of each other), and each $G_2$ is the same; and M is O. In any of the foregoing embodiments, W can be F (fluorine).

In some embodiments of Formula VIIb, each M is S. In other embodiments of Formula VIIb, each M is O. In some embodiments of Formula VIIb, each $F_1$ is the same. In some embodiments of Formula VIIb, each $G_1$ is the same. In some embodiments of Formula VIIb, each $G_2$ is the same. In some embodiments of Formula VIIb, each $F_1$ is the same, each Gi is the same, and each $G_2$ is the same (where $F_1$, $G_1$, and $G_2$ are chosen independently of each other). In some embodiments of Formula VIIb, each $F_1$ is the same, each $G_1$ is the same, and each $G_2$ is the same (where $F_1$, $G_1$, and $G_2$ are chosen independently of each other); and M is S. In some embodiments of Formula VIIb, each $F_1$ is the same, each $G_1$ is the same, and each $G_2$ is the same (where $F_1$, $G_1$, and $G_2$ are chosen independently of each other); and M is O. In any of the foregoing embodiments, W can be F (fluorine).

In additional embodiments, the invention embraces compounds of Formula 1-2-3-4-5:

where P₁ is selected from

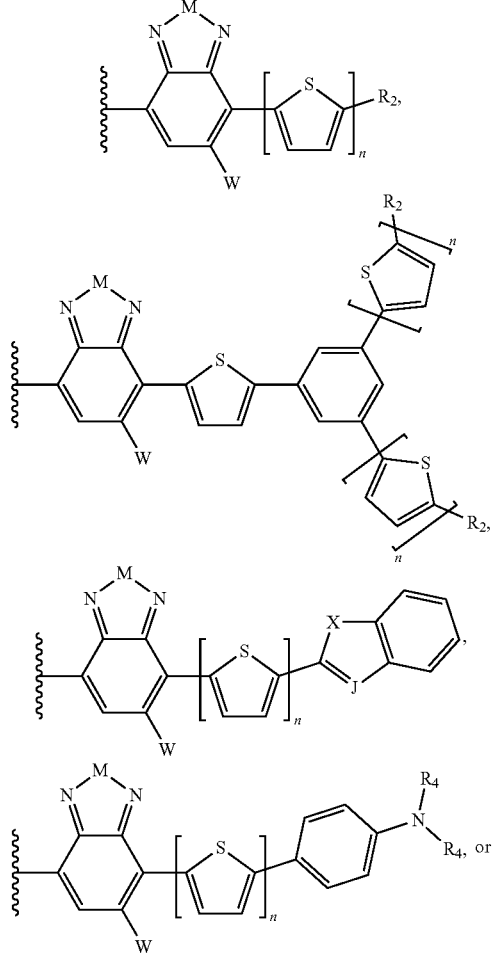

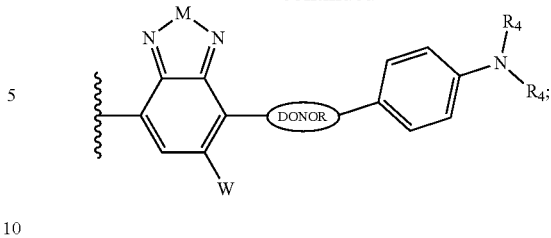

where M is selected from sulfur (S), oxygen (O), or N—$R_1$, where $R_1$ is H, $C_1$-$C_{30}$ alkyl or $C_6$-$C_{30}$ aryl;

where W is selected from F, Cl, Br, I, —CN, —$CF_3$, —$CHF_2$, or —$CH_2F$; in a further embodiment, W is F;

n is an integer from 0 to 5 inclusive;

$R_2$ is selected from H, $C_1$-$C_{16}$ alkyl, —O—$C_1$-$C_{16}$ alkyl, $C_2$-$C_{16}$ alkenyl, and $C_2$-$C_{16}$ alkynyl;

J is selected from CH and N;

X is S, O, or NH when J is CH; and X is S when J is N;

$R_4$ is selected from aryl or aryl substituted with alkyl, such as $C_6$-$C_{30}$ aryl optionally substituted with one or more $C_1$-$C_{16}$ alkyl groups, $C_6$-$C_{20}$ aryl optionally substituted with one or more $C_1$-$C_{16}$ alkyl groups, and $C_6$-$C_{10}$ aryl groups optionally substituted with one or more $C_1$-$C_{16}$ alkyl groups, and where DONOR is as defined below.

In one embodiment, n is 0. In another embodiment, n is 1. In another embodiment, n is 2. In another embodiment, n is 3. In another embodiment, n is 4. In another embodiment, n is 5;

In additional embodiments, the invention embraces compounds of Formula 1, Formula 2, Formula 3, Formula 4, or Formula 5:

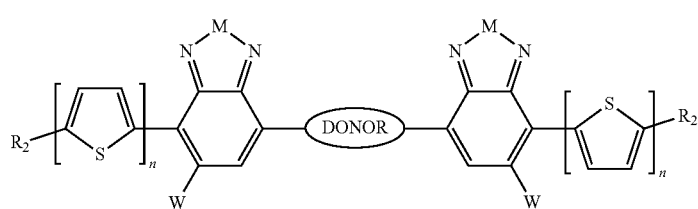

1

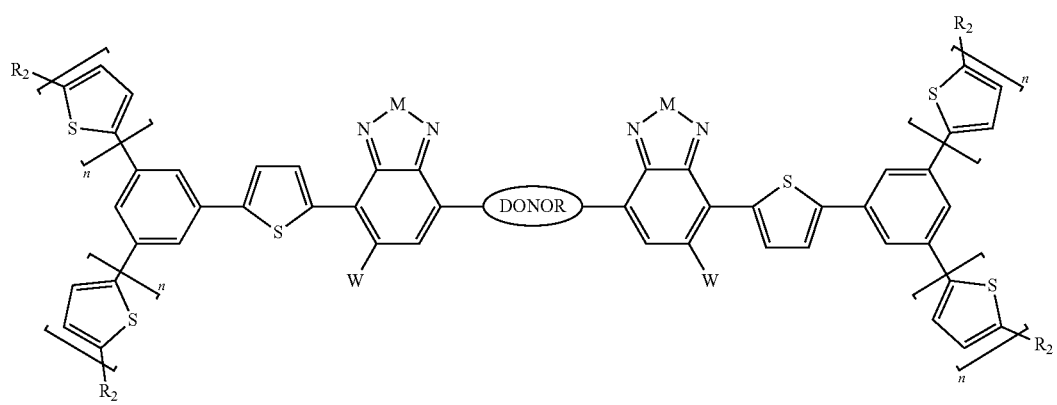

2

-continued

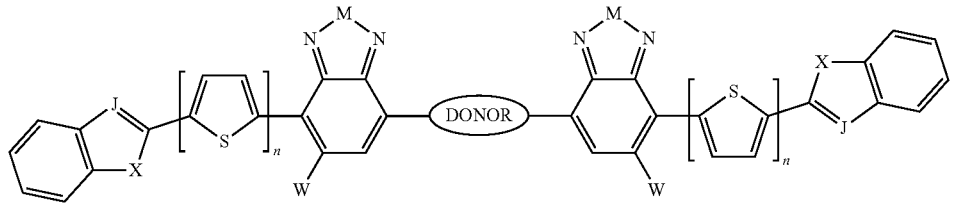

3

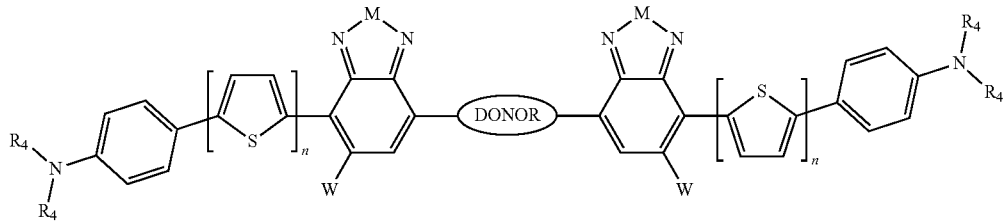

4

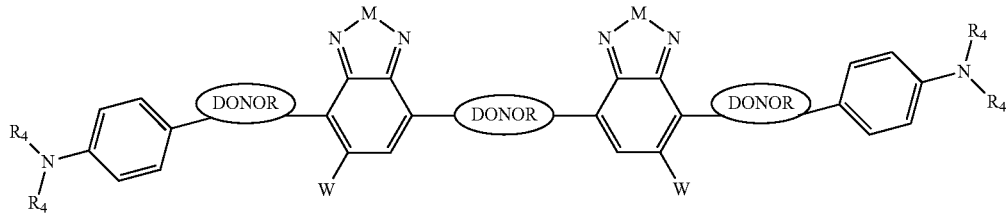

5

In the structures for Formula 1, Formula 2, Formula 3, Formula 4, and Formula 5 above:

M is selected from sulfur (S), oxygen (O), or N—$R_1$, where $R_1$ is H, $C_1$-$C_{30}$ alkyl or $C_6$-$C_{30}$ aryl;

W is selected from F, Cl, Br, I, —CN, —$CF_3$, —$CHF_2$, or —$CH_2F$; in a further embodiment, W is F (Formula 1-F, Formula 2-F, Formula 3-F, Formula 4-F, or Formula 5-F);

n is an integer from 0 to 5 inclusive;

$R_2$ is selected from H, $C_1$-$C_{16}$ alkyl, —O—$C_1$-$C_{16}$ alkyl, $C_2$-$C_{16}$ alkenyl, and $C_2$-$C_{16}$ alkynyl;

J is selected from CH and N;

X is S, O, or NH when J is CH; and X is S when J is N;

$R_4$ is selected from aryl or aryl substituted with alkyl, such as $C_6$-$C_{30}$ aryl optionally substituted with one or more $C_1$-$C_{16}$ alkyl groups, $C_6$-$C_{20}$ aryl optionally substituted with one or more $C_1$-$C_{16}$ alkyl groups, and $C_6$-$C_{10}$ aryl groups optionally substituted with one or more $C_1$-$C_{16}$ alkyl groups, and where DONOR is as defined below.

In one embodiment, n is 0. In another embodiment, n is 1. In another embodiment, n is 2. In another embodiment, n is 3. In another embodiment, n is 4. In another embodiment, n is 5. In any of the foregoing embodiments, W can be F.

In additional embodiments, the invention embraces compounds of Formula 6-7-8:

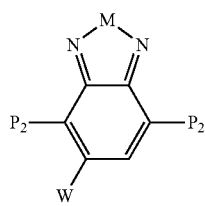

where $P_2$ is selected from:

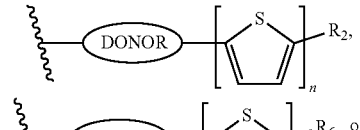

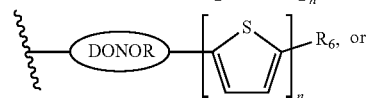

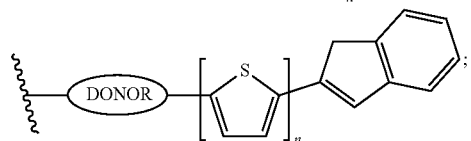

where M is selected from sulfur (S), oxygen (O), or N—$R_1$, where $R_1$ is H, $C_1$-$C_{30}$ alkyl or $C_6$-$C_{30}$ aryl;

W is selected from F, Cl, Br, I, —CN, —$CF_3$, —$CHF_2$, or —$CH_2F$; in a further embodiment, W is F;

n is an integer from 0 to 5 inclusive;

$R_2$ is selected from H, $C_1$-$C_{16}$ alkyl, —O—$C_1$-$C_{16}$ alkyl, $C_2$-$C_{16}$ alkenyl, and $C_2$-$C_{16}$ alkynyl;

J is selected from CH and N;

X is S, O, or NH when J is CH; and X is S when J is N;

$R_6$ is selected from aryl, perfluoroaryl, or aryl substituted with alkyl, such as $C_6$-$C_{30}$ aryl optionally perfluorinated or optionally substituted with one or more $C_1$-$C_{16}$ alkyl groups, $C_6$-$C_{20}$ aryl optionally perfluorinated or optionally substituted with one or more $C_1$-$C_{16}$ alkyl groups, and $C_6$-$C_{10}$ aryl groups optionally perfluorinated or optionally substituted with one or more $C_1$-$C_{16}$ alkyl groups; and where DONOR is as defined below.

In one embodiment, n is 0. In another embodiment, n is 1. In another embodiment, n is 2. In another embodiment, n is 3. In another embodiment, n is 4. In another embodiment, n is 5. In any of the foregoing embodiments, W can be F.

In additional embodiments, the invention embraces compounds of Formula 6, Formula 7, or Formula 8:

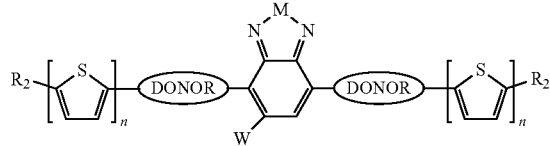

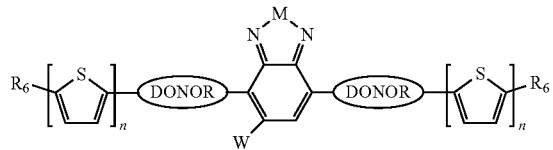

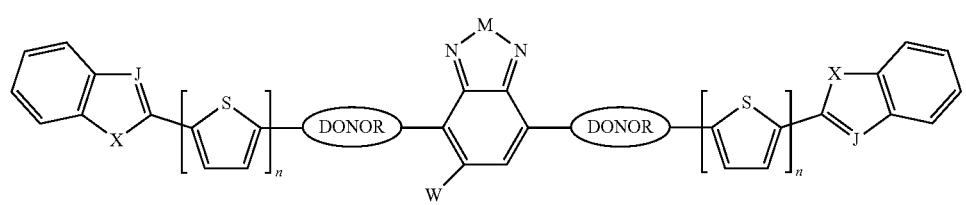

In the structures for Formula 6, Formula 7, and Formula 8 above:
M is selected from sulfur (S), oxygen (O), or N—$R_1$, where $R_1$ is H, $C_1$-$C_{30}$ alkyl or $C_6$-$C_{30}$ aryl;
W is selected from F, Cl, Br, I, —CN, —$CF_3$, —$CHF_2$, or —$CH_2F$; in a further embodiment, W is F (Formula 6-F, Formula 7-F, or Formula 8-F);
n is an integer from 0 to 5 inclusive;
$R_2$ is selected from H, $C_1$-$C_{16}$ alkyl, —O—$C_1$-$C_{16}$ alkyl, $C_2$-$C_{16}$ alkenyl, and $C_2$-$C_{16}$ alkynyl;
J is selected from CH and N;
X is S, O, or NH when J is CH; and X is S when J is N;
$R_6$ is selected from aryl, perfluoroaryl, or aryl substituted with alkyl, such as $C_6$-$C_{30}$ aryl optionally perfluorinated or optionally substituted with one or more $C_1$-$C_{16}$ alkyl groups, $C_6$-$C_{20}$ aryl optionally perfluorinated or optionally substituted with one or more $C_1$-$C_{16}$ alkyl groups, and $C_6$-$C_{10}$ aryl groups optionally perfluorinated or optionally substituted with one or more $C_1$-$C_{16}$ alkyl groups; and
where DONOR is as defined below.

In one embodiment, n is 0. In another embodiment, n is 1. In another embodiment, n is 2. In another embodiment, n is 3. In another embodiment, n is 4. In another embodiment, n is 5. In any of the foregoing embodiments, W can be F.

In additional embodiments, the invention embraces compounds of Formula 9-10:

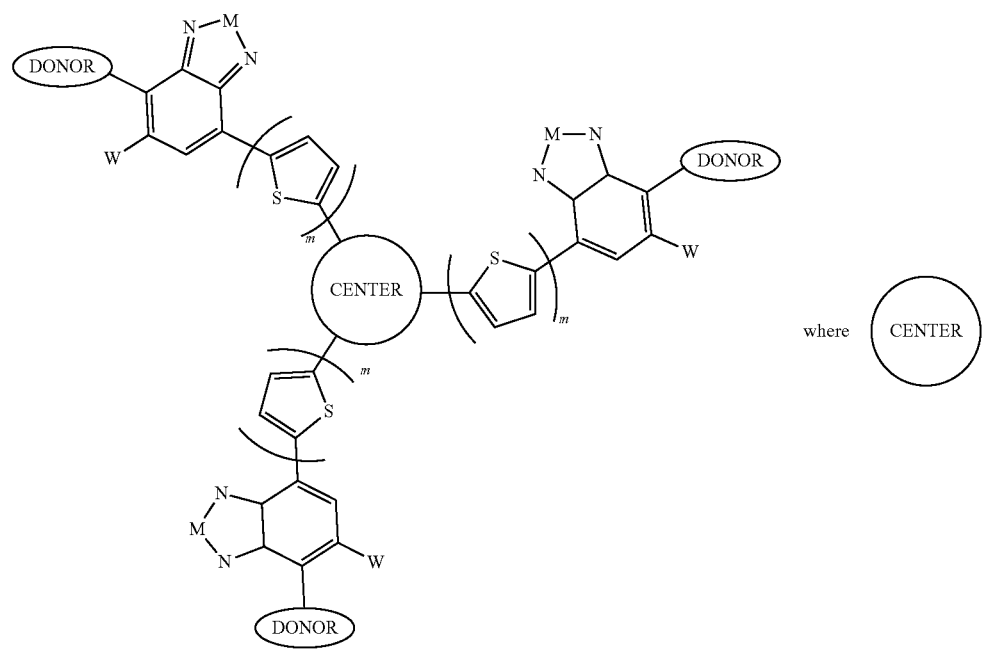

is selected from

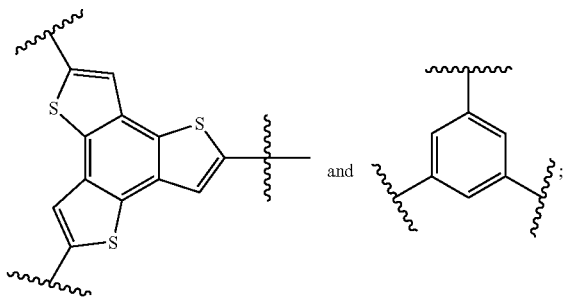 [SMILES: *c1cc2c(s1)c1cc(*)sc1c1cc(*)sc21 ; *c1cc(*)cc(*)c1]

and where M is selected from sulfur (S), oxygen (O), or N—$R_1$, where $R_1$ is H, $C_1$-$C_{30}$ alkyl or $C_6$-$C_{30}$ aryl;

W is selected from F, Cl, Br, I, —CN, —$CF_3$, —$CHF_2$, or —$CH_2F$; in a further embodiment, W is F;

n is an integer from 1 to 5 inclusive, and m is an integer from 0 to 5 inclusive; and where DONOR is as defined below.

In one embodiment, n is 1. In another embodiment, n is 2. In another embodiment, n is 3. In another embodiment, n is 4. In another embodiment, n is 5. In another embodiment, m is 0. In another embodiment, m is 1. In another embodiment, m is 2. In another embodiment, m is 3. In another embodiment, m is 4. In another embodiment, m is 5. In any of the foregoing embodiments, W can be F.

In additional embodiments, the invention embraces compounds of Formula 9 or Formula 10:

9

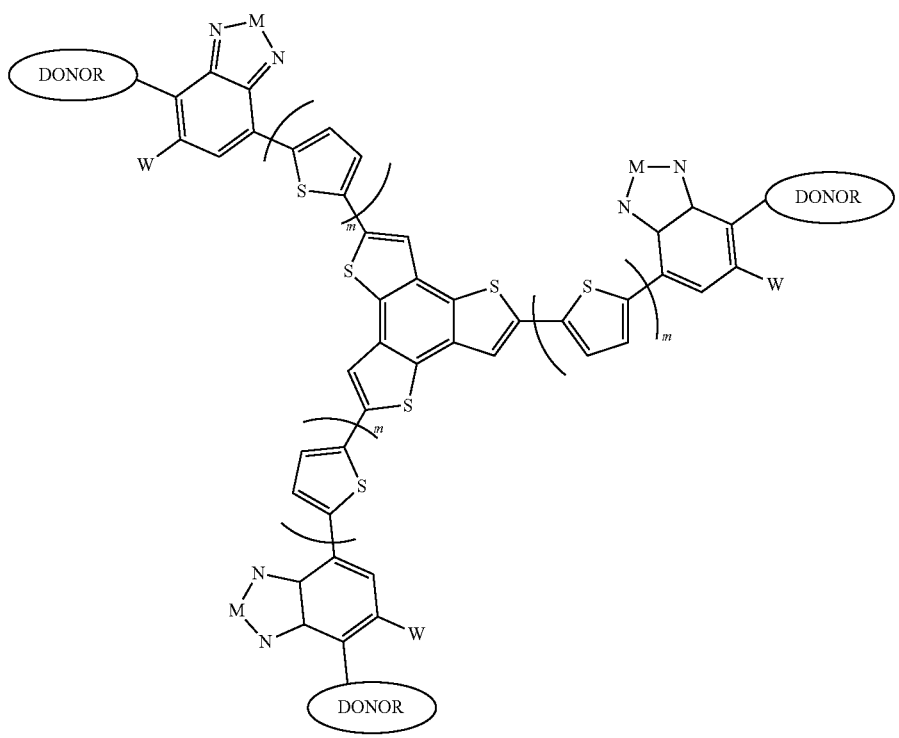

-continued

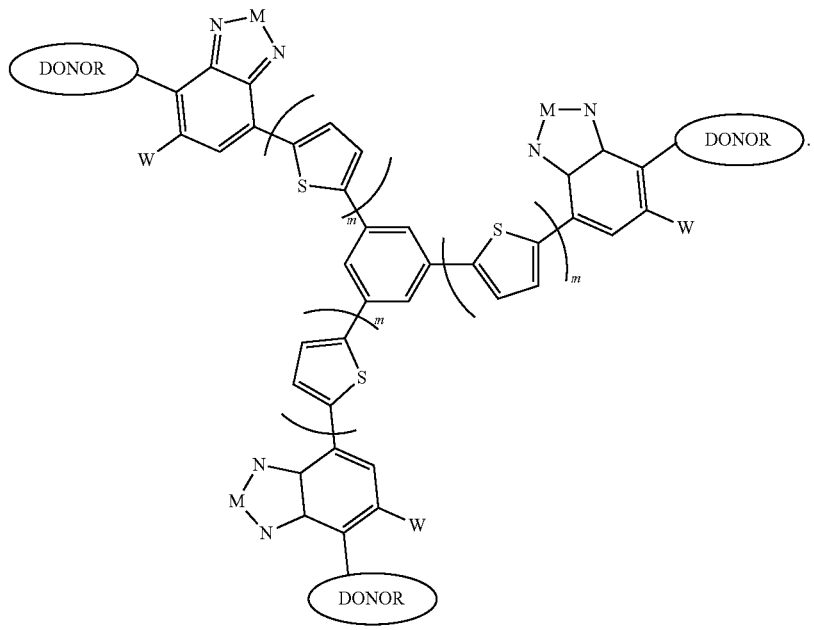

In the structures for Formula 9 and Formula 10 above:

M is selected from sulfur (S), oxygen (O), or N—$R_1$, where $R_1$ is H, $C_1$-$C_{30}$ alkyl or $C_6$-$C_{30}$ aryl;

W is selected from F, Cl, Br, I, —CN, —$CF_3$, —$CHF_2$, or —$CH_2F$; in a further embodiment, W is F;

n is an integer from 1 to 5 inclusive, and m is an integer from 0 to 5 inclusive. In another embodiment, n is 1. In another embodiment, n is 2. In another embodiment, n is 3. In another embodiment, n is 4. In another embodiment, n is 5. In another embodiment, m is 0. In another embodiment, m is 1. In another embodiment, m is 2. In another embodiment, m is 3. In another embodiment, m is 4. In another embodiment, m is 5; and where DONOR is as defined below.

In the structures for Formula 1-2-3-4-5, Formula 1, Formula 2, Formula 3, Formula 4, Formula 5, Formula 6-7-8, Formula 6, Formula 7, Formula 8, Formula 9-10, Formula 9, and Formula 10 above, each DONOR moiety is independently selected from the following group:

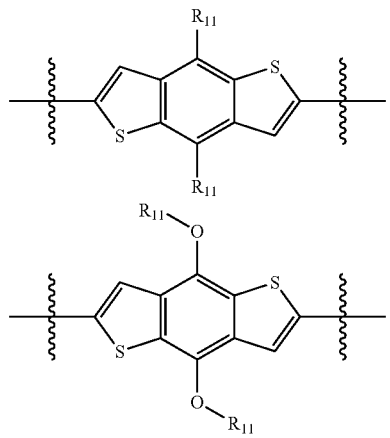

-continued

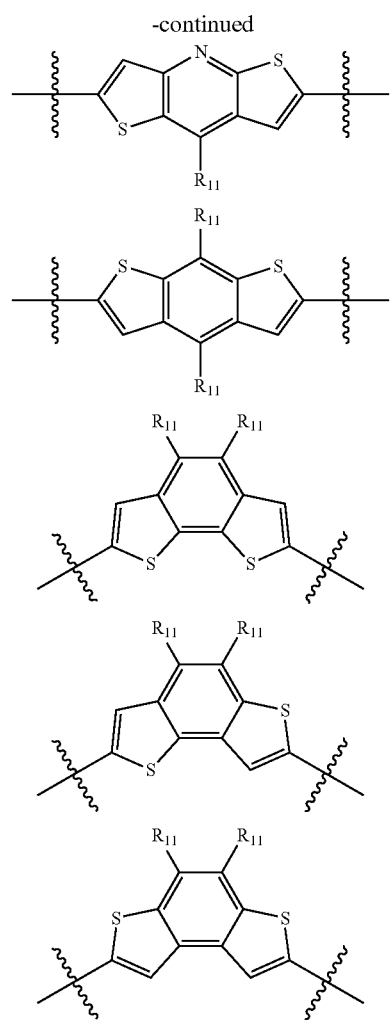

-continued
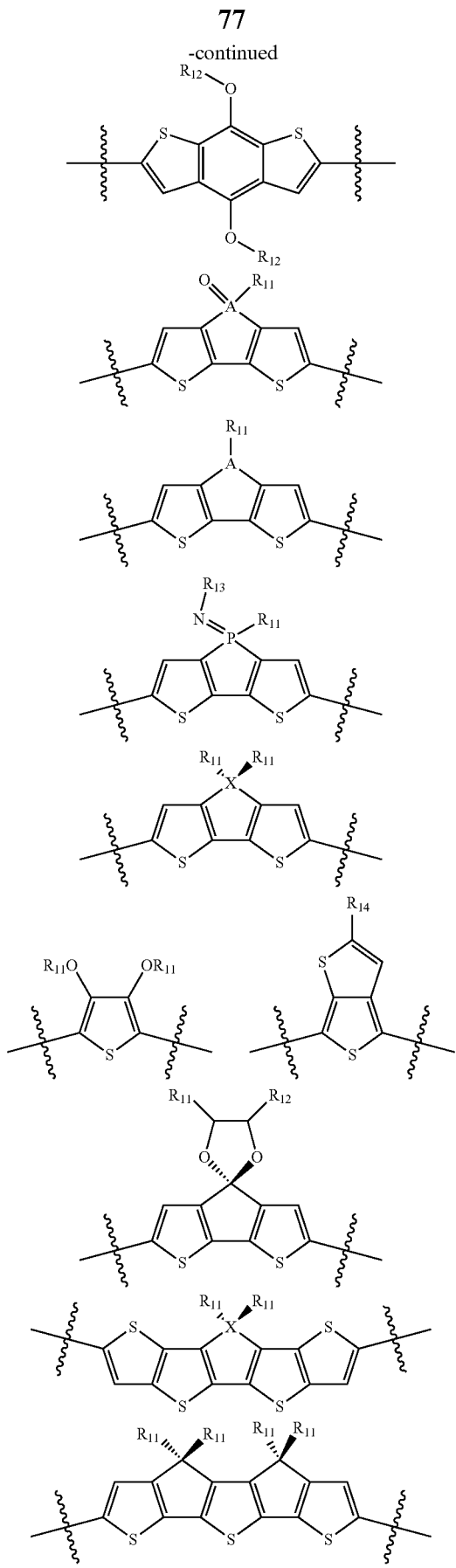
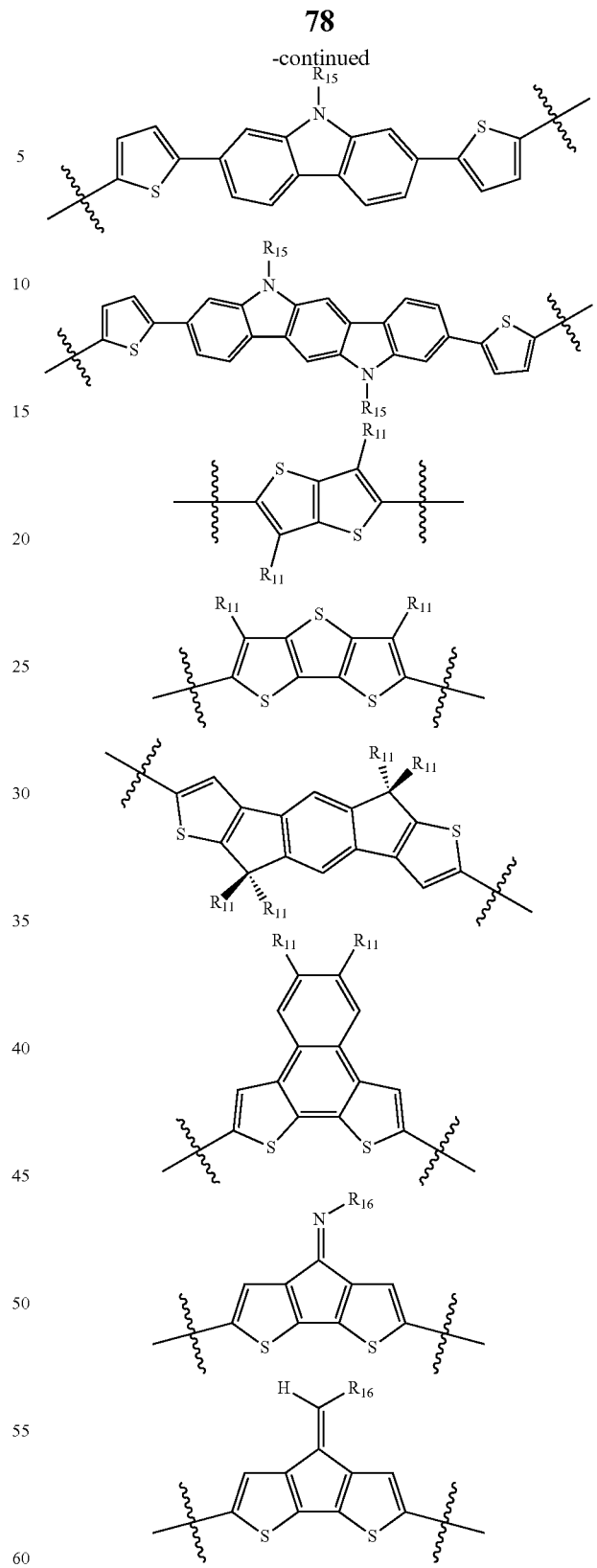
where X is C or Si;
A is N or P;
$R_{11}$ is selected from $C_1$-$C_{16}$ alkyl;
$R_{12}$ is selected from $C_1$-$C_{16}$ alkyl, $C_6$-$C_{20}$ unsubstituted aryl, or $C_6$-$C_{20}$ aryl substituted with one ore more groups selected from —F, $C_1$-$C_{20}$ alkyl, $C_1$-$C_{20}$ fluoroalkyl, —O—$C_1$-$C_{20}$ alkyl, or —$C_1$-$C_{20}$ fluoroalkyl;

$R_{13}$ is selected from $C_1$-$C_{16}$ alkyl or $C_6$-$C_{20}$ aryl;

$R_{14}$ is selected from $C_1$-$C_{16}$ alkyl, —O—$C_1$-$C_{16}$ alkyl, —C(=O)—O—$C_1$-$C_{16}$ alkyl, or —O—C(=O)—$C_1$-$C_{16}$ alkyl; and $R_{15}$ is selected from $C_1$-$C_{16}$ alkyl, $C_6$-$C_{20}$ unsubstituted aryl, or $C_6$-$C_2M$ aryl substituted with one or more groups selected from —F, $C_1$-$C_{20}$ alkyl, $C_1$-$C_{20}$ fluoroalkyl, —O—$C_1$-$C_{20}$ alkyl, or —$C_1$-$C_{20}$ fluoroalkyl; and $R_{16}$ is selected from $C_1$-$C_{16}$ alkyl, $C_6$-$C_{20}$ unsubstituted aryl, or $C_6$-$C_2M$ aryl substituted with one or more groups selected from —F, $C_1$-$C_{20}$ alkyl, $C_1$-$C_{20}$ fluoroalkyl, —O—$C_1$-$C_{20}$ alkyl, or —$C_1$-$C_{20}$ fluoroalkyl.

The DONOR structures are depicted as divalent; when a DONOR subunit is monovalent (as, for example, in Formula 9-10, Formula 9, and Formula 10 above), one valence is attached to the structure as depicted in the Formula, and one valence is terminated with H or $C_1$-$C_{20}$ alkyl, such as hexyl or 2-ethylhexyl.

In further embodiments, in the structure for Formula 1-2-3-4-5, each DONOR moiety is the same moiety.

In further embodiments, in the structure for Formula 1, each DONOR moiety is the same moiety.

In further embodiments, in the structure for Formula 2, each DONOR moiety is the same moiety.

In further embodiments, in the structure for Formula 3, each DONOR moiety is the same moiety.

In further embodiments, in the structure for Formula 4, each DONOR moiety is the same moiety.

In further embodiments, in the structure for Formula 5, each DONOR moiety is the same moiety.

In further embodiments, in the structure for Formula 6-7-8, each DONOR moiety is the same moiety.

In further embodiments, in the structure for Formula 6, each DONOR moiety is the same moiety.

In further embodiments, in the structure for Formula 7, each DONOR moiety is the same moiety.

In further embodiments, in the structure for Formula 8, each DONOR moiety is the same moiety.

In further embodiments, in the structure for Formula 9-10, each DONOR moiety is the same moiety.

In further embodiments, in the structure for Formula 9, each DONOR moiety is the same moiety.

In further embodiments, in the structure for Formula 10, each DONOR moiety is the same moiety.

In any of the foregoing embodiments, W can be F.

In additional embodiments, the invention embraces electronic and optoelectronic devices comprising a non-polymeric compound, said compound incorporating one or more groups of Formula A:

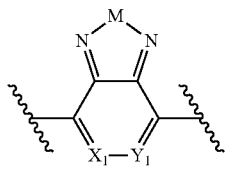

Formula A where said non-polymeric compound is an electron acceptor or is an electron donor in an active layer of the electronic or optoelectronic device, where M is selected from sulfur (S), oxygen (O), or N—$R_1$, where $R_1$ is H, $C_1$-$C_{30}$ alkyl or $C_6$-$C_{30}$ aryl, and either $X_1$ is CH and $Y_1$ is —C(W)—, or $X_1$ is —C(W)— and $Y_1$ is CH. In one embodiment, where more than one moiety of Formula A is present, M, $X_1$, and $Y_1$ for each moiety is chosen independently of the other moiety or moieties. In another embodiment, where more than one moiety of Formula A is present, M is the same for each moiety, $X_1$ is the same for each moiety, and $Y_1$ is the same for each moiety. In any of the foregoing embodiments, W can be F.

In additional embodiments, the invention embraces electronic and optoelectronic devices comprising a non-polymeric compound, said non-polymeric compound comprising a benzo[c][1,2,5]thiadiazole with an electron-withdrawing substituent W in the 5-position (5BTH), a benzo[c][1,2,5]oxadiazole with an electron-withdrawing substituent W in the 5-position (5BO), a 2H-benzo[d][1,2,3]triazole with an electron-withdrawing substituent W in the 5-position (5BTR), a 5-fluorobenzo[c][1,2,5]thiadiazole (FBTH), a 5-fluorobenzo[c][1,2,5]oxadiazole (FBO), or a 5-fluoro-2H-benzo[d][1,2,3]triazole (FBTR) moiety, wherein said non-polymeric compound is an electron acceptor or is an electron donor in an active layer of the electronic or optoelectronic device.

In additional embodiments, the invention embraces electronic and optoelectronic devices utilizing the compounds described above.

In additional embodiments, the invention embraces optoelectronic devices, such as organic solar cells, with the general device architecture using the compounds described above as a light harvesting electron donor, comprising:

1) a first hole-collecting electrode, optionally coated onto a transparent substrate;
2) an optional layer or layers adjacent to the first electrode, such as an electron-blocking, exciton-blocking, or hole-transporting layer;
3) a layer comprising a mixture of an electron acceptor, such as an organic electron acceptor or an inorganic electron acceptor, and an organic non-polymeric electron donor, said donor comprising one or more compounds selected from Formula I, Formula Ia, Formula Ib, Formula Ic, Formula II, Formula IIa, Formula IIb, Formula IIc, Formula III, Formula IIIa, Formula IIIb, Formula IIIc, Formula IIId, Formula IV-V, Formula IV, Formula IVa, Formula IVb, Formula V, Formula Va, Formula Vb, Formula VI-VII, Formula VI, Formula VIa, Formula VIb, Formula VII, Formula VIIa, Formula VIIb, Formula 1-2-3-4-5, Formula 1, Formula 2, Formula 3, Formula 4, Formula 5, Formula 6-7-8, Formula 6, Formula 7, Formula 8, Formula 9-10, Formula 9, or Formula 10;
4) an optional layer or layers such as hole-blocking, exciton-blocking, or electron-transporting layers; and
5) a second electron-collecting electrode.

In additional embodiments, the invention embraces optoelectronic devices, such as organic solar cells, with the general device architecture using the compounds described above as a light harvesting electron acceptor, comprising:

1) a first hole-collecting electrode, optionally coated onto a transparent substrate;
2) an optional layer or layers adjacent to the first electrode, such as an electron-blocking, exciton-blocking, or hole-transporting layer;
3) a layer comprising a mixture of an electron donor, such as an organic electron donor or an inorganic electron donor, and an organic non-polymeric electron acceptor material selected from Formula I, Formula Ia, Formula Ib, Formula Ic, Formula II, Formula IIa, Formula IIb, Formula IIc, Formula III, Formula IIIa, Formula IIIb, Formula IIIc, Formula IIId, Formula IV-V, Formula IV, Formula IVa, Formula IVb, Formula V, Formula Va, Formula Vb, Formula VI-VII, Formula VI, Formula VIa, Formula VIb, Formula VII, Formula VIIa, Formula VIIb, Formula 1-2-3-4-5, Formula 1, Formula 2, Formula 3, Formula 4, Formula 5, Formula 6-7-8, Formula 6, Formula 7, Formula 8, Formula 9-10, Formula 9, or Formula 10;

4) an optional layer or layers such as hole-blocking, exciton-blocking, or electron-transporting layers; and 5) a second electron-collecting electrode.

In additional embodiments, the invention embraces devices such as organic field-effect transistors with the general device architecture using the compounds described above as a hole transporting medium, comprising:

1) a dielectric substrate; in one embodiment, this dielectric substrate is $Si/SiO_2$;

2) an optional layer or layers adjacent the dielectric substrate, used to modify the surface energy of the dielectric and/or to facilitate deposition of the active layer;

3) an active layer comprising an organic non-polymeric hole transporting material selected from Formula I, Formula Ia, Formula Ib, Formula Ic, Formula II, Formula IIa, Formula IIb, Formula IIc, Formula III, Formula IIIa, Formula IIIb, Formula IIIc, Formula IIId, Formula IV-V, Formula IV, Formula IVa, Formula IVb, Formula V, Formula Va, Formula Vb, Formula VI-VII, Formula VI, Formula VIa, Formula VIb, Formula VII, Formula VIIa, Formula VIIb, Formula 1-2-3-4-5, Formula 1, Formula 2, Formula 3, Formula 4, Formula 5, Formula 6-7-8, Formula 6, Formula 7, Formula 8, Formula 9-10, Formula 9, or Formula 10; and 4) a metal electrode to facilitate charge injection and collection.

In additional embodiments, the invention embraces devices, such as organic field-effect transistors with the general device architecture using the compounds described above as an electron transporting medium, comprising:

1) a dielectric substrate; in one embodiment, this dielectric substrate is $Si/SiO_2$;

2) an optional layer or layers adjacent the dielectric substrate, used to modify the surface energy of the dielectric and/or to facilitate deposition of the active layer;

3) an active layer comprising an organic non-polymeric electron transporting material selected from Formula I, Formula Ia, Formula Ib, Formula Ic, Formula II, Formula IIa, Formula IIb, Formula IIc, Formula III, Formula IIIa, Formula IIIb, Formula IIIc, Formula IIId, Formula IV-V, Formula IV, Formula IVa, Formula IVb, Formula V, Formula Va, Formula Vb, Formula VI-VII, Formula VI, Formula VIa, Formula VIb, Formula VII, Formula VIIa, Formula VIIb, Formula 1-2-3-4-5, Formula 1, Formula 2, Formula 3, Formula 4, Formula 5, Formula 6-7-8, Formula 6, Formula 7, Formula 8, Formula 9-10, Formula 9, or Formula 10; and 4) a metal electrode to facilitate charge injection and collection.

DETAILED DESCRIPTION OF THE INVENTION

Definitions

Figure 1A:
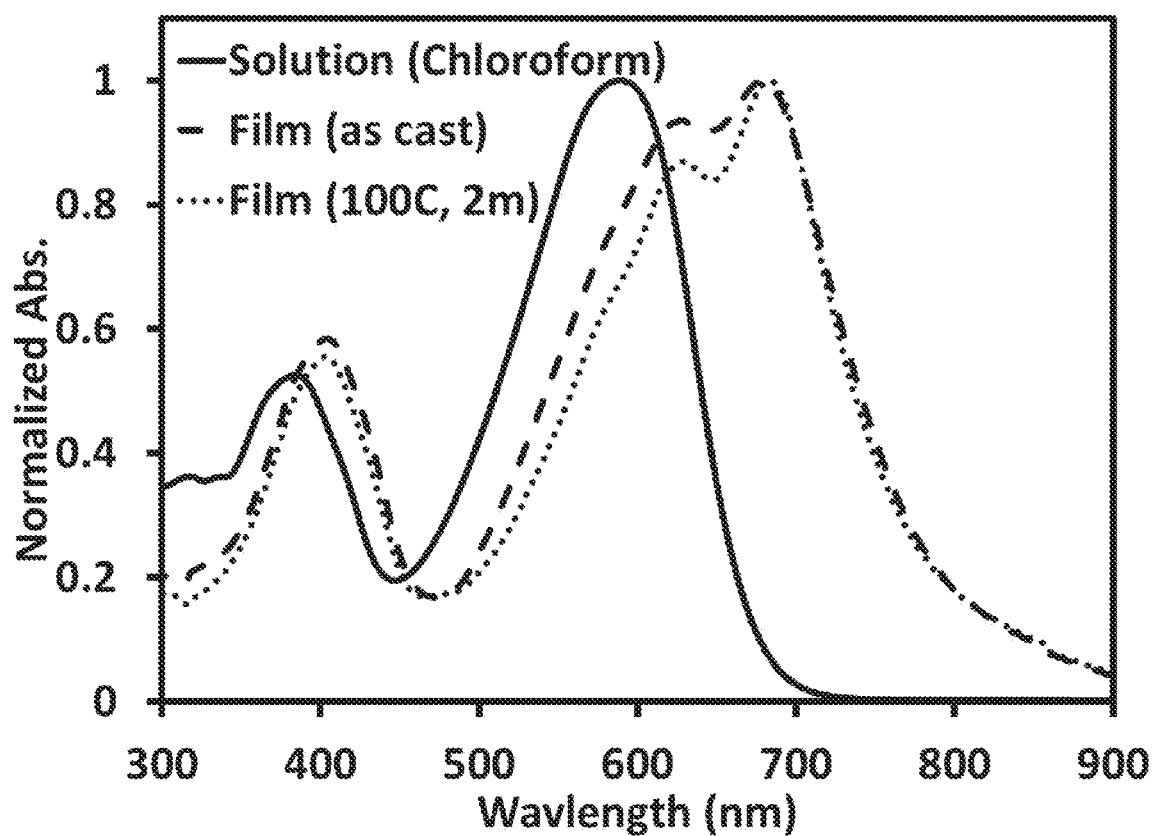
FIG. 1A shows the absorption spectra of p-DTS(FBTTh$_2$)$_2$ solution in chloroform, in a thin film, and in an annealed film.

"Alkyl" is intended to embrace a saturated linear, branched, cyclic, or a combination of linear and/or branched and/or cyclic hydrocarbon chain(s) and/or ring(s) having the number of carbon atoms specified, or if no number is specified, having 1 to 16 carbon atoms.

"Alkenyl" is intended to embrace a linear, branched, cyclic, or a combination of linear and/or branched and/or cyclic hydrocarbon chain(s) and/or ring(s) having at least one carbon-carbon double bond, and having the number of carbon atoms specified, or if no number is specified, having 2 to 16 carbon atoms.

"Alkynyl" is intended to embrace a linear, branched, cyclic, or a combination of linear and/or branched and/or cyclic hydrocarbon chain(s) and/or ring(s) having at least one carbon-carbon triple bond, and having the number of carbon atoms specified, or if no number is specified, having 2 to 19 carbon atoms, preferably 2 to 16 carbon atoms.

"Fluoroalkyl" indicates an alkyl group where at least one hydrogen of the alkyl group has been replaced with a fluorine substituent.

"Aryl" is defined as an optionally substituted aromatic ring system. Aryl groups include monocyclic aromatic rings, polyaromatic ring systems, and polycyclic aromatic ring systems containing the number of carbon atoms specified, or if no number is specified, containing six to thirty carbon atoms. In other embodiments, aryl groups may contain six to twenty carbon atoms, six to twelve carbon atoms, or six to ten carbon atoms. In other embodiments, aryl groups can be unsubstituted.

"Heteroaryl" is defined as an optionally substituted aromatic ring system. Heteroaryl groups contain the number of carbon atoms specified, and one or more heteroatoms (such as one to six heteroatoms, or one to three heteroatoms), where heteroatoms include, but are not limited to, oxygen, nitrogen, sulfur, and phosphorus. In other embodiments, heteroaryl groups may contain six to twenty carbon atoms and one to four heteroatoms, six to twelve carbon atoms and one to three heteroatoms, six to ten carbon atoms and one to three heteroatoms, or three to six carbon atoms and one to three heteroatoms. In other embodiments, heteroaryl groups can be unsubstituted.

"Polymer" or "polymeric molecule" is defined herein as a structure containing at least eight repeating units. A "non-polymeric" molecule is a molecule containing seven or fewer repeating units. Thus, monomers, dimers, trimers, tetramers, pentamers, hexamers, and heptamers are non-polymeric molecules for the purposes of this disclosure. Interruption of a repeating unit "resets" the count of subunits for the purposes of this disclosure; thus, for example, for a molecule such as Formula 6:

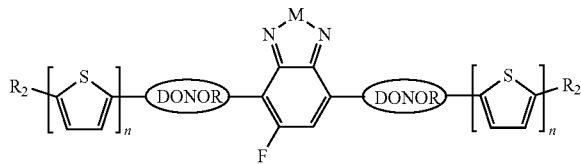

when n is 5, the molecule is considered to have two separate five-subunit pieces, that is, it is comprised of two pentathiophene units, and is not considered a decamer or 10-subunit polymer of thiophene.

Non-polymeric molecules typically have a discrete molecular weight, while polymeric molecules typically have a distribution of molecular weights due to varying numbers of monomers that are incorporated into the growing chain during polymerization. Thus, in one embodiment, a preparation of a non-polymeric molecule will be characterized by a single molecular weight (where the molecular weight is averaged only over isotopic variation due to differing isotopes such as hydrogen, deuterium, carbon-12, carbon-13, etc.) of about 90%, preferably 95%, more preferably 98%, still more preferably 99%, of the molecular species. In contrast, preparations of a polymeric molecule will typically have a distribution of molecular weights due to varying numbers of monomers in the final polymer, where the molecular weight is an average over each individual polymeric species present in a given preparation (measured in either number-average molecular weight or weight-average molecular weight).

Non-Reactive Electron Withdrawing Groups and Stabilization of Electronic Structure The current invention describes chromophores incorporating benzo[c][1,2,5]thiadiazoles with an electron-withdrawing substituent W in the 5-position (5BTH), benzo[c][1,2,5]oxadiazoles with an electron-withdrawing substituent W in the 5-position (5BO), 2H-benzo[d][1,2,3]triazoles (5BTR) with an electron-withdrawing substituent W in the 5-position (5BTR), 5-fluorobenzo[c][1,2,5]thiadiazoles (FBTH), 5-fluorobenzo[c][1,2,5]oxadiazoles (FBO), or 5-fluoro-2H-benzo[d][1,2,3]triazoles (FBTR). One example of such a molecule is the solution-processed small-molecule donor: 7,7'-(4,4-bis(2-ethylhexyl)-4H-silolo[3,2-b:4,5-b']dithiophene-2,6-diyl)bis(6-fluoro-4-(5'-hexyl-[2,2'-bithiophen]-5-yl)benzo[c][1,2,5]thiadiazole), p-DTS(FBTTh$_2$)$_2$, where "p" refers to the fluorine atoms oriented proximal to the donor core; see Scheme 1 for an outline of the synthesis of this molecule, and its structure.

Scheme 1. Synthetic scheme for p-DTS(FBTTh$_2$)$_2$.

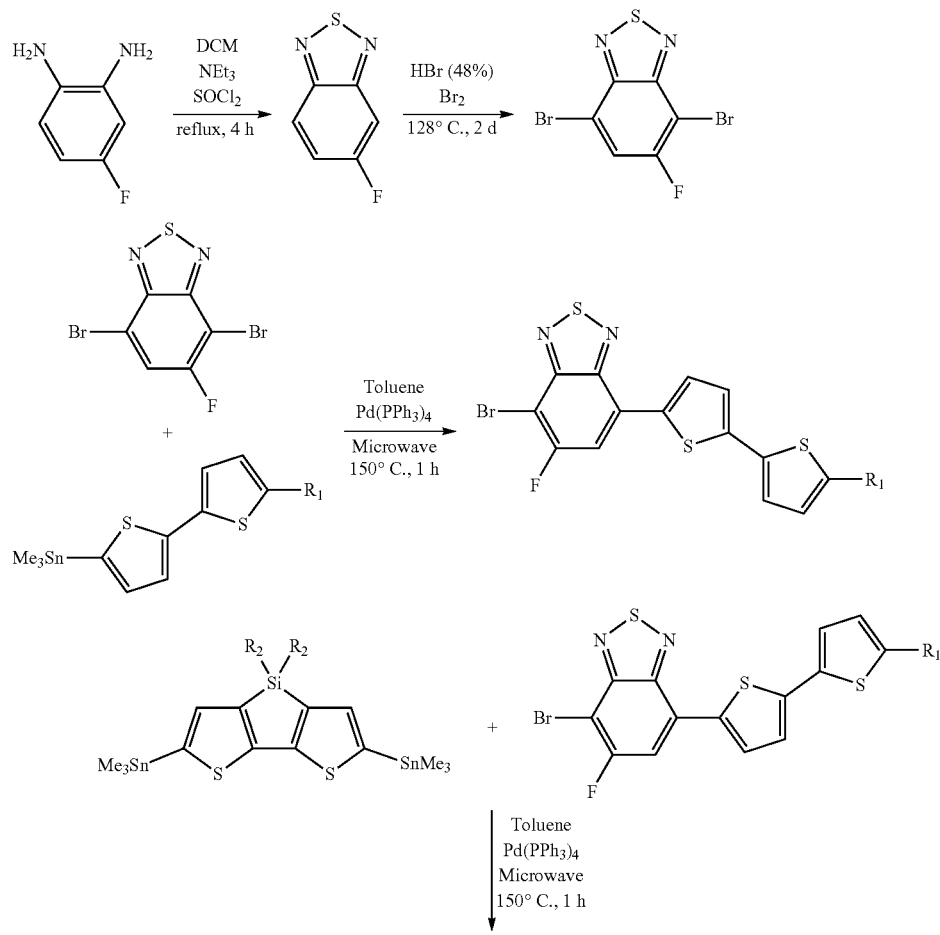

-continued

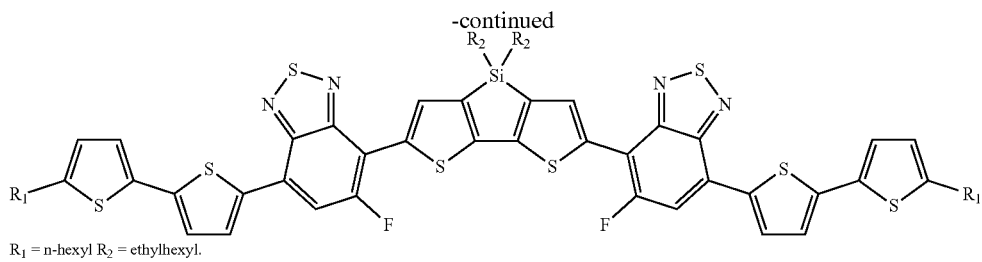

R₁ = n-hexyl R₂ = ethylhexyl.
See examples for further synthetic information.

The incorporation of a subunit of this type permits the manipulation of electronic levels without adding a reactive site, such as the pyridine nitrogen on pyridal[2,1,3]thiadiazole (PT)-type compounds, which is susceptible to protonation when deposited from acidic solution, or when used with materials having labile protons such as PEDOT:PSS. In addition to being an excellent candidate as an acceptor unit, the fluorine atom also imparts asymmetric reactivity to the corresponding dibromide compound (such as FBTHBr₂), which allows for facile synthetic access to the desired structure. Full synthetic details are provided in the Examples.

Optical properties were investigated using UV-visible absorption spectroscopy. In both solution (chloroform) and solid state, p-DTS(FBTTh₂)₂ exhibits broad low energy transitions with favorable overlap with the solar spectrum with $\lambda_{max}$ values of 590 nm (solution) and 678 nm (solid state), and $\lambda_{onset}$ values of 670 nm (solution) and 800 nm (solid state), corresponding to optical band gaps of 1.85 and 1.55 eV, respectively; see FIG. 1A. Thin film absorption exhibits a red-shifted spectrum as well as the development of vibronic structure in optical profiles, typical of ordered thin films. Solution cyclic voltammetry measurements indicated the highest occupied molecular orbital (HOMO) and lowest unoccupied molecular orbital (LUMO) were −5.12 and −3.34 eV, respectively, and line up appropriately with the frontier molecular orbitals of common fullerene acceptors.

To probe acid sensitivity, the solution absorption profiles of p-DTS(FBTTh₂)₂ (see Scheme 1, above) and d-DTS (PTTh₂)₂

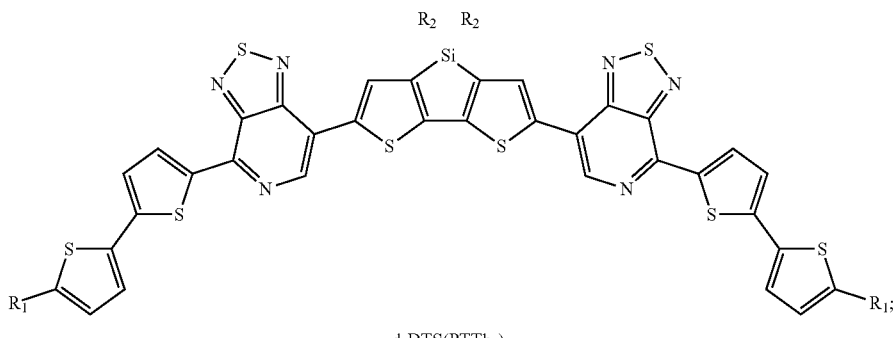

d-DTS(PTTh₂)₂

Figure 1B:
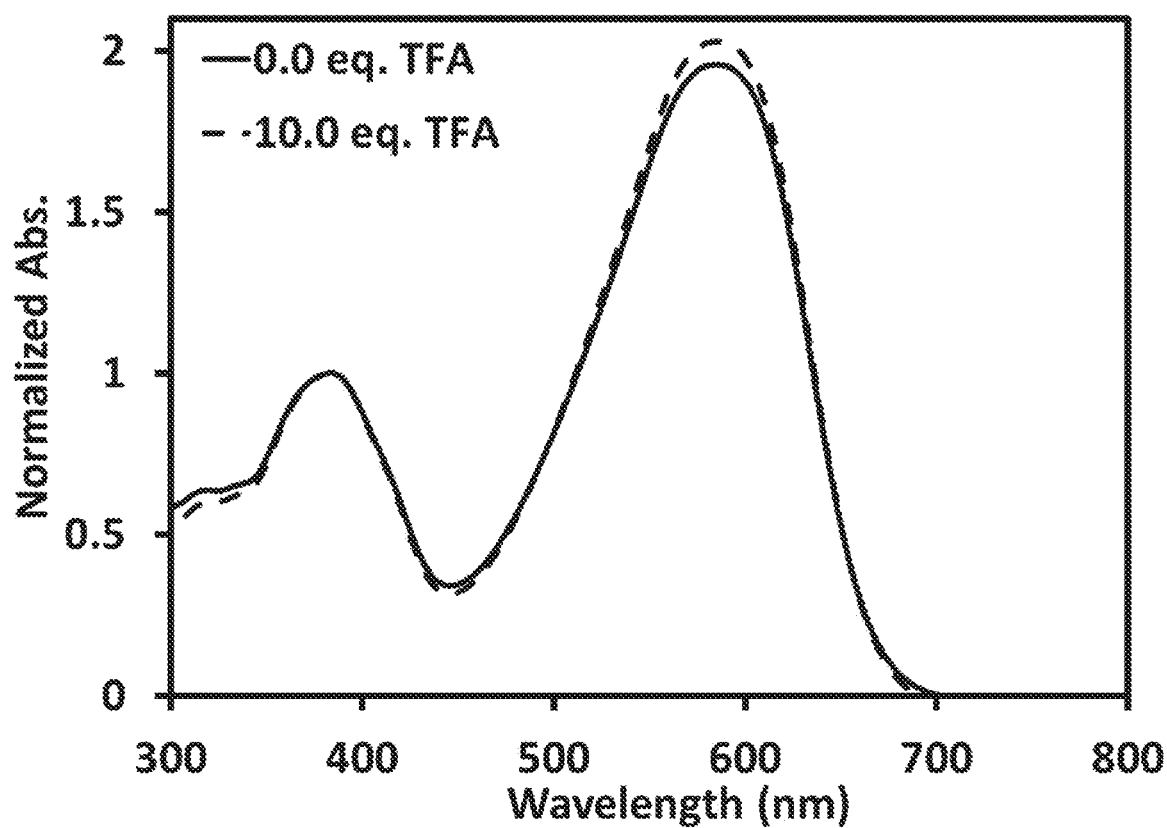
FIG. 1B shows the absorption spectra of p-DTS(FBTTh$_2$)$_2$ with various equivalents of trifluoroacetic acid in chloroform.
Figure 1C:
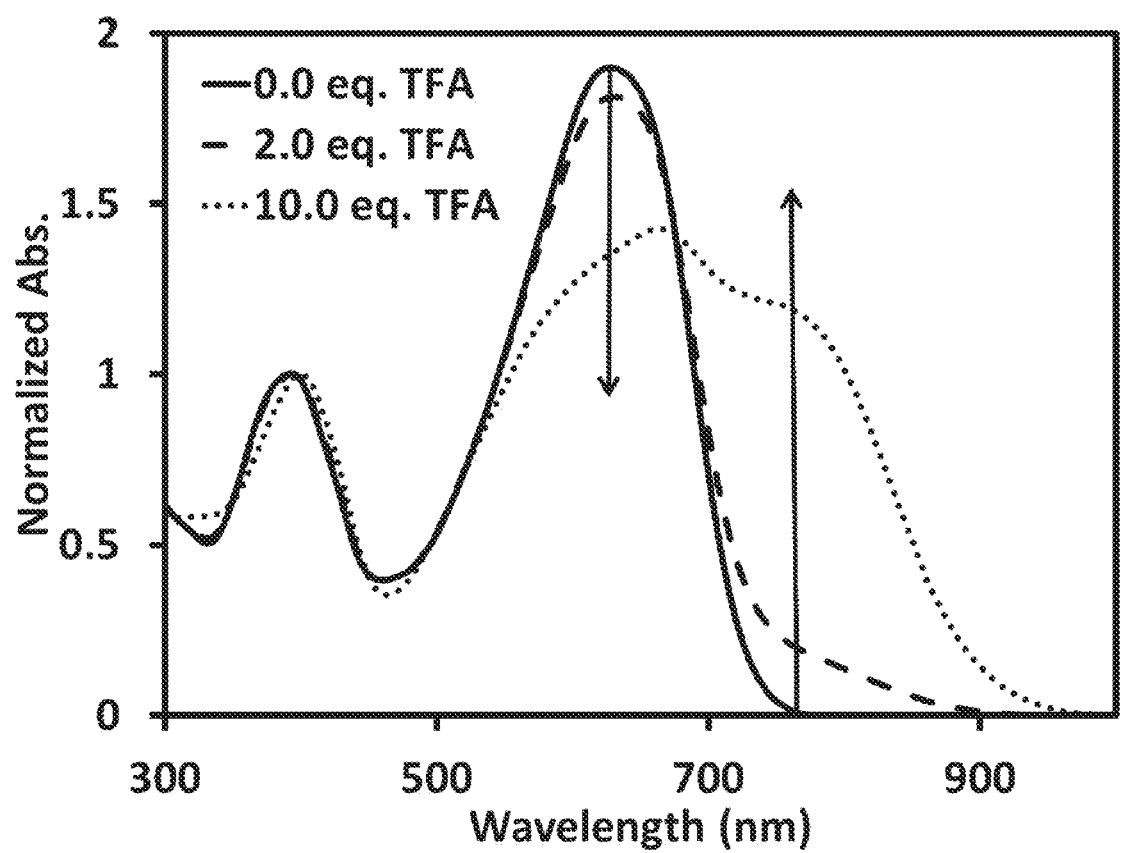
FIG. 1C shows the absorption spectra of d-DTS(PTTh$_2$)$_2$ with various equivalents of trifluoroacetic acid in chloroform.

R₁ = n-hexyl;
R₂ = 2-ethylhexyl a pyridine-containing analog, were monitored as function of concentration of trifluoroacetic acid. FIG. 1B shows that the absorption of p-DTS(FBTTh$_2$)$_2$ remains effectively unchanged with up to ten equivalents of acid. However, the pyridal analog shows significant changes in its absorption spectrum as soon as acid is introduced, as shown in FIG. 1C. The effect manifests as a new low-energy transition, suggesting that the chromophore backbone, where low-energy transition dipoles reside, is affected by the acid. These data indicate p-DTS(FBTTh$_2$)$_2$ is more resistant to acidity, and is suitable for use with PEDOT:PSS interlayers without significant losses in performance.

Figure 2:
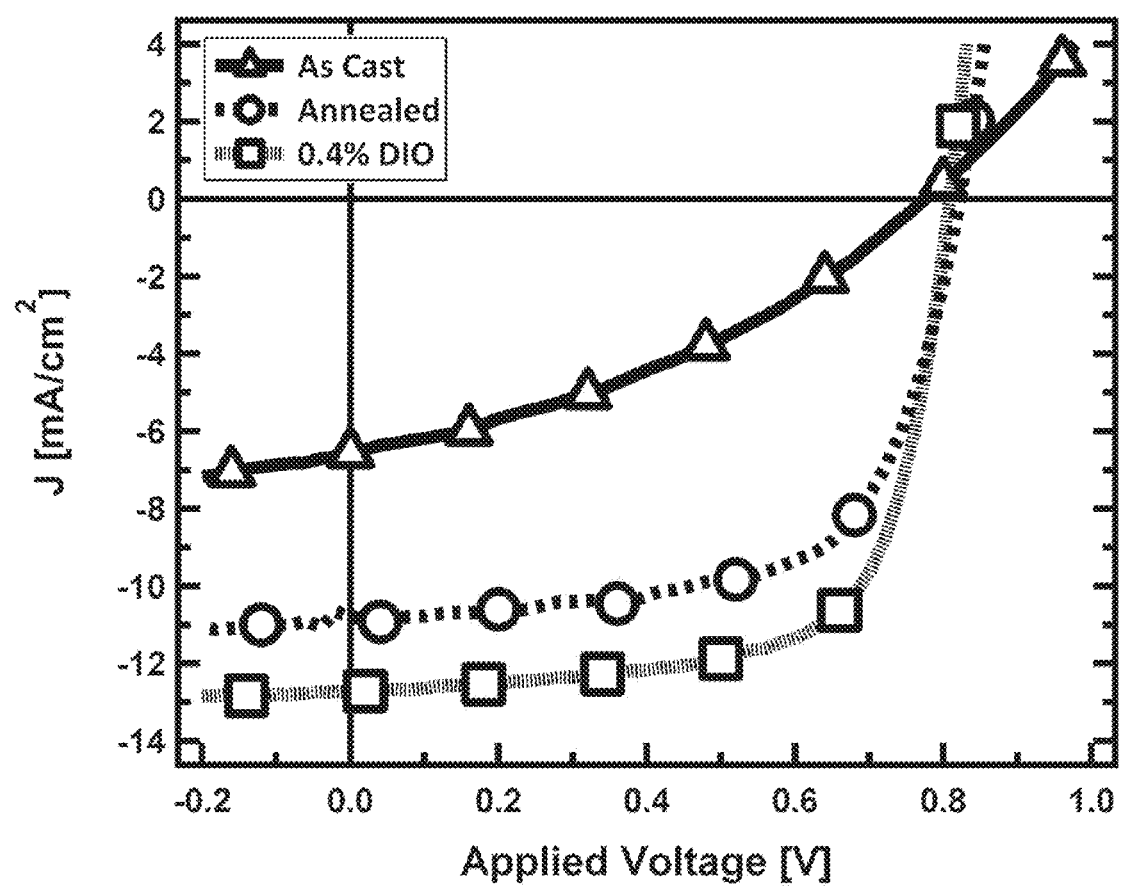
FIG. 2 shows current voltage characteristics of solar cells with an active layer comprised of p-DTS(FBTTh$_2$)$_2$ and $PC_{71}BM$ as cast, annealed and with 0.4% (v/v) diiodooctane solvent additive.
Figure 3:
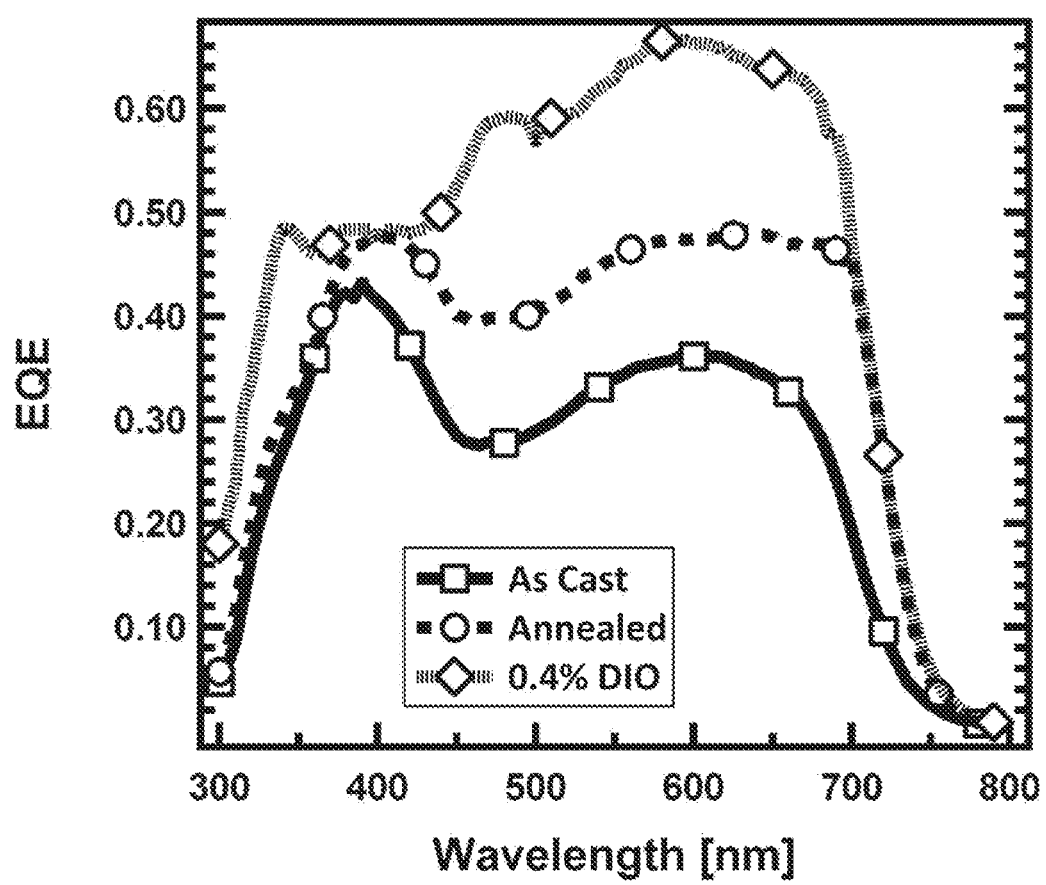
FIG. 3 shows the external quantum efficiency of the solar cells of FIG. 2.

Devices were fabricated with the general architecture of ITO/PEDOT:PSS/DTS(FBTTh$_2$)$_2$:PC$_{71}$BM/Ca/Al. Devices showed relatively poor performance as cast, with a open circuit voltage (V$_{OC}$) of 680 mV, short circuit current (J$_{SC}$) of 7.0 mA cm$^{-2}$, and a fill factor (FF) of 0.30, giving a power conversion efficiency (PCE) of 1.6%. Thermal annealing of the devices at 130° C. led to significant enhancement in V$_{OC}$ (820 mV), J$_{SC}$ (11.0 mA cm$^{-2}$), and FF (0.62), yielding a PCE of 5.6%. Processing with a small amount (0.4% v/v) of diiodooctane (DIO) with a low temperature anneal (70° C.) led to a slightly lower V$_{OC}$ (809 mV), but a significant increased current (12.8 mA cm$^{-2}$) and fill factor (0.68) yielding a PCE of 7.0%; the highest reported efficiency of a solution processed SM-BHJ solar cell known to the inventors as of filing. The current-voltage characteristics of the as-cast, thermally-annealed, and 0.4% diiodooctane-low temperature annealed cells are shown in FIG. 2. The external quantum efficiency of the cells is shown in FIG. 3.

Other General Synthetic Procedures

The various molecules as illustrated herein are readily accessible synthetically by adaptation of the foregoing synthesis of p-DTS(FBTTh$_2$)$_2$. For example, 5BTH moieties can be attached to a benzodithiophene core via the synthesis outlined in Scheme 2. Similar chemistry—that is, coupling of trimethylstannate derivatives of one moiety to bromo derivatives of another moiety—can be employed to assemble any of the various molecules described herein.

Scheme 2. Exemplary synthetic prodecure for a bis-5-BTH-benzodithiophene structure

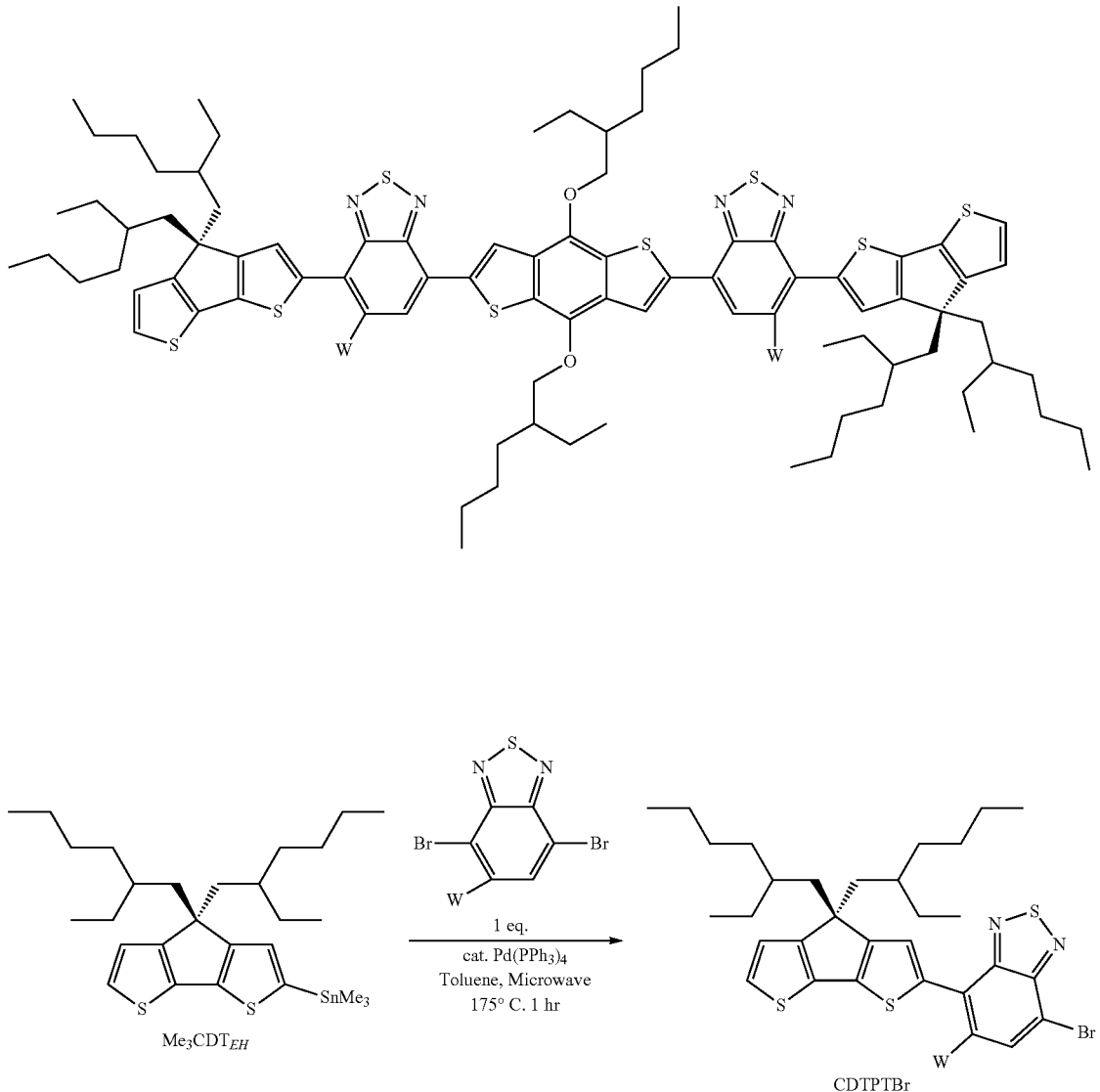

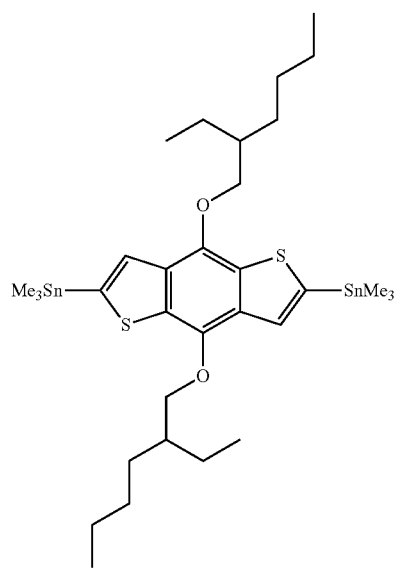
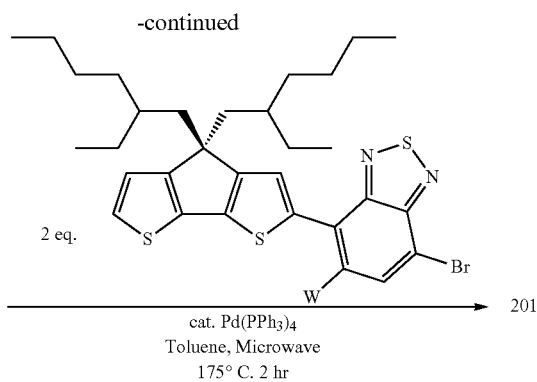

Small Molecule Chromophores

The current invention provides several advantages for preparation of optoelectronic devices. The organic materials described are non-polymeric allowing for synthesis and purification producers to be more repeatable than organic polymers. Unlike polymers, the organic materials described are discrete mono-disperse small molecules which allows for their exact structure to be known and reproduced. Synthesis of organic small molecule chromophores containing the 5BTH, 5BO, 5BTR, FBTH, FBO, or FBTR organic structures is straightforward, and methods used for the pyridalthiadiazole (PT, [1,2,5]thiadiazolo[3,4-c]pyridine) organic structure (see M. Leclerc et al. Journal of the American Chemical Society, 2008, 130, 732) can be adapted to make the 5BTH, 5BO, 5BTR, FBTH, FBO, and FBTR molecules (see also Welch et al., J. Materials Chemistry 21(34):12700-12709 (2011); U.S. Provisional Patent Appl. No. 61/416,251; and International Patent Appl. No. PCT/US2011/061963). The asymmetry of the 5BTH, 5BO, 5BTR, FBTH, FBO, and FBTR structures allows for facile mono-functionalization of the PT structure. The organic small molecule chromophores described herein have relatively planar structures allowing for good inter-chromophore interaction, which facilitates charge transfer and transport.

The compounds are readily handled in solution, as the organic small molecule chromophores described retain good solubility in many common organic solvents, and are soluble in aqueous solvents, including acidic aqueous solvents. This allows solution processing during the preparation of the optoelectronic devices.

While solution processing is preferred for its ease of handling and low cost, vapor deposition can also be used for the molecules, or mixtures of said molecules with other components, which are suitable for use in such a method (e.g., vacuum deposition, physical vapor deposition, chemical vapor deposition).

Device Architectures, Materials, and Fabrication

In one embodiment, the optoelectronic device of the invention comprises the following layers:
  a) a first hole-collecting electrode, optionally coated onto a transparent substrate;
  b) an optional layer or layers adjacent to the first electrode, such as an electron-blocking, exciton-blocking, or hole-transporting layer;
  c) a layer comprising a mixture of an electron donor of the general Formula I-VII and an electron acceptor (donor:acceptor);
  d) an optional layer or layers such as hole-blocking, exciton-blocking, or electron-transporting layers; and
  e) a second electron-collecting electrode.

Typically, the first electrode can be transparent, allowing light to enter the device, but in some embodiments, the second electrode can be transparent. In some embodiments, both electrodes are transparent.

Typically, the first electrode (layer "a") is deposited onto a substrate, and the device is fabricated by subsequent deposition of layers "b" (if present), "c", "d" (if present), and "e". However, the second electrode "e" can be deposited onto a substrate, with subsequent deposition of layers "d" (if present), "c", "b" (if present), and "a".

In another embodiment, the optoelectronic device of the invention comprises the following layers:
  a) indium tin oxide (ITO) coated onto a transparent substrate (a first electrode), where the transparent substrate can be glass, plastic, or any other transparent material compatible with ITO,
  b) poly(3,4-ethylene dioxythiophene:poly(styrenesulfonate) (PEDOT:PSS) or a electron-blocking, exciton-blocking, or hole-transporting metal oxide, including, but not limited to, MoO3,
  c) a mixture of electron-donating chromophores of the general Formula I-VII, and an electron-acceptor (donor:acceptor), and
  e) a metal electrode (a second electrode); where layer (d) in the previous embodiment is absent.

Typically, the first electrode (layer "a") is deposited onto the substrate, and the device is fabricated by subsequent deposition of layers "b", "c", and "e". However, the second electrode "e" can be deposited onto a substrate, with subsequent deposition of layers "c", "b", and "a".

The 5BTH, 5BO, 5BTR, FBTH, FBO, or FBTR electron donors or electron acceptors can be used in tandem solar cells, such as those disclosed in US 2009/0126779. Tandem solar cells are arranged so that light which is not absorbed by a first solar cell passes to a second solar cell, where the second solar cell typically has a smaller bandgap than the first solar cell in order to absorb electromagnetic radiation that cannot be usefully absorbed by the first solar cell. In an example of a tandem photovoltaic device, the device can comprise a first cell and a second cell arranged in tandem. The first cell is configured to receive incident electromagnetic radiation and includes a first charge separating layer having a first semiconducting polymer adapted to create electric charge carriers generated by electromagnetic radiation. The second cell is configured to receive electromagnetic radiation passing out of the first cell in a light propagation path. The second cell includes a second charge separating layer having a second semiconducting polymer adapted to create electric charge carriers generated by electromagnetic radiation. A layer separates the two cells, such as a titanium oxide layer which is interposed between the first and second cells. The titanium oxide layer can be substantially amorphous and can have a general formula of $TiO_x$ where x is a number of about 1 to about 1.96; that is, the titanium oxide layer can be sub-stoichiometric titanium dioxide, or amorphous sub-stoichiometric titanium dioxide.

Passivating layers, such as those disclosed in US 2007/0221926 and US 2007/0169816, can be incorporated into devices using the 5BTH, 5BO, 5BTR, FBTH, FBO, or FBTR electron donors or electron acceptors.

Optical spacer layers, such as those disclosed in US 2006/0292736, can also be employed in devices using the 5BTH, 5BO, 5BTR, FBTH, FBO, or FBTR electron donors or electron acceptors.

In one configuration, where light passes though a transparent first electrode (such as ITO-coated glass), it is absorbed by the donor:acceptor mixture, which results in the separation of electrical charges and migration of the charges to the electrodes, yielding a usable electrical potential.

The first electrode can be made of materials such as indium-tin oxide, indium-magnesium oxide, cadmium tin-oxide, tin oxide, aluminum- or indium-doped zinc oxide, gold, silver, nickel, palladium and platinum. Preferably the first electrode has a high work function (4.3 eV or higher). Preferably, the first electrode is transparent.

The optional layer adjacent to the first electrode is preferably polystyrenesulfonic acid-doped polyethylenedioxythiophene (PEDOT:PSS). Other hole transporting materials, such as polyaniline (with suitable dopants), or N,N'-diphenyl-N,N'-bis(3-methylphenyl)[1,1'-biphenyl]-4,4'-diamine (TPD), nickel oxide, can be used. Electron-blocking, exciton-blocking, or hole-transporting metal oxides, such as $MoO_3$, $MoO_{3-x}$, $V_2O_{5-x}$, NiO, $Ta_2O_5$, $Ag_2O$, CuO, $Cu_2O$, $CrO_{3-x}$, and $WO_3$, where x is between 0.01 and 0.99, more preferably between 0.1 and 0.9, can be used as materials between the hole-transporting electrode and the active layer. Other suitable materials are described in Greiner, Mark T. et al., "Universal energy-level alignment of molecules on metal oxides," Nature Materials, DOI: 10.1038/NMAT3159 (Nov. 6, 2011).

One method of fabricating the optoelectronic device is as follows: A conductive, transparent substrate is prepared from commercially available indium tin oxide-coated glass and polystyrenesulfonic acid doped polyethylenedioxythiophene using standard procedures. A solution containing a mixture of the donor and acceptor materials is prepared so that the ratio of donor to acceptor is between 1:99 and 99:1 parts by mass; more preferably between 3:7 and 7:3 parts by mass. The overall concentration of the solution may range between 0.1 mg/mL and 100 mg/mL, but is preferably in the range of 10 mg/mL and 30 mg/mL. In one embodiment of the invention, 5BTH, 5BO, 5BTR, FBTH, FBO, or FBTR non-polymeric molecules are used that have a solubility of at least about 0.1 mg/mL in an organic solvent, 1 mg/mL in an organic solvent, 5 mg/mL, 10 mg/mL in an organic solvent, 30 mg/mL in an organic solvent, or 100 mg/mL in an organic solvent. The organic solvent can be selected from chloroform, toluene, chlorobenzene, dichloromethane, tetrahydrofuran, or carbon disulfide.

The electron acceptor is preferably [6,6]-phenyl C61-butyric acid methyl ester (PCBM), but may be a different fullerene (including, but not limited to, C71-PCBM), a tetracyanoquinodimethane, a vinazene, a perylene tetracarboxylic acid-dianhydride, a perylene tetracarboxylic acid-diimide, an oxadiazole, carbon nanotubes, or any other organic electron acceptor, such as those compounds disclosed in U.S. 2008/0315187.

In other embodiments, the electron acceptor is an inorganic acceptor selected from $TiO_2$ (titanium dioxide), $TiO_x$ (titanium suboxide, where x<2) and ZnO (zinc oxide). The titanium dioxide can be anatase, rutile, or amorphous. A titanium dioxide layer can be prepared by depositing a sol-gel precursor solution, for example by spincasting or doctorblading, and sintering at a temperature between about 300° C. and 500° C. When an inorganic layer is used, component (c) of the optoelectronic device described above can be comprised of a layer of electron-donating chromophores of the general Formula I-VII and an inorganic electron-acceptor layer. Alternatively, the inorganic material can be dispersed in the electron-donating chromophores to create a single layer. Preparation of $TiO_2$ for use in solar cells is described in Brian O'Regan & Michael Grätzel, Nature 353:737 (1991) and Serap Günes et al., 2008 Nanotechnology 19 424009.

When titanium suboxide according to the formula $TiO_x$ where x<2, is used, x is preferably 1<x<1.98, 1.1<x<1.9, 1.2<x<1.8, or 1.3<x<1.8. X in the formula $TiO_x$ can be <2, <1.98, <1.9, <1.8, <1.7, or <1.6.

Useful solvents include chloroform, toluene, chlorobenzene, dichloromethane, tetrahydrofuran, and carbon disulfide. However, the solvent used may be any solvent which dissolves or partially dissolve both donor and acceptor materials and has a non-zero vapor pressure.

The solution of donor and acceptor is deposited by spin casting, doctor-blading, ink-jet printing, roll-to-roll coating, slot-dye coating, gravure coating, or any process which yields a continuous film of the donor-acceptor mixture such that the thickness of the film is within the range of 10 to 1000 nm, more preferably between 50 and 150 nm.

In certain embodiments, the layer of the donor and acceptor is cast from a solution comprising a solvent and the electron donor and the electron acceptor. The solvent can comprise chloroform, thiophene, trichloroethylene, chlorobenzene, carbon disulfide, a mixture of any of the foregoing solvents or any solvent or solvent mixture that dissolves both the donor and acceptor organic small molecule. The solvent can also include processing additives, such as those disclosed in US Patent Application Publication Nos. 2009/0032808, 2008/0315187, or 2009/0108255. For example, 1,8-diiodooctane (DIO) can be added to the solvent/donor/acceptor mixture in an amount of 0.1-10% by volume. The additive, such as 2% DIO, can be added to any organic solvent used to cast the layer of donor/acceptor, such as chloroform. The solvent can also include doping agents such as molybdenum trioxide ($MoO_3$). For example, $MoO_3$ can be added to the solvent/donor/acceptor mixture in an amount of 0.1-10% by volume.

An additional layer or layers of material (i.e., the layer(s) adjacent to the second electrode) may optionally be deposited on top of the donor-acceptor film in order to block holes or excitons, act as an optical buffer, or otherwise benefit the electrical characteristics of the device. 2,9-dimethyl-4,7-diphenyl-1,10-phenanthroline can act as a hole-blocking or exciton-blocking material, while 4,4',4''-tris[N-(3-methylphenyl)-N-phenylamino]triphenylamine and polyethylene dioxythiophene can act as exciton-blocking materials. Other materials that can be used between the second electrode and the active layer are titanium suboxide, ZnO, $Cs_2CO_3$, and $ZrO_3$. Additional materials suitable for use are described in Greiner, Mark T. et al., "Universal energy-level alignment of molecules on metal oxides," Nature Materials, DOI: 10.1038/NMAT3159 (Nov. 6, 2011).

Finally, an electrode, such as a metal electrode, is deposited on top of the structure by thermal evaporation, sputtering, printing, lamination or some other process. Conducting metal oxides, such as indium tin oxide, zinc oxide, or cadmium oxide, can also be used as electrodes, as well as conducting organic materials, such as electrodes comprising graphene. For metal electrodes, the metal is preferably aluminum, silver or magnesium, but may be any metal. Nanowires such as silver nanowires can also be used. If a transparent electrode is desired, very thin metallic sheets of metals can also be used. In some embodiments, the device is annealed before and/or after evaporation of the metal electrode.

Hole and electron mobilities are important parameters to consider in the fabrication/function of bulk heterojunction solar cells. For optimal device performance, a balance in the mobility of both charge carriers is desirable. Preferably, the electron and hole mobilities are both on the order of $10^{-4}$ $cm^2$/Vs or higher. More preferably, the electron mobilities are on the order of $10^{-3}$ $cm^2$/Vs or higher. In some embodiments, the electron mobilities are on the order of $10^{-4}$ $cm^2$/Vs or higher, and the hole mobilities are between $10^{-8}$ $cm^2$/Vs and $10^{-4}$ $cm^2$/Vs or higher. In other embodiments, the electron mobilities are on the order of $10^{-3}$ $cm^2$/Vs or higher, and the hole mobilities are between $10^{-1}$ $cm^2$/Vs and $10^{-4}$ $cm^2$/Vs or higher.

Optoelectronic devices of the present invention have excellent photovoltaic properties. In some embodiments, the power conversion efficiency (PCE) is at least 0.5%, at least 1.0%, at least 2.0%, or at least 3.0%. In some embodiments, the short circuit current density is greater than 3.0 mA/$cm^2$, and preferably greater than 8 mA/$cm^2$. In some embodiments, the open circuit voltage is between 0.3 and 1.0 V or higher. In some embodiments, the device exhibits an external quantum efficiency of approximately 35% or greater between 300 and 800 nm.

The morphological properties of the donor:acceptor films can be measured using atomic force microscopy or other surface-sensitive techniques. Preferably, the films will have a root-mean-squared surface roughness of less than 1.0 nm, more preferably less than 0.5 nm.

Inverted Device Architecture

In some cases, it can be advantageous to use inverted device architecture, where the substrate act as a cathode, while the top electrode acts as the anode. For example, using the substrate to collect electrons can allow a stable, high work function metal such as gold or nickel to be used as the top electrode. This can be achieved by modifying the work function of the substrate or using an n-type substrate. Inverted device architecture is described in, for example, Hau et al. (2010) "A Review on the Development of the Inverted Polymer Solar Cell Architecture," Polymer Reviews 50(4):474-510, in Jen et al., US 2009/0188558, and in Nguyen et al. US 2010/0326525 (see FIG. 19B).

In an example of a device using standard architecture, photo-generated holes travel to an ITO substrate while photo-generated electrons travel to a top electrode consisting of a relatively low work-function metal such as Al. In a device using inverted architecture, the charge carriers flow in the opposite direction, where electrons travel to the ITO substrate while holes travel to the top electrode and are collected by a relatively high work function metal such as Au. This configuration has the advantage that a relatively stable metal is used as the top electrode, which can increase the lifetime of the device.

For embodiments of the devices using an inverted device architecture, the first electrode can comprise Au or another material having a work function higher than the work function of the second electrode, while the second electrode can comprise an ITO substrate modified using a self-assembled monolayer of 3-aminopropyltrimethoxysiloxane or another material having a work function lower than the work function of the first electrode.

The compounds of the invention can also be used to make inverted tandem solar cells, such as a cell having the layers of a transparent substrate, a transparent conductor, an electron injection/transport layer, an active layer with a wider band gap organic semiconductor, a hole injection/transport layer, an electron injection/transport layer (which facilitates recombination between the front and back cells), an active layer with a smaller band gap organic semiconductor, a hole injection/transport layer, and atop metal electrode. An example of a cell using this architecture is described in Dou et al., Nature Photonics 6:180-185 (2012).

EXAMPLES

General Experimental Procedures

Material Synthesis: Compound 5,5'-Bis(trimethylstannyl)-3,3'-di-2-ethylhexylsilylene-2,2'-bithiophene {DTS $(SnMe_3)_2$} and 5'-Hexyl-2,2'-bithiophene-5-trimethylstannane were prepared by methods similar to those reported in the literature (Coffin, R.; Peet, J.; Rogers, J.; Bazan, G. C. Nat. Chem. 2009; 1(8):657-661). Compound 5,5'-dibromo-3,3'-di-2-ethylhexylsilylene-2,2'-bithiophene (DTS-$Br_2$) was purchased from Luminescence Technology Corp. (Lumtec) and used as received. Compound 5'-Hexyl-2,2', 2''-trithiophene-5-trimethylstannane was prepared similarly as in the literature (Leroy, J., Boucher, N., Sergeyev, S., Sferrazza, M. and Geerts, Y. H. Eur. J. Org. Chem. 2007, 1256-1261). Stannanes reported that were not purchased were prepared according to literature procedure (Coffin, R.; Peet, J.; Rogers, J.; Bazan, G. C. Nat. Chem. 2009; 1(8): 657-661).

Preparations were carried out on a bench top or under an atmosphere of dry, oxygen-free nitrogen employing both Schlenk line techniques and a Vacuum Atmospheres inert atmosphere glove box. Deuterated chloroform ($CDCl_3$) was purchased from Cambridge Isotopes Laboratory and used as received. All reactants and reagents are commercially available and used as received, unless otherwise noted.

Compound 5,5'-Bis(trimethylstannyl)-3,3'-di-2-ethylhexylsilylene-2,2'-bithiophene {DTS$(SnMe_3)_2$} and 5'-Hexyl-2,2'-bithiophene-5-trimethylstannane were prepared by methods similar to those reported in the literature (Coffin, R.; Peet, J.; Rogers, J.; Bazan, G. C. Nat. Chem. 2009; 1(8):657-661). Compound 5,5'-dibromo-3,3'-di-2-ethylhexylsilylene-2,2'-bithiophene (DTS-$Br_2$) was purchased from Luminescence Technology Corp. (Lumtec) and used as received. Compound 5'-Hexyl-2,2',2"-trithiophene-5-trimethylstannane was prepared similarly as in the literature (Leroy, J., Boucher, N., Sergeyev, S., Sferrazza, M. and Geerts, Y. H. Eur. J. Org. Chem. 2007, 1256-1261). Stannanes reported that were not purchased were prepared according to literature procedure (Coffin, R.; Peet, J.; Rogers, J.; Bazan, G. C. Nat. Chem. 2009; 1(8):657-661).

NMR: $^1$H and $^{13}$C nuclear magnetic resonance (NMR) spectroscopy spectra were recorded on a Varian VNMRS 600 MHz Spectrometer at 25° C. unless otherwise noted. $^1$H and $^{13}$C NMR spectra are referenced to SiMe$_4$ using the residual solvent peak impurity of the given solvent. Chemical shifts are reported in ppm and coupling constants in Hz as absolute values. 2D NOE $^1$H-$^1$H correlation experiments were completed on a Bruker Avance-500 MHz spectrometer at 25° C. for assignment of fluorine regiochemistry.

UV-vis: UV-visible spectroscopy were recorded using either a Beckman Coulter DU 800 series or Perkin Elmer Lambda 750 spectrophotometer at room temperature unless otherwise noted. All solution UV-vis experiments were run in CHCl$_3$. Films were prepared by spin-coating CHCl$_3$ or chlorobenzene solutions onto glass substrates. Films were annealed directly on a hot plate for 2 minutes.

CHN: Combustion analyses were performed by the MSI analytical lab at the University of California, Santa Barbara.

Mass Spectroscopy: Full scan, low resolution FD mass spectroscopy was carried out at the Department of Chemistry Spectroscopy Facility, University of California, Santa Barbara.

DSC: Differential scanning calorimetry (DSC) was determined using a TA Instruments DSC (Model Q-20) with about 5 mg samples at a rate of 10° C./min in the temperature range of 0 to 300° C., unless otherwise stated.

Electrochemistry: All electrochemical measurements were performed using CHI instrument model 730B in a standard three-electrode, one compartment configuration equipped with Ag/AgCl electrode, Pt wire and Glassy carbon electrode (dia. 3 mm), as the pseudo reference, counter electrode and working electrode respectively. Glassy carbon electrodes were polished with alumina. The cyclic voltammetry (CV) experiments were performed in anhydrous dichloromethane solution with ~0.1 M tetrabutylammonium hexafluorophosphate (TBAPF$_6$) as the supporting electrolyte at scan rate 50 mV/s unless otherwise stated. All electrochemical solutions were purged with dry Ar for 15 minutes to deoxygenate the system. Solution CV measurements were carried out with a small molecule concentration of ~1 mg/mL in CH$_2$Cl$_2$. Ferrocene was used as an internal standard. The HOMO and LUMO levels were obtained by correlating the onsets ($E_{ox}^{Fc/Fc+}$, $E_{rd}^{Fc/Fc+}$) to the normal hydrogen electrode (NHE), assuming HOMO of Fc/Fc$^+$ to be 4.88 eV.

Solubility Measurements: The solubility in a given solvent was determined as follows: A saturated solution (~30 mg/mL) was stirred overnight at 49° C. and then allowed to stand still for 24 hours. The slurry was then filtered through a 0.45 µm PVDF filter. The filtrate is assumed to be a saturated solution. A 30 µL aliquot was then diluted to 3 mL with chloroform. The UV-vis absorption spectrum was acquired and the concentration determined using a standard calibration curve. The calibration curve was prepared by measuring the absorbance of 5 solutions in chloroform with known concentrations and plotting $\lambda_{max}$ vs concentration, wherein a linear relationship was observed.

Calculations: All calculations were performed using the Gaussian 03 program. Optimized gas-phase ground state structures were calculated at the density functional theory (DFT) level, using the hybrid B3LYP exchange-correlation functional and the split-valence 6-31G(d,p) basis set, i.e., B3LYP/6-31G(d,p). Frequency calculations were carried out to ensure that the geometries obtained corresponded to minima and not saddle points (i.e. global minima). California NanoSystems Institute at UCSB is acknowledged for computational resources.

Device Fabrication: Devices were prepared on cleaned, UV/ozone treated Corning 1737 glass patterned with 140 nm ITO. Active layers were spun cast to give 100 nm thicknesses (as determined using an Ambios XP-100 stylus profilometer) from solutions of p-DTS(FBTTh$_2$)$_2$ and PC$_{71}$BM at a weight ratio of 60:40 in chlorobenzene with or without 0.2% diiodo octane by volume, at an overall concentration of 35 mg mL$^{-1}$. Solutions were heated for several hours and residual solids filtered prior to casting at 90° C. Films were allowed to dry for 30 mins then heated to 70° C. for 10 mins under inert atmosphere to drive off residual solvent. Cathodes were deposited by sequential thermal evaporation of 5 nm Ca followed by 100 nm Al. Device characteristics were measured under illumination by a simulated 100 mWcm$^{-2}$ AM1.5G light source using a 300 W Xe arc lamp with an AM 1.5 global filter. Solar-simulator irradiance was calibrated using a standard silicon photovoltaic with a protective KG1 filter calibrated by the National Renewable Energy Laboratory. External quantum efficiencies were determined using a 75 W Xe source, monochromator, optical chopper, lock-in amplifier, and a National Institute of Standards and Technology-calibrated silicon photodiode was used for power-density calibration. Mismatch factors of the integrated quantum efficiency for devices was calculated to be less than 6%.

Example 1

Synthesis of 5-fluorobenzo[c][1,2,5]thiadiazole

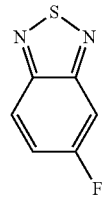

In a three-neck round-bottom flask, 4-fluoro-1,2-benzenediamine (5.5 g, 43.6 mmol) was fully dissolved in chloroform (500 mL) and triethylamine (30 mL). Thionyl chloride (7 mL, 96.0 mmol) was added drop wise via syringe. The solution stirred at 80° C. overnight. The reaction was allowed to cool and 250 mL of deionized water was added. The reaction was transferred to a separatory funnel and was washed several times with water. The organic phase was collected and dried over magnesium sulfate. The solution was filtered, concentrated and used directly. Recovered yield: 4.75 g (70%). $^1$H NMR (CDCl$_3$): δ 6.55 (dd, 1H, J=8.4, 5.4 Hz, CH), 6.36 (dd, 1H, J=10.2, 3.0 Hz, CH), 6.31 (td, 1H, J=8.4, 3.0 Hz, CH).

Example 2

Synthesis of 4,7-dibromo-5-fluorobenzo[c][1,2,5]thiadiazole

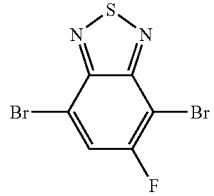

A round-bottom flask was charged with 5-fluorobenzo[c][1,2,5]thiadiazole (2.23 g, 14.5 mmol) followed by 48% hydrobromic acid (30 mL). Molecular bromine (7.47 mL, 145 mmol) was added drop wise and the reaction refluxed for 48 h. The reaction was allowed to cool to room temperature and diluted with chloroform and deionized water. The bi-phasic mixture was transferred to a separatory funnel and washed several times with water, rinsed with saturated sodium sulfite and rinsed with saturated sodium bicarbonate. Organics were collected and dried over magnesium sulfate. The solution was filtered and concentrated with silica. The compound was purified by flash column chromatography using a hexanes/chloroform gradient. Isolation of pure fractions afforded a white solid. Yield: 2.58 g (57%). $^1$H NMR (CDCl$_3$): δ 7.79 (d, 1H, J=8.4 Hz).

Example 3

Synthesis of 4-bromo-5-fluoro-7-(5'-hexyl-[2,2'-bithiophene]-5-yl)benzo[c][1,2,5]thiadiazole

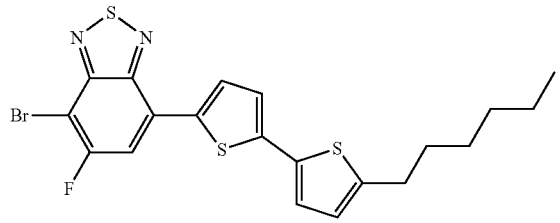 [SMILES: CCCCCCc1ccc(-c2ccc(-c3cc(F)c(Br)c4nsnc34)s2)s1]

In a N$_2$ filled glove box a 20 mL glass tube was charged with 4,7-dibromo-5-fluorobenzo[c][1,2,5]thiadiazole (FBTBr$_2$, 326 mg, 1.05 mmol), 5'-Hexyl-2,2'-bithiophene-5-trimethylstannane (432 mg, 1.05 mmol), Pd(PPh$_3$)$_4$ (50 mg, 0.04 mmol) and Toluene (15 mL), and sealed with a Teflon® cap. The reaction mixture was heated to 80° C. for 48 h. Upon cooling, the material was then loaded onto silica and purified by flash chromatography using a hexanes/chloroform gradient. After fraction collection and solvent removal an orange solid was obtained. Recovered yield: 294 mg (64%). $^1$H NMR (CDCl$_3$): δ 8.04 (d, J=3.6 Hz, 1H, CH), 7.67 (d, J=10.2 Hz, 1H, CH), 7.19 (d, J=3.6 Hz, 1H, CH), 7.12 (d, J=3.6 Hz, 1H, CH), 6.73 (d, J=3.6 Hz, 1H, CH), 2.82 (t, J=7.8 Hz, 2H, CH$_2$), 1.70 (m, J=7.5 Hz, 2H, CH$_2$), 1.40 (br m, 2H, CH$_2$), 1.34 (br m, 2H, CH$_2$), 1.32 (br m, 2H, CH$_2$), 0.90 (t, J=7.2 Hz, 3H, CH$_3$).

Example 4

Synthesis of 7,7'-(4,4-bis(2-ethylhexyl)-4H-silolo[3,2-b:4,5-b']dithiophene-2,6-diyl)bis(6-fluoro-4-(5'-hexyl-[2,2'-bithiophen]-5-yl)benzo[c][1,2,5]thiadiazole)

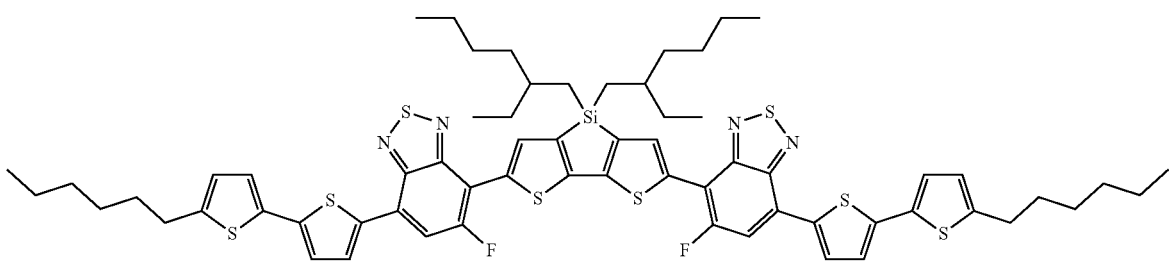 [SMILES: CCCCCCc1ccc(-c2ccc(-c3cc(F)c(-c4cc5c(s4)-c4sc(-c6c(F)cc(-c7ccc(-c8ccc(CCCCCC)s8)s7)c7nsnc67)cc4[Si]5(CC(CC)CCCC)CC(CC)CCCC)c4nsnc34)s2)s1]

In a N₂ filled glove box a 20 mL glass tube was charged with 4-bromo-5-fluoro-7-(5'-hexyl-[2,2'-bithiophene]-5-yl) benzo[c][1,2,5]thiadiazole (325 mg, 0.675 mmol), 5,5'-Bis (trimethylstannyl)-3,3'-di-2-ethylhexylsilylene-2,2'-bithiophene (250 mg, 0.338 mmol), Pd(PPh₃)₄ (30 mg, 0.024 mmol) and Toluene (15 mL), and sealed with a Teflon® cap. The reaction mixture was heated to 100° C. for 1 minute, 125° C. for 1 minute, 140° C. for 10 minutes, 150° C. for 10 minutes, and 160° C. for 10 minutes using a Biotage microwave reactor. Upon cooling, the material was then loaded onto silica, washed with methanol and purified by flash chromatography using a hexanes/chloroform gradient in duplicate. After fraction collection and solvent removal a metallic purple solid was obtained. The solid was slurried in a 3:1 mixture of methanol and hexanes, sonicated for 1 hour and stirred overnight. The suspension was filtered, washed with acetone and dried in vacuo. The product was recovered as a metallic purple solid. Recovered yield: 230 mg (56%). ¹H NMR (CDCl₃): δ 8.35 (t, 2H, CH), 8.05 (d, J=3.6 Hz, 2H, CH), 7.75 (d, J=6.9 Hz, 2H, CH), 7.20 (d, J=3.6 Hz, 2H, CH), 7.13 (d, J=3.6 Hz, 2H, CH), 6.74 (d, J=3.6 Hz, 2H, CH), 2.83 (t, J=7.5 Hz, 4H, CH₂), 1.71 (m, 4H, CH₂), 1.56 (br m, 2H, CH₂), {1.40 (br m, n₁ H) –1.33 (br m, n₂ H) –1.24 (br m, n₃ H), where n₁+n₂+n₃=30H}, 1.14 (br m, 4H, CH₂), 0.91 (m, 6H, CH₃), 0.84 (br m, 12H, CH₃).

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain changes and modifications will be practiced. Therefore, the description and examples should not be construed as limiting the scope of the invention.

What is claimed is:

1. An electronic or optoelectronic heterojunction device, wherein the active layer comprises a compound having the formula:

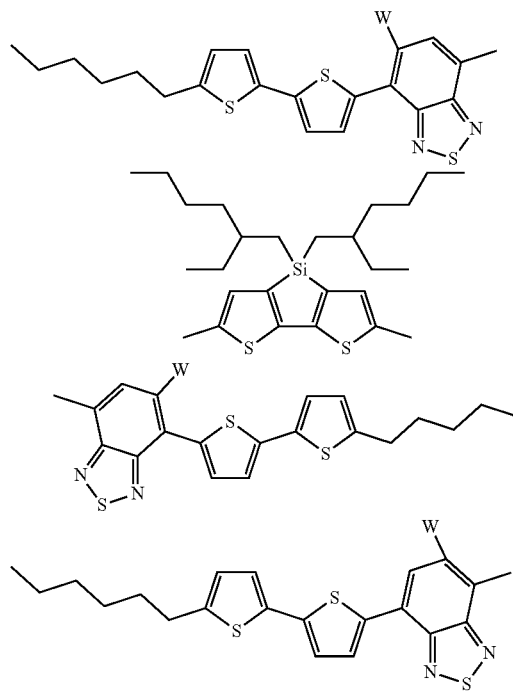

or

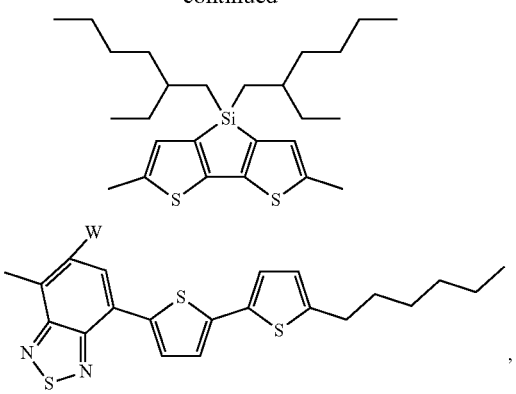

wherein W is selected from F, Cl, Br, I, —CN, —CF₃, —CHF₂, or —CH₂F.

2. The electronic or optoelectronic device according to claim 1, wherein the active layer comprises a compound having the formula:

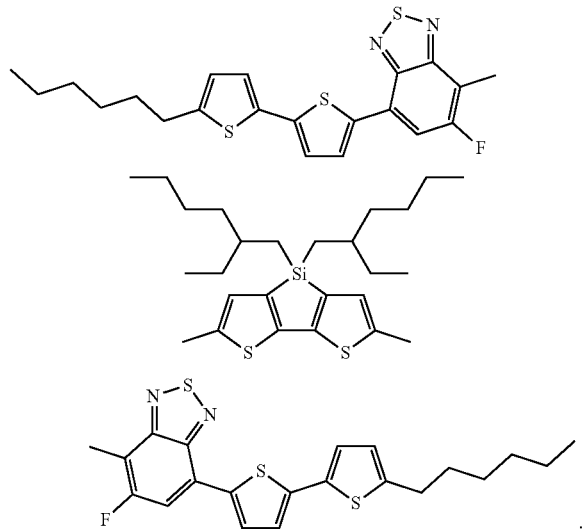

3. The electronic or optoelectronic device according to claim 1, wherein the active layer comprises a compound having the formula:

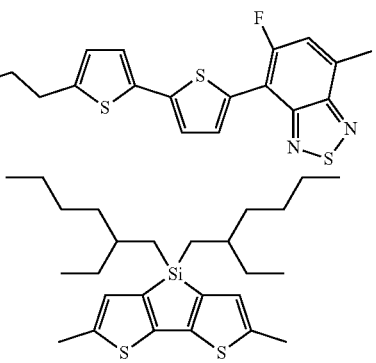

101

-continued

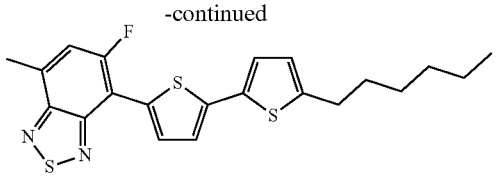

4. The electronic or optoelectronic device according to claim 1, wherein said device is a solar cell.

102

5. The device of claim 1, wherein said device comprises:
1) a first hole-collecting electrode optionally coated onto a transparent substrate;
2) a first optional layer or layers adjacent to the first electrode, said first optional layer or layers selected from the group consisting of an electron-blocking layer, an exciton-blocking layer, and a hole-transporting layer;
3) a layer comprising a mixture of an electron acceptor material and an organic non-polymeric electron donor, said electron donor comprising a compound a compound having the formula:

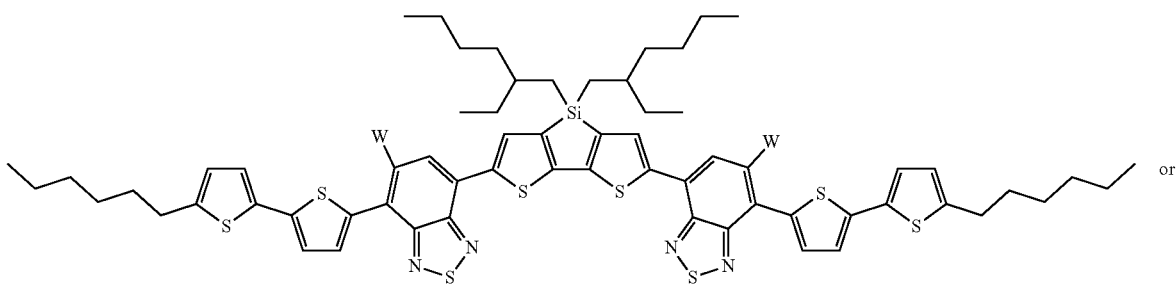 or

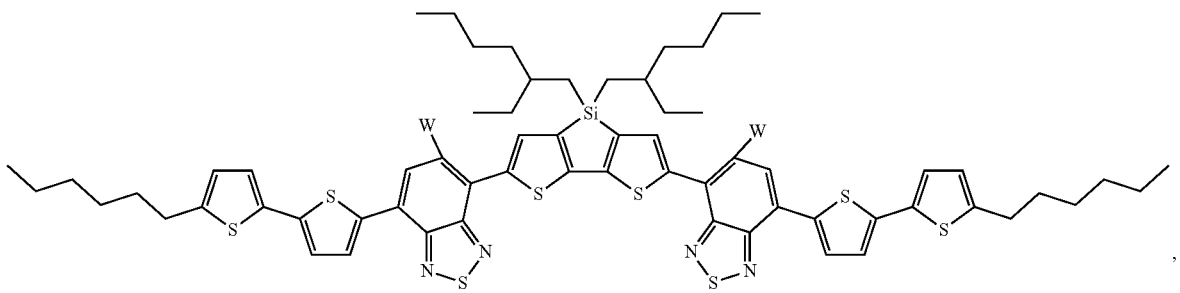, wherein W is selected from F, Cl, Br, I, —CN, —CF₃, —CHF₂, or —CH₂F;

4) a second optional layer or layers, said second optional layer or layers selected from the group consisting of a hole-blocking layer, an exciton-blocking layer, and an electron-transporting layer; and 5) a second electron-collecting electrode.

6. The device of claim 1, wherein said device comprises:
1) a first hole-collecting electrode optionally coated onto a transparent substrate;
2) a first optional layer or layers adjacent to the first electrode, said first optional layer or layers selected from the group consisting of an electron-blocking layer, an exciton-blocking layer, and a hole-transporting layer;
3) a layer comprising a mixture of an organic non-polymeric electron acceptor material and an electron donor, said electron acceptor comprising a compound having the formula:

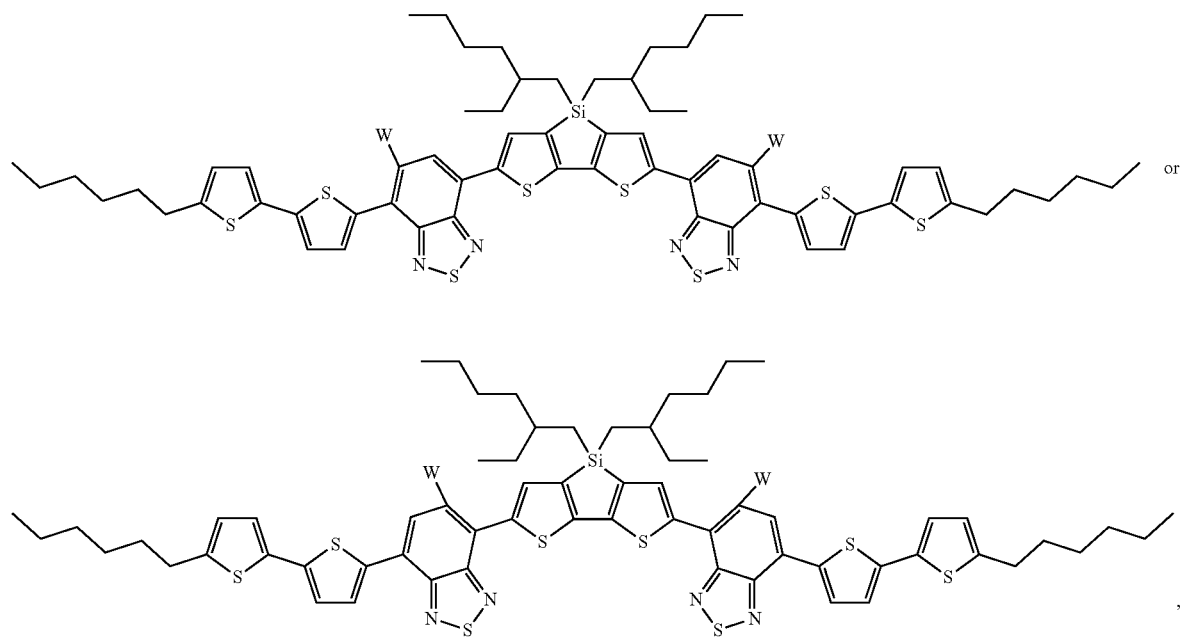

or wherein W is selected from F, Cl, Br, I, —CN, —CF₃, —CHF₂, or —CH₂F;

4) a second optional layer or layers, said second optional layer or layers selected from the group consisting of a hole-blocking layer, an exciton-blocking layer, and an electron-transporting layer; and 5) a second electron-collecting electrode.

7. The device of claim 5, wherein said electron donor comprises a compound a compound having the formula:

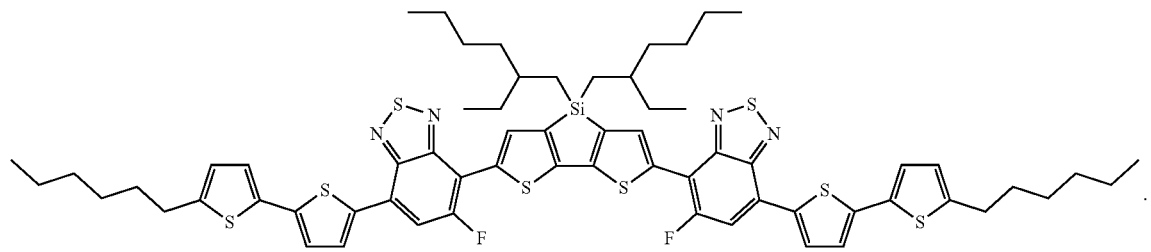 [SMILES: CCCCCCc1ccc(-c2ccc(-c3cc(F)c(-c4cc5c(s4)-c4sc(-c6c(F)cc(-c7ccc(-c8ccc(CCCCCC)s8)s7)c7nsnc67)cc4[Si]5(CC(CC)CCCC)CC(CC)CCCC)c4nsnc34)s2)s1]

8. The device of claim 5, wherein said electron donor comprises a compound a compound having the formula:
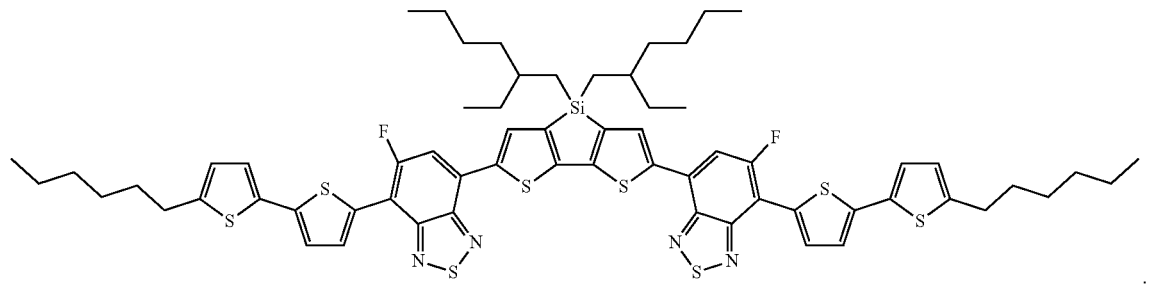 [SMILES: CCCCCCc1ccc(-c2ccc(-c3c(F)cc(-c4cc5c(s4)-c4sc(-c6cc(F)c(-c7ccc(-c8ccc(CCCCCC)s8)s7)c7nsnc67)cc4[Si]5(CC(CC)CCCC)CC(CC)CCCC)c4nsnc34)s2)s1]
9. The device of claim 6, wherein said electron acceptor comprises a compound having the formula:
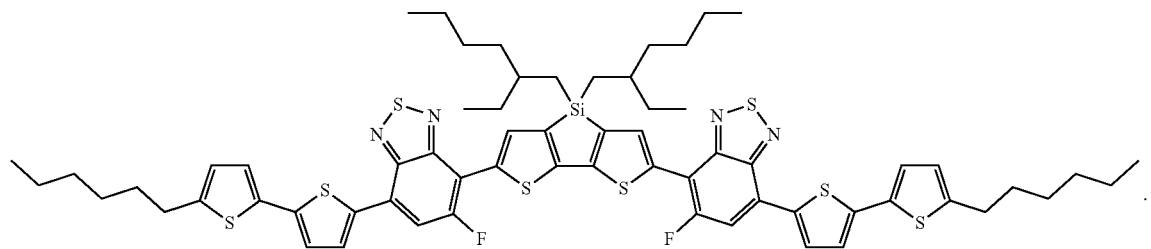 [SMILES: CCCCCCc1ccc(-c2ccc(-c3cc(F)c(-c4cc5c(s4)-c4sc(-c6c(F)cc(-c7ccc(-c8ccc(CCCCCC)s8)s7)c7nsnc67)cc4[Si]5(CC(CC)CCCC)CC(CC)CCCC)c4nsnc34)s2)s1]
10. The device of claim 6, wherein said electron acceptor comprises a compound having the formula:
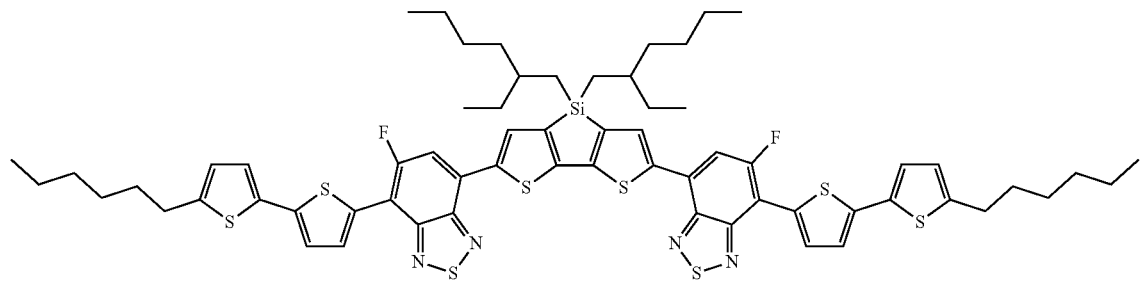 [SMILES: CCCCCCc1ccc(-c2ccc(-c3c(F)cc(-c4cc5c(s4)-c4sc(-c6cc(F)c(-c7ccc(-c8ccc(CCCCCC)s8)s7)c7nsnc67)cc4[Si]5(CC(CC)CCCC)CC(CC)CCCC)c4nsnc34)s2)s1]
* * * * *